United States Patent
Daley et al.

(10) Patent No.: US 11,261,430 B2
(45) Date of Patent: Mar. 1, 2022

(54) HEMATOPOIETIC STEM AND PROGENITOR CELLS DERIVED FROM HEMOGENIC ENDOTHELIAL CELLS

(71) Applicant: THE CHILDREN'S MEDICAL CENTER CORPORATION, Boston, MA (US)

(72) Inventors: George Q. Daley, Weston, MA (US); Ryohichi Sugimura, Boston, MA (US)

(73) Assignee: THE CHILDREN'S MEDICAL CENTER CORPORATION, Boston, MA (US)

(*) Notice: Subject to any disclaimer, the term of this patent is extended or adjusted under 35 U.S.C. 154(b) by 475 days.

(21) Appl. No.: 16/098,359

(22) PCT Filed: May 3, 2017

(86) PCT No.: PCT/US2017/030822
§ 371 (c)(1),
(2) Date: Nov. 1, 2018

(87) PCT Pub. No.: WO2017/192708
PCT Pub. Date: Nov. 9, 2017

(65) Prior Publication Data
US 2019/0119643 A1 Apr. 25, 2019

Related U.S. Application Data

(60) Provisional application No. 62/331,108, filed on May 3, 2016, provisional application No. 62/468,585, filed on Mar. 8, 2017.

(51) Int. Cl.

| | | |
|---|---|---|
| *A61K 48/00* | (2006.01) | |
| *C12N 5/02* | (2006.01) | |
| *C12N 5/071* | (2010.01) | |
| *C07H 21/04* | (2006.01) | |
| *C12N 5/0789* | (2010.01) | |
| *A61K 35/44* | (2015.01) | |
| *A61K 35/28* | (2015.01) | |
| *C12N 15/63* | (2006.01) | |

(52) U.S. Cl.
CPC .......... *C12N 5/0647* (2013.01); *A61K 35/28* (2013.01); *A61K 35/44* (2013.01); *C07H 21/04* (2013.01); *C12N 15/63* (2013.01); *C12N 2501/60* (2013.01); *C12N 2506/02* (2013.01); *C12N 2510/00* (2013.01)

(58) Field of Classification Search
CPC ...... A61K 35/28; C12N 5/0647; C12N 15/63; C12N 2501/60; C12N 2506/02; C12N 2510/00; C07H 21/04
See application file for complete search history.

(56) References Cited

U.S. PATENT DOCUMENTS

| 2014/0234971 A1 | 8/2014 | Slukvin et al. |
| 2015/0004145 A1 | 1/2015 | Lemischka et al. |
| 2015/0361398 A1 | 12/2015 | Sandler et al. |

FOREIGN PATENT DOCUMENTS

| CN | 107964536 A | 4/2018 |
| WO | 2014113415 A1 | 7/2014 |
| WO | 2017/192708 A1 | 11/2017 |

OTHER PUBLICATIONS

Romito et al., 2016, Hindawi Publishing Corporation, Stem Cell International, vol. 2016, Article ID 9451492, p. 1-20.*
Narsinh et al., 2011, Molecular therapy, vol. 9, No. 4, p. 635-638.*
Bellin et al., 2012, Nature reviews/Molecular Cell Biology, vol. 13, p. 713-726.*
Burridge et al., 2011, PLoS ONE, vol. 6, No. 4, e18293, p. 1-16.*
Paes et al., 2017, Cell Biology and Toxicology, vol. 33, No. 3, pp. 233-250.*
Kim et al., 2014, IOVS, vol. 55, No. 8, p. 5099-5108.*
Stern-Straeter et al., 2014, International Journal of Molecular Medicine, vol. 33, p. 160-170.*
Dib et al., 2011, J. of Cardiovasc. Trans. Res., 4:177-181.*
Wu et al., 2012, Aging Research reviews, vol. 11, p. 32-40.*
Agrahari et al., 2017, Expert Opinion on Drug Delivery, vol. 14, No. 10, p. 1145-1162.*
Ikonomou et al., 2017, Am J Respir Crit Care Med, vol. 195, p. 13-14.*
Ikehara et al., 2013, Frontier in Cell and Developmental Biology, vol. 1, Article 2, p. 1-2.*
Cooper et al., 2015, International Journal of Surgery, vol. 23, p. 211-216.*
Liu et al., 2017, Frontiers in Immunology, vol. 8, article 645, p. 1-6.*
Lis et al., "Conversion of adult endothelium to immunocompetent haematopoietic stem cells " Nature 545 (7655):439-445 (2017).
Sugimura et al., "Haematopoietic stem and progenitor cells from human pluripotent stem cells." Nature 545 (7655):432-438 (2017).
Okita et al. "An efficient nonviral method to generate integration-free human-induced pluripotent stem cells from cord blood and peripheral blood cells." Stem Cells 31(3): 458-466 (2013).

* cited by examiner

*Primary Examiner* — Shin Lin Chen
(74) *Attorney, Agent, or Firm* — Nixon Peabody LLP; David S. Resnick; Teresa A. Ptashka

(57) ABSTRACT

Embodiments herein relate to in vitro production methods of hematopoietic stem cell (HSC) and hematopoietic stem and progenitor cell (HSPC) that have long-term multilineage hematopoiesis potentials upon in vivo engraftment. The HSC and HSPCs are derived from pluripotent stem cells-derived hemogenic endothelia cells (HE).

14 Claims, 17 Drawing Sheets
Specification includes a Sequence Listing.

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccctatcgat cgatctctac ct                                              22

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agctcgttta gtgaaccgtc agatc                                           25

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgtcgccgtc cagctcgacc ag                                              22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctgggacgt cgtatgggta                                                 20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```
ctgaggagaa gtctgccgtt a                                       21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agcatcagga gtggacagat                                         20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggatgatct caagggcac                                          19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcagtggtat ctggaggaca                                         20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcaagaaggt gctgacttcc                                         20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accatcacgt tacccaggag                                         20

HEMATOPOIETIC STEM AND PROGENITOR CELLS DERIVED FROM HEMOGENIC ENDOTHELIAL CELLS

CROSS-REFERENCE TO RELATED APPLICATIONS

This application is a 35 U.S.C. § 371 National Phase Entry Application of International Application PCT/US2017/030822 filed on May 3, 2017, which designates the U.S., and which claims the benefit under 35 U.S.C. § 119(e) of the U.S. Provisional Application No. 62/331,108 filed on May 3, 2016, and the U.S. Provisional Application No. 62/468,585 filed on Mar. 8, 2017, the contents of each of which are incorporated herein by reference in their entireties.

SEQUENCE LISTING

The sequence listing of the present application has been submitted electronically via EFS-Web as an ASCII formatted sequence listing with a file name "701039-087152-PCT_SL.txt", creation date of Oct. 25, 2018 and a size of 2,646 bytes. The sequence listing submitted via EFS-Web is part of the specification and is herein incorporated by reference in its entirety.

GOVERNMENT SUPPORT

This invention was made with Government support under Grant No.: R37AI039394, R24DK092760, and UO1-HL100001 awarded by the National Institutes of Health. The Government has certain rights in the invention.

FIELD OF THE DISCLOSURE

This disclosure relates to in vitro production methods of hematopoietic stem cell (HSC) and hematopoietic stem and progenitor cell (HSPC) starting from hemogenic endothelia cells (HE) that were induced from pluripotent stem cells, including induced pluripotent stem cells (iPSC), and also relates to long-term multilineage hematopoiesis with the engraftment of these HSCs and HSCPs.

BACKGROUND

There is a lack of supply of functional blood cells for in vivo cellular replacement therapy, and for in vitro studies of disease modeling, drug screening, and hematological diseases. Bone marrow transplantation is by far the most established cellular replacement therapy for a variety of hematological disorders. The functional unit of a bone marrow transplant is the hematopoietic stem cell (HSC), which resides at the apex of a complex cellular hierarchy and replenishes blood development throughout life. However, the scarcity of HLA-matched HSCs or patient-specific HSCs severely limits the ability to carry out transplantation, disease modeling, drug screening, and in vitro studies of hematological diseases. Often, there is not a large enough cell population transplanted to ensure sufficient engraftment and reconstitution in vivo.

As such, many studies have been developed to generate HSCs from alternative sources. For example, reprogramming of somatic cells to induced pluripotent stem cells (iPSC) has provided access to a wide array of patient-specific pluripotent cells, a promising source for disease modeling, drug screens and cellular therapies. Pluripotent cells are induced in human and mouse somatic cells by the forced expression of the reprogramming factors: OCT4 (Oct4) and SOX2 (Sox2) with either the combinations of KLF4 (Klf4) and c-MYC (c-Myc) or NANOG (Nanog) and LIN28 (Lin28). Mouse iPS cell lines derived from bone marrow hematopoietic progenitor cells has been reported. Derivation of human iPS cells from postnatal human blood cells, from granulocyte colony-stimulating factor (G-CSF) mobilized peripheral blood (PB) CD34+ cells, and from human cord blood (CB) and adult bone marrow (BM) CD34+ cells without any pre-treatment such as G-CSF mobilization has been also reported. The iPSCs have been shown to differentiate into various cells belonging to the three germ layers, as demonstrated by the analysis of teratomas generated from human and mouse iPS cells. In addition, the pluripotency of iPS cells is confirmed by the contribution of iPS cell-derived cells to various organs of the chimeric mice developed from iPS cell-introduced blastocysts.

Another approach to generate HSCs from pluripotent stem cells (PSC) is to specify HSCs from its ontogenetic precursors. It is now widely accepted that HSCs originate from hemogenic endothelium (HE) in the aorta-gonad-mesonephros (AGM) and arterial endothelium in other anatomical sites. Recent work on the directed differentiation of HE from human PSC have provided valuable insights into some of the signaling pathways that control the emergence of primitive or definitive populations; however, the endothelial-to-hematopoietic transition remains incompletely understood in human hematopoietic development, making rational intervention challenging. For example, there are reports of induced definitive HE differentiated from human embryonic bodies (EB) that were derived from iPS cells. However, these HE from PSCs do not engraft in vivo. In contrast, other have shown that real hemogenic cells from human fetal tissues can engraft in mice, indicating missing signals to confer HSC fate on PSCs.

Therefore, there are still barriers to the generation of HSC from these alternative sources. In addition to the cell quantity and cell source problems, there is still a hurdle in producing hematopoietic stem and progenitor cells derived from human pluripotent stem cells (hPSCs) or the differentiated cells therefrom that would engraft in vivo. Mostly, the primitive HSC and HSPC produced from these alternative sources do not sustain blood production in vivo.

SUMMARY OF THE DISCLOSURE

It is difficult to harvest de novo enough hematopoietic stem cells (HSCs) and hematopoietic stem and progenitor cells (HSPCs) from animals and humans. It is also difficult to ex vivo culture expand enough of these cells for any meaningful therapeutic purposes. Sometimes, the ex vivo culture-expanded cells do not differentiate into all the hematopoietic lineage potentials.

Additionally, it is difficult to differentiate HSCs and HSPCs from pluripotent stem cells (PSCs) where the HSCs and HSPCs exhibit all the hematopoietic lineage potentials. One of the most common problems with HSCs and HSPCs derived from PSCs is that the HSCs and HSPCs do not engraft well and in sufficient number in the host after transplantation to sustain blood production in vivo. One of the problems to solve in achieving in vivo long-term multilineage hematopoiesis with the engraftment of these HSCs and HSCPs from the PSCs.

The inventors have found a process to make PSCs-derived HSCs and HSPCs that would differentiate into all the hematopoietic lineage potentials and would also engraft well in the host after transplantation so that there is sufficient engrafted cells to sustain blood production in vivo. This discovery provides a method for producing functionally relevant HSCs and HSPCs in sufficient quantities for both meaningful experimental and therapeutic purposes. For example, in vitro experiments, these PSCs-derived HSCs and HSPCs can be differentiated to the desired hematopoietic lineage, e.g., erythroid cells, lymphoid cells, and myeloid cells, for further studies, e.g, drug studies. For example, in in vivo studies, these PSCs-derived HSCs and HSPCs would engraft in a host, and differentiate into a variety of hematopoietic progeny cells, and reconstitute and populate the circulatory and immune system of the host.

Embodiments of the present disclosure are based, in part, to the discovery of a few key transcription factors that would bring about the differentiation of HSCs and HSPCs that are derived from pluripotent stem cells derived hemogenic endothelia cells (HE). First, the inventors showed that embryonic bodies (EB) are made from pluripotent stem cells, e.g., including induced pluripotent cells. Second, the HE are harvested from the EB, and cultured to induce endothelial-to-hematopoietic transition (EHT) in vitro. Then, the HE cells are transfected with coding gene sequences of at least the following transcription factors: ERG, HOXA9, HOXA5, LCOR and RUNX1, for the expression of the respective transcription factors, thereby to promote differentiation of the HE into HSCs and HSPCs that exhibit all the hematopoietic lineage potentials. These multilineage HSCs and HSPCs engraft well in recipient host after implantation.

Accordingly, in one aspect, provided herein is a method for making hematopoietic stem cells (HSCs) and hematopoietic stem and progenitor cells (HSPCs) comprising in vitro transfecting hemogenic endothelia cells (HE) with an exogenous gene coding copy of each of the following transcription factors: ERG, HOXA9, HOXA5, LCOR and RUNX1, wherein the transcription factors are expressed in the transfected cells to produce a population of multilineage HSCs and HSPCs that engrafts in recipient host after implantation. Additional transcription factors, HOXA10 and SPI1, are optionally included.

In another aspect, this disclosure provides is a method of making hematopoietic stem cells (HSCs) and hematopoietic stem and progenitor cells (HSPCs) comprising (a) generating embryonic bodies (EB) from pluripotent stem cells; (b) isolating hemogenic endothelia cells (HE) from the resultant population of EB; (c) inducing endothelial-to-hematopoietic transition (EHT) in culture in the isolated HE in order to obtain hematopoietic stem cells, and (d) in vitro transfecting the induced HE with an exogenous gene coding copy of each of the following transcription factors ERG, HOXA9, HOXA5, LCOR and RUNX1. Additional transcription factors, HOXA10 and SPI1, are optionally included.

In another aspect, this disclosure provides is an engineered cell derived from a population of HE that is produced by a method comprising (a) generating embryonic bodies (EB) from pluripotent stem cells; (b) isolating hemogenic endothelia cells (HE) from the resultant population of EB; (c) inducing endothelial-to-hematopoietic transition (EHT) in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. Additional transcription factors, HOXA10 and SPI1, are optionally included.

In another aspect, this disclosure provides is an engineered cell derived from a population of HE that is produced by a method comprising in vitro transfecting the population of HE with an exogenous gene coding copy of each of the following transcription factors ERG, HOXA9, HOXA5, LCOR and RUNX1. Additional transcription factors, HOXA10 and SPI1, are optionally included.

In another aspect, this disclosure provides is an engineered cell comprises an exogenous copy of each of the following transcription factors ERG, HOXA9, HOXA5, LCOR and RUNX1. Additional transcription factors, HOXA10 and SPI1, are optionally included.

In another aspect, this disclosure provides is a composition comprising a population of engineered cells derived from a population of HE and produced by a method comprising (a) generating embryonic bodies (EB) from pluripotent stem cells; (b) isolating hemogenic endothelia cells (HE) from the resultant population of EB; (c) inducing endothelial-to-hematopoietic transition (EHT) in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. Additional transcription factors, HOXA10 and SPI1, are optionally included. In some embodiments, this composition is useful for cellular replacement therapy in a subject. In other embodiments, this composition is useful for research and laboratory uses. For examples, in drug screening and testing.

In another aspect, this disclosure provides is a composition comprising a population of engineered cells derived from a population of HE and produced by a method comprising in vitro transfecting the population of HE with an exogenous gene coding copy of each of the following transcription factors ERG, HOXA9, HOXA5, LCOR and RUNX1. Additional transcription factors, HOXA10 and SPI1, are optionally included. In some embodiments, this composition is useful for cellular replacement therapy in a subject. In other embodiments, this composition is useful for research and laboratory uses.

In another aspect, this disclosure provides is a composition comprising a population of engineered cells wherein the cells comprise an exogenous gene coding copy of each of the following transcription factors ERG, HOXA9, HOXA5, LCOR and RUNX1. Additional transcription factors, HOXA10 and SPI1, are optionally included. Additionally, the engineered cells further comprises reprogramming factors OCT4, SOX2, KLF4 and optionally c-MYC or NANOG and LIN28.

In another aspect, this disclosure provides is a pharmaceutical composition comprising a population of engineered cells derived from a population of HE and a pharmaceutically acceptable carrier, wherein the engineered cells are produced by a method comprising (a) generating embryonic bodies (EB) from pluripotent stem cells; (b) isolating hemogenic endothelia cells (HE) from the resultant population of EB; (c) inducing endothelial-to-hematopoietic transition (EHT) in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. Additional transcription factors, HOXA10 and SPI1, are optionally included. In some embodiments, this pharmaceutical composition is useful for cellular replacement therapy in a subject.

In another aspect, this disclosure provides is a pharmaceutical composition comprising a population of engineered cells derived from a population of HE and a pharmaceutically acceptable carrier, wherein the engineered cells are produced by a method comprising in vitro transfecting the population of HE with an exogenous gene coding copy of each of the following transcription factors ERG, HOXA9, HOXA5, LCOR and RUNX1. Additional transcription factors, HOXA10 and SPI1, are optionally included. In some embodiments, this pharmaceutical composition is useful for cellular replacement therapy in a subject.

In another aspect, this disclosure provides is a pharmaceutical composition comprising a population of engineered cells and a pharmaceutically acceptable carrier, wherein the engineered cells comprise an exogenous gene coding copy of each of the following transcription factors ERG, HOXA9, HOXA5, LCOR and RUNX1. Additional transcription factors, HOXA10 and SPI1, are optionally included.

In another aspect, this disclosure provides is a method of cellular replacement therapy in a subject in need thereof, the method comprising administering a population of engineered cells to a recipient subject, the population of engineered cells are produced by a method comprising (a) generating embryonic bodies (EB) from pluripotent stem cells; (b) isolating hemogenic endothelia cells (HE) from the resultant population of EB; (c) inducing endothelial-to-hematopoietic transition (EHT) in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. Additional transcription factors, HOXA10 and SPI1, are optionally included.

In another aspect, this disclosure provides is a method of cellular replacement therapy in a subject in need thereof, the method comprising administering a population of engineered cells to a recipient subject, the population of engineered cells are produced by a method comprising in vitro transfecting the population of HE with an exogenous gene coding copy of each of the following transcription factors ERG, HOXA9, HOXA5, LCOR and RUNX1. Additional transcription factors, HOXA10 and SPI1, are optionally included.

In another aspect, this disclosure provides is a method of cellular replacement therapy in a subject in need thereof, the method comprising administering a population of engineered cells to a recipient subject, the population of engineered cells comprise an exogenous gene coding copy of each of the following transcription factors ERG, HOXA9, HOXA5, LCOR and RUNX1. Additional transcription factors, HOXA10 and SPI1, are optionally included.

In another aspect, this disclosure provides is an engineered cell derived from a population of HE and produced by a method described herein.

In another aspect, this disclosure provides is a composition comprising a population of engineered cells described herein.

In another aspect, this disclosure provides is a pharmaceutical composition comprising a population of engineered cells described herein and a pharmaceutically acceptable carrier.

In another aspect, this disclosure provides is a pharmaceutical composition described herein for use in cellular replacement therapy in a subject.

In another aspect, this disclosure provides is a method of cellular replacement therapy in a subject in need thereof, the method comprising administering a population of engineered cells described, or a composition described, or a pharmaceutical composition described to a recipient subject.

In another aspect, this disclosure provides is a use of an engineered cell described herein, a composition comprising of engineered cells described herein, or a pharmaceutical composition comprising of engineered cells described herein for the cellular replacement therapy in a subject in need thereof, or for the manufacture of medicament for cellular replacement therapy in a subject in need thereof.

In one embodiment of any one aspect described, the method described is an in vitro method.

In one embodiment of any one aspect described, the EB are generated or induced from PSC by culturing or exposing the PSC to mophogens for about 8 days.

In one embodiment of any one aspect described, the mophogens for generating EBs from PSC are selected from the group consisting of holo-transferrin, mono-thioglycerol (MTG), ascorbic acid, bone morphogenetic protein (BMP)-4, basic fibroblast growth factor (bFGF), SB431542, CHIR99021, vascular endothelial growth factor (VEGF), interleukin (IL)-6, insulin-like growth factor (IGF)-1, interleukin (IL)-11, stem cell factor (SCF), erythropoietin (EPO), thrombopoietin (TPO), interleukin (IL)-3, and Fms related tyrosine kinease 3 ligand (Flt-3L). The combination of all these factors required to produce definitive HE.

In one embodiment of any one aspect described, the method described herein further comprises selecting EBs that are formed from the PSC after having been exposed or contacted with the described morphogens.

In one embodiment of any one aspect described, the selected EBs are less than 800 microns in size and are selected.

In one embodiment of any one aspect described, the EB cells within the selected EBs are compactly adhered to each other and requires trypsin digestion in order to dissociate the cells to individual cells.

In one embodiment of any one aspect described, the EB cells of the selected EBs are dissociated prior to the isolation of HE therefrom.

In one embodiment of any one aspect described, the population of PSC used for generating EBs is induced pluripotent stem cells (iPS cells) or embryonic stem cells (ESC).

In one embodiment of any one aspect described, the iPS cells are produced by introducing only reprogramming factors OCT4, SOX2, and KLF4, and optionally c-MYC into mature cells. In one embodiment of any one aspect described, the iPS cells are produced by introducing only reprogramming factors OCT4, SOX2, and KLF4, and optionally NANOG and LIN28 into mature cells. The introduction is via any method known in the arts, e.g., viral vectors (AAV, lentiviral, retroviral vectors) that are known in the art.

In one embodiment of any one aspect described, the mature cells for producing iPS cells are selected from the group consisting of B lymphocytes (B-cells), T lymphocytes, (T-cells), fibroblasts, and keratinocytes. Any matured, differentiated cells in the body of a multicellular organism can be used to produce iPCs.

In one embodiment of any one aspect described, the induced pluripotent stem cells are produced by introducing the reprogramming factors once, or two or more times into the mature cells.

In one embodiment of any one aspect described, the disclosed transcription factors are expressed in the transfected cells, that is, the respective transcription factors: ERG, HOXA9, HOXA5, LCOR, RUNX1, HOXA10, or SPI1, is expressed in the transfected cells.

In another embodiment of any one aspect described, the disclosed transcription factors are expressed in the engineered cells of this disclosure.

In one embodiment of any one aspect described, the expression of the disclosed transcription factors in the transfected or engineered cells produces a population of multi-lineage HSCs and HSPCs.

In one embodiment of any one aspect described, the population of multi-lineage HSCs and HSPCs, produced by the expression of the disclosed transcription factors in the transfected or engineered cells, engrafts in vivo in the recipient subject and produces blood cells in vivo.

In one embodiment of any one aspect described, the population of multilineage HSCs and HSPCs, produced by the expression of the disclosed transcription factors in the transfected or engineered cells, reconstitutes the hematopoietic system in vivo in the recipient subject.

In one embodiment of any one aspect described, the population of multi-lineage HSCs and HSPCs differentiate to myeloid cells in vivo after implantation in a host recipient subject. The myeloid cells produce MPO upon PMA or cytokine stimulation in vivo.

In one embodiment of any one aspect described, the population of multi-lineage HSCs and HSPCs differentiate to functional T- and B-cells in vivo after implantation in a host recipient subject. The functional T- and B-cells produce IgM and IgG. The functional T- and B-cells also undergo immunoglobulin class switching in response to ovalbumin stimulation. The functional T- and B-cells also produces INF-γ.

In one embodiment of any one aspect described, the engineered cells disclosed herein express at least one of the following transcription factors: ERG, HOXA9, HOXA5, LCOR, RUNX1, HOXA10, or SPI1, from an exogenous gene encoding the transcription factors in the cells.

In one embodiment of any one aspect described, the engineered cells disclosed herein are multilineage HSCs and HSPCs that are CD34+.

In one embodiment of any one aspect described, the engineered cells disclosed herein are multilineage HSCs and HSPCs that are CD34+ and CD45+.

In one embodiment of any one aspect described, the engineered cells disclosed herein are multilineage HSCs and HSPCs that are CD34+CD45+ and CD38−.

In one embodiment of any one aspect described, the engineered cells disclosed herein are CD34+.

In one embodiment of any one aspect described, the engineered cells disclosed herein are are CD34+ and CD45+.

In one embodiment of any one aspect described, the engineered cells disclosed herein are CD34+CD45+ and CD38−.

In one embodiment of any one aspect described, the engineered cells disclosed herein are multilineage HSCs and HSPCs that engraft in vivo in a host recipient subject and produce blood cells in vivo.

In one embodiment of any one aspect described, the engineered cells disclosed herein are multilineage HSCs and HSPCs that reconstitutes the hematopoietic system in vivo when transplanted into a host recipient subject.

In one embodiment of any one aspect described, the engineered cells disclosed herein are multilineage HSCs and HSPCs that differentiate to myeloid cells in vivo, and the myeloid cells produce MPO upon PMA or cytokine stimulation in vivo.

In one embodiment of any one aspect described, the engineered cells disclosed herein are multilineage HSCs and HSPCs that differentiate to functional T- and B-cells in vivo, the functional T- and B-cells produce IgM and IgG. The functional T- and B-cells also undergo immunoglobulin class switching in response to ovalbumin stimulation. The functional T- and B-cells also produces INF-γ.

In one embodiment of any one aspect described, the HE are definitive HE.

In one embodiment of any one aspect described, the HE are FLK1+, CD34+, CD43−, and CD235A−. These biomarkers are those on HE before the endothelial-to-hematopoietic transition (EHT).

Definitive HE is a population that is defined by combination of surface antigen markers. CD34+FLK1+CD235A−CD43− before EHT.

In one embodiment of any one aspect described, the HE are isolated immediately from selected EBs and dissociated EB cells.

In one embodiment of any one aspect described, the HSCs are CD34+.

In one embodiment of any one aspect described, the HSCs are CD34+ and CD45+.

In one embodiment of any one aspect described, the HSPCs are CD34+.

In one embodiment of any one aspect described, the HSPCs are CD34+ and CD45+.

In one embodiment of any one aspect described, the EHT occurs by culturing the isolated HE in thrombopoietin (TPO), interleukin (IL)-3, stem cell factor (SCF), IL-6, IL-11, insulin-like growth factor (IGF)-1, erythropoietin (EPO), vascular endothelial growth factor (VEGF), basic fibroblast growth factor (bFGF), bone morphogenetic protein (BMP)4, Fms related tyrosine kinase 3 ligand (Flt-3L), sonic hedgehog (SHH), angiotensin II, and chemical AGTR1 (angiotensin II receptor type I) blocker losartan potassium.

In one embodiment of any one aspect described, the multilineage HSCs produced by the methods described in this disclosure are CD34+CD38−CD45+.

In one embodiment of any one aspect described, the multilineage HSPCs produced by the methods described in this disclosure are CD34+CD45+.

In one embodiment of any one aspect described, the engineered cell of this disclosure comprises an exogenous copy of each of the following transcription factors ERG, HOXA9, HOXA5, LCOR and RUNX1.

In one embodiment of any one aspect described, the engineered cell of this disclosure further comprises an exogenous copy of each of the following reprogramming factors OCT4, SOX2, KLF4 and optionally c-MYC. Alternate reprogramming factors in lieu of c-MYC are NANOG and LIN28.

In one embodiment of any one aspect described, the composition of engineered cells of this disclosure further comprises a pharmaceutically acceptable carrier.

In one embodiment of any one aspect described, the subject is a patient who has undergone chemotherapy or irradiation or both chemotherapy and irradiation, and manifest deficiencies in immune or blood function or lymphocyte reconstitution or both deficiencies in immune function and lymphocyte reconstitution.

In one embodiment of any one aspect described, the subject prior to implantation, the immune cells are treated ex vivo with prostaglandin E2 and/or antioxidant N-acetyl-L-cysteine (NAC) to promote subsequent engraftment in a recipient subject.

In one embodiment of any one aspect described, the engineered cells of this disclosure are autologous to the recipient subject or at least HLA type matched with the recipient subject.

Definitions

As used herein, the term "comprising" means that other elements can also be present in addition to the defined elements presented. The use of "comprising" indicates inclusion rather than limitation.

The term "consisting of" refers to methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the disclosure.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the embodiments of the present disclosure can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

In one embodiment, the "pharmaceutically acceptable" carrier does not include in vitro cell culture media.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

A "subject," as used herein, includes any animal that exhibits a symptom of a monogenic disease, disorder, or condition that can be treated with the cell-based therapeutics, and methods disclosed elsewhere herein. In one embodiment, a subject includes any animal that exhibits symptoms of a disease, disorder, or condition of the hematopoietic system, e.g., a hemoglobinopathy, that can be treated with the cell-based therapeutics, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

In one embodiment, as used herein "treatment" or "treating," includes any beneficial or desirable effect on the symptoms or pathology of a disease or pathological condition, and may include even minimal reductions in one or more measurable markers of the disease or condition being treated. In another embodiment, treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, the term "amount" refers to "an amount effective" or "an effective amount" of transduced therapeutic cells to achieve a beneficial or desired prophylactic or therapeutic result, including clinical results.

A "prophylactically effective amount" refers to an amount of transduced therapeutic cells effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of transduced therapeutic cells may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

As used herein, the terms "administering," refers to the placement of a composition or engineered cells of this disclosure into a subject by a method or route which results in at least a desired effects, for example, increase number of immune cells or blood cells or platelets. The composition or engineered cells of this disclosure can be administered by any appropriate route which results in an effective treatment in the subject.

As used herein, in one embodiment, the term "hematopoietic stem cell" or "HSC" refers to a stem cell that give rise to all the blood cell types of the three hematopoietic lineages, erythroid, lymphoid, and myeloid. These cell types include the myeloid lineages (monocytes and macrophages, neutrophils, basophils, eosinophils, erythrocytes, megakaryocytes/platelets, dendritic cells), and the lymphoid lineages (T-cells, B-cells, NK-cells). In one embodiment, the term "hematopoietic stem cell" or "HSC" refers to a stem cell that have the following cell surface markers: CD34+, CD59+, Thy1/CD90+, CD38lo/−, and C-kit/CD117+. In one embodiment, the term "hematopoietic stem cell" or "HSC" refers to a stem cell that is at least CD34+. In one embodiment, the term "hematopoietic stem cell" or "HSC" refers to a stem cell that is at least CD34+ and C-kit/CD117+. In another embodiment, the term HSC refers to a stem cell that is at least CD34+. In another embodiment, the term HSC refers to a stem cell that is at least CD34+/CD45+. In another embodiment, the term HSC refers to a stem cell that is at least CD34+/CD45+/CD38−.

As used herein, the terms "iPS cell" and "induced pluripotent stem cell" are used interchangeably and refers to a pluripotent cell artificially derived by the transfection of following reprogramming factors OCT4, SOX2, KLF4 and optionally c-MYC or optionally NANOG and LIN28, into a from a differentiated cell.

As used herein, the term "lineage" when used in the context of stem and progenitor cell differentiation and development refers to the cell differentiation and development pathway which the cell can take to becoming a fully differentiated cell. For example, a HSC has three hematopoietic lineages, erythroid, lymphoid, and myeloid; the HSC has the potential, ie., the ability, to differentiate and develop into those terminally differentiated cell types known for all these three lineages. When the term "multilineage" used, it means the cell is able in the future differentiate and develop into those terminally differentiated cell types known for more than one lineage. For example, the HSC has multilineage potential. When the term "limited lineage" used, it means the cell can differentiate and develop into those terminally differentiated cell types known for one lineage. For example, a common myeloid progenitor cell or a megakaryocyte-erythroid progenitor has a limited lineage because the cell can only differentiate and develop into those terminally differentiated cell types of the myeloid lineage and not that of the lymphoid lineage. Terminally differentiated cells of the myeloid lineage include erythrocytes, monocytes, macrophages, megakaryocytes, myeloblasts, dendritic cells, and granulocytes (basophils, neutrophils, eosinophils, and mast cells); and terminally differentiated cells of the lymphoid lineage include T lymphocytes/T cells, B lymphocytes/B cells, and natural killer cells.

As used herein, the term "a progenitor cell" refers to an immature or undifferentiated cell that has the potential later on to mature (differentiate) into a specific cell type, for example, a blood cell, a skin cell, a bone cell, or a hair cells. Progenitor cells have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. A progenitor cell also can proliferate to make more progenitor cells that are similarly immature or undifferentiated.

As used herein, the term "multilineage hematopoietic progenitor cells" or "hematopoietic stem and progenitor cells (HSPC)" refer to hematopoietic cells (cell that form the blood) that have the ability or potential to generate, or differentiate into, multiple types of hematopoietic lineage cells.

As used herein, the term "long-term" when used in the context of "multilineage hematopoiesis" refers to in vivo implanted HSCs and/or HSPCs being capable of producing the three hematopoietic lineage cells, erythroid, lymphoid, and myeloid, for up to at least 12 weeks post transplantation.

As used herein, the term "multilineage hematopoiesis" in the context of HSCs and/or HSPCs refers to these cells capable of producing at least the three hematopoietic lineage cells, erythroid, lymphoid, and myeloid.

The term "differentiated cell" is meant any primary cell that is not, in its native form, pluripotent as that term is defined herein. The term a "differentiated cell" also encompasses cells that are partially differentiated, such as multipotent cells (e.g. adult somatic stem cells). In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a mesodermal stem cell or a endodermal stem cell), which in turn can differentiate into other types of precursor cells further down the pathway (such as an tissue specific precursor, for example, a cardiomyocyte precursor, or a pancreatic precursoe), and then to an end-stage differentiated cell, which plays a characteristic role in a certain tissue type, and may or may not retain the capacity to proliferate further.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of muiltipotent cells include adult somatic stem cells, such as for example, hematopoietic stem cells and neural stem cells, hair follicle stem cells, liver stem cells etc. Multipotent means a stem cell may form many types of cells in a given lineage, but not cells of other lineages. For example, a multipotent blood stem cell can form the many different types of blood cells (red, white, platelets, etc. . . . ), but it cannot form neurons; cardiovascular progenitor cell (MICP) differentiation into specific mature cardiac, pacemaker, smooth muscle, and endothelial cell types; pancreas-derived multipotent progenitor (PMP) colonies produce cell types of pancreatic lineage (cells that produces insulin, glucagon, amylase or somatostatin) and neural lineage (cells that are morphologically neuron-like, astrocytes-like or oligodendrocyte-like).

The term a "reprogramming gene", as used herein, refers to a gene whose expression, contributes to the reprogramming of a differentiated cell, e.g. a somatic cell to an undifferentiated cell (e.g. a cell of a pluripotent state or partially pluripotent state). A reprogramming gene can be, for example, genes encoding master transcription factors Sox2, Oct3/4, Klf4, Nanog, Lin-28, c-myc and the like. The term "reprogramming factor" refers to the protein encoded by the reprogramming gene.

The term "exogenous" refers to a substance present in a cell other than its native source. The terms "exogenous" when used herein refers to a nucleic acid (e.g. a nucleic acid encoding a reprogramming transcription factor, e.g. Sox2, Oct3/4, Klf4, Nanog, Lin-28, c-myc and the like) or a protein (e.g., a transcription factor polypeptide) that has been introduced by a process involving the hand of man into a biological system such as a cell or organism in which it is not normally found or in which it is found in lower amounts. A substance (e.g. a nucleic acid encoding a sox2 transcription factor, or a protein, e.g., a SOX2 polypeptide) will be considered exogenous if it is introduced into a cell or an ancestor of the cell that inherits the substance.

The term "isolated" as used herein signifies that the cells are placed into conditions other than their natural environment. The term "isolated" does not preclude the later use of these cells thereafter in combinations or mixtures with other cells.

As used herein, the term "expanding" refers to increasing the number of like cells through cell division (mitosis). The term "proliferating" and "expanding" are used interchangeably.

As used herein, a "cell-surface marker" refers to any molecule that is expressed on the surface of a cell. Cell-surface expression usually requires that a molecule possesses a transmembrane domain. Some molecules that are normally not found on the cell-surface can be engineered by recombinant techniques to be expressed on the surface of a cell. Many naturally occurring cell-surface markers are termed "CD" or "cluster of differentiation" molecules. Cell-surface markers often provide antigenic determinants to which antibodies can bind to. A cell-surface marker of particular relevance to the methods described herein is CD34. The useful hematopoietic progenitor cells according to the present disclosure preferably express CD34 or in other words, they are CD34 positive.

A cell can be designated "positive" or "negative" for any cell-surface marker, and both such designations are useful for the practice of the methods described herein. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing flow cytometric analysis of such a contacted cell to determine whether the antibody is bound the cell. It is to be understood that while a cell may express messenger RNA for a cell-surface marker, in order to be considered positive for the methods described herein, the cell must express it on its surface. Similarly, a cell is considered "negative" for a cell-surface marker if it does not express the marker on its cell-surface in amounts sufficient to be detected using methods known to those of skill in the art, such as contacting a cell with an antibody that binds specifically to that marker and subsequently performing flow cytometric analysis of such a contacted cell to determine whether the antibody is bound the cell. In some embodiments, where agents specific for cell-surface lineage markers used, the agents can all comprise the same label or tag, such as fluorescent tag, and thus all cells positive for that label or tag can be excluded or removed, to leave uncontacted hematopoietic stem or progenitor cells for use in the methods described herein.

The term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes, i.e., T-cells.

The term "promoter/enhancer" refers to a segment of DNA which contains sequences capable of providing both promoter and enhancer functions. For example, the long terminal repeats of retroviruses contain both promoter and enhancer functions. The enhancer/promoter may be "endogenous," "exogenous," or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

A "nucleic acid," as described herein, can be RNA or DNA, and can be single or double stranded, and can be selected, for example, from a group including: nucleic acid encoding a protein of interest, for example, transcription factors and reprogramming factors described herein.

BRIEF DESCRIPTION OF THE DRAWINGS

FIG. 1A. hPSC-derived HE was cultured for additional 3 days in EHT media, then infected with library of 26 TFs. Cells were injected intrafemorally into sublethally irradiated (250 rads) NSG mice and treated with doxycycline for 2 weeks to induce transgene expression.

FIG. 1B. Engraftment of human CD45+ cells was determined by flow cytometry of BM at 12 weeks. Library (N=6), 7 TFs (N=15), and 5 TFPoly (N=8). Defined 7 TFs and 5 TFPoly confer robust engraftment of HE. The chimerism of human CD45+ population in BM was measured at 12 weeks. HE transduced with either lentiviral library of HSC-specific TFs (Library); defined set of RUNX1, ERG, SPI1, LCOR, HOXA5, HOXA9, and HOXA10 (7 TFs); defined set of RUNX1, ERG, LCOR, HOXA5, and HOXA9 in polycistronic vectors (5 TFPoly).

FIG. 1C. Multilineage contribution of donor-derived cells in BM. After 14 weeks, BM of NSG mice engrafted with TF library was analyzed for myeloid (M; CD33+), erythroid (E; GLY-A+), B-(CD19+), and T-cells (CD3+) within the human CD45+ population. Each bar represents individual recipients engrafted. From left, recipient ID #1, #5 and #6 engrafted with hiPSCs; recipient ID #2 left (L) femur and right (R) femur, recipient ID #3 left (L) femur and right (R) femur engrafted with hESCs; recipient ID #1 and #2 engrafted with CB-HSCs as a reference.

FIGS. 1D-1E. Primary transplantation of BM engrafted with 7 TF (FIG. 1D) and 5TFPoly (FIG. 1F) at 12 weeks. Human CD45+ BM of engrafted NSG was analyzed for HSCs (CD34+CD38−), nucleated erythroid (GLY-A+ SYTO60+), enucleated erythroid (GLY-A+SYTO60−), neutrophils (PECAM+CD15+), B-cells (IgM+CD19+), B progenitor cells (IgM-CD19+), Plasmacytoid lymphocytes (IgM-CD19+CD38++) and T-cells (CD3+/CD4, CD8).

FIG. 1F. Lineage distribution of myeloid (CD33+), erythroid (GLY-A+), B-cells (CD19+) and T-cells (CD3+) was shown as a bar graph of individual recipients (N=5 for 7 TFs; N=4 for 5TFPoly).

FIG. 2A. Transgene detection in engrafted cells of secondary recipients of 7 TFs.

FIG. 2B. In vivo factor-minus-one (FMO) approach of defined 7 TFs to identify any required or unnecessary factors. BM of NSG was analyzed at 8 weeks for chimerism of human CD45+ population. The absence of RUNX1 (0.33-fold, p=0.037), ERG (0.40-fold, p=0.056), LCOR (0.23-fold, p=0.020), HOXA5 (0.37-fold, p=0.056) or HOXA9 (0.26-fold, p=0.026) reduced chimerism. Lentiviral vector with GFP was used as negative control. N=6 (4 for GFP). * p<0.05.

FIGS. 2C-2D. Secondary transplantation of BM engrafted with defined 7 TFs. After 8 weeks from primary transplantation, 2,000 human CD34+ BM cells were transplanted to secondary recipients, and followed up to 8-14 weeks. Compared with primary, secondary recipients had 0.34-fold fewer HSCs (p=0.12), 0.45-fold less nucleated erythroid (p=0.30), 3.3-fold more enucleated erythroid (p=0.11), 1.6-fold more neutrophils (p=0.18), 1.1-fold more mature B-cells (p=0.42), 0.65-fold more immature B-cells (p=0.10), and 0.56-fold less T cells (p=0.18). N=3 (primary), 2 (secondary).

FIGS. 2E-2F. Phenotypic characterization of HSC-like cells in BM engrafted with 7 TF HSPCs. Human CD45+ population from BM of NSG mice engrafted with 7 TF HSPCs at 8 weeks was analyzed for human CD34 and CD38.

FIG. 2G. The population of HSCs (CD34+CD38−CD45+) was analyzed for cell-cycle state by Ki67 and DAPI. HSCs from NSG engrafted with CB-HSCs at the same time point were used as reference. N=3. The percentage of HSCs in human CD45+ BM was 0.24-fold (p=0.058) (g); G0-phase was 0.22-fold (p=0.0025); G1-phase was 2.3-fold (p=0.0052); S/G2/M was 2.5-fold (p=0.013) vs CB equivalents (h). * p<0.01; ** p<0.05.

FIG. 3A. Globin switching in engrafted erythroid cells. Human GLY-A+ cells were isolated from lysed BM (to exclude enucleated cells) of NSG engrafted with 7 TF HSPCs at 8 weeks and analyzed by qRT-PCR to relatively quantify HBE, HBG and HBB transcripts. Cytospin image of isolated GLY-A+ cells are shown. CB; GLY-A+ erythroid cells from CB-engrafted in NSG BM, 7 TF HSPCs; GLY-A+ erythroid cells from 7 TF HSPC-engrafted in NSG BM, 5F; GLY-A+ erythroid cells from hPSCs transduced with ERG, RORA, HOXA9, SOX4 and MYB17.

FIG. 3B. Enucleation of engrafted erythroid cells. BM of NSG mice engrafted with defined 7 TF HSPCs at 8 weeks time point was analyzed for human GLY-A and SYTO60. Cytospin images of RBCs from GLY-A+ populations separated by SYTO60 nuclear staining. Cells were isolated from unlysed BM of NSG engrafted with 7 TF HSPCs. Examples of nucleated and enucleated RBCs were shown. N=3.

FIG. 3C. Phenotyping of neutrophils. Human CD45+ population from BM of NSG mice engrafted with defined 7 TF HSPCs at 8 weeks was analyzed for human PECAM and CD15. Myeloperoxidase activity of isolated CD45+ PECAM+CD15+ neutrophils was measured with or without PMA stimulation. Neutrophils from NSG engrafted with CB-HSCs were used as reference. The basal level of MPO of HE was 0.40-fold less than CB (p=0.036). PMA stimulation increased MPO production 2.5-fold (p=0.010) (CB) and 3.0-fold (p=0.10) (7 TF). Stimulated MPO production of 7 TF was 0.47-fold (0.049) vs CB. * p<0.05. Data are from 2 independent experiments with 3 technical replicates each time.

FIGS. 3D-3E. Measuring production of Ig in serum. Serum was isolated from NSG mice engrafted with CB-HSCs or defined 7 TF HSPCs at 8 weeks (IgM) (FIG. 3D) and 14 weeks (IgG) (FIG. 3E). Production of IgM and IgG (ng/mL serum) was measured by ELISA. Serum from mock transplant and NSG engrafted with CB-HSCs was used as reference. The production of both human IgM and IgG was detected and boosted by OVA in 7 TF HSPCs. * p<0.05. Data are from 2 independent experiments with 3 technical replicates each time.

FIG. 3F. Human CD3+ cells were isolated from BM of NSG mice engrafted with CB-HSCs and defined 7 TF HSPCs at 8 weeks and cultured with or without PMA/Ionomycin stimulation for 6 hours, when production of IFNγ was measured by ELISA. CD3+ T-cells from NSG engrafted with CB-HSCs were used as reference. The basal level of IFNγ of HE was 0.53-fold (p=0.073) vs CB. PMA stimulation increased IFNγ production 4.4-fold (p=0.17) (CB) and 3.0-fold (p=0.16) (HE). Stimulated IFNγ production of HE was 0.36-fold (0.039) vs CB. IFNγ production from CB-HSCs and HE themselves were shown as reference. * p<0.05. Data are from 2 independent experiments with 3 technical replicates each time.

FIG. 3G. Flow cytometric phenotyping of T-cells from engrafted 7 TF HSPCs. BM and thymus were collected at 8 weeks and analyzed for T cell markers (CD4, CD8, CD3, TCRαβ and TCRγδ). TCR phenotyping of the CD3+ population was shown. One out of 3 recipients showed the presence of TCRγδ. N=3.

FIG. 3H. TCR rearrangement of T-cells showed clonal diversity in hiPSC-derived cells. Human CD3+ thymocytes of NSG mice engrafted with defined 7 TF HSPCs at 8 weeks was analyzed to detect TCR rearrangement by Immuno-seq. CD3+ Thymocytes from CB CD34+-engrafted NSG were used as a reference.

DETAILED DESCRIPTION

Figure 1A:
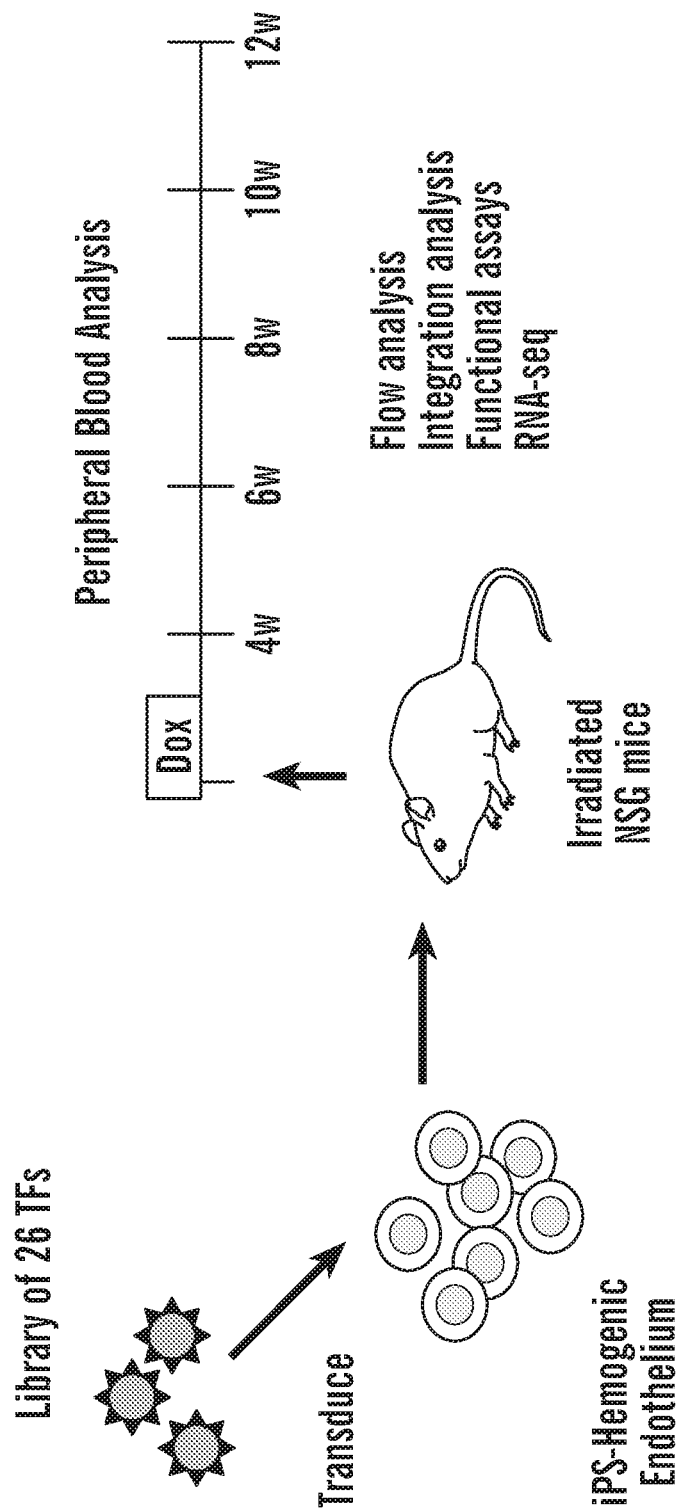
FIGS. 1A-1F collectively demonstrate the in vivo screening of TFs confers functional hematopoiesis.

Unless otherwise explained, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The terminology used herein is for the purpose of describing particular embodiments only, and is not intended to limit the scope of the embodiments of the present disclosure, which is defined solely by the claims.

Definitions of common terms in molecular biology can be found in The Merck Manual of Diagnosis and Therapy, 19th Edition, published by Merck Sharp & Dohme Corp., 2011 (ISBN 978-0-911910-19-3), (2015 digital online edition at the website of Merck Manuals), Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the embodiments of the present disclosure were performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that embodiments of the present disclosure are not limited to the particular methodology, protocols, and reagents, etc., described herein and as such may vary. The terminology used herein is for the purpose of describing particular embodiments only, and is not intended to limit the scope of the embodiments of the present disclosure, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the embodiments of the present disclosure. These publications are provided solely for their disclosure prior to the filing date of the present application. Nothing in this regard should be construed as an admission that the inventors are not entitled to antedate such disclosure by virtue of prior embodiments of the present disclosure or for any other reason. All statements as to the date or representation as to the contents of these documents is based on the information available to the applicants and does not constitute any admission as to the correctness of the dates or contents of these documents.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

The disclosure described herein does not concern the destruction of a human embryo.

There is no one well tested and reliable method of producing HSCs and HSPCs from PSCs where these HSCs and HSPCs have all the hematopoietic lineage potentials and would engraft and reconstitute in vivo. i.e., multi-lineage HSCs and HSPCs that capable of producing blood cells in vivo. The disclosure seeks to provide improved PSCs-derived HSCs and HSPCs that exhibit long-term multilineage hematopoiesis in vivo after implantation in a host subject. For example, long-term multilineage hematopoiesis in vivo for at least 12 weeks or longer after implantation.

A variety of tissue lineages can be derived in vitro by stepwise exposure of pluripotent stem cells (PSCs) to morphogens in an attempt to mimic embryonic development[1], or by conversion of one differentiated cell type directly into another by enforced expression of master transcription factors (TFs)[2]. Despite considerable effort, neither approach has yielded functional human hematopoietic stem cells (HSCs). Building upon recent evidence that HSCs derive from definitive hemogenic endothelium (HE)[3-9], the inventors performed morphogen-directed differentiation of human PSCs into HE followed by combinatorial screening of 26 candidate HSC-specifying TFs for the potential to promote hematopoietic engraftment in irradiated immune deficient murine hosts. The inventors recovered seven TFs (ERG, HOXA5, HOXA9, HOXA10, LCOR, RUNX1, SPI1) that together were sufficient to convert HE into hematopoietic stem and progenitor cells (HSPCs) that engraft primary and secondary murine recipients with myeloid cells, beta globin-expressing erythrocytes, IgM+/CD19+ B-cells, and αβ and γδ T-cells. Five TFs, ERG, HOXA5, HOXA9, LCOR, and RUNX1, are the minimum TFs necessary to convert HE into HSPCs. Integration analysis of virally-transduced transgenes detected common clones in myeloid and lymphoid lineages, indicating derivation of HSC-like cells from PSCs. This combined approach of morphogen-driven differentiation and TF-mediated cell fate conversion from PSCs yields HSPCs that hold promise for modeling hematopoietic disease in humanized mice and for therapeutic strategies in genetic blood disorders.

Described herein, the inventors demonstrated a process of making PSCs-derived HSCs and HSPCs that would differentiate into all the hematopoietic lineage potentials and would also engraft well in the host after transplantation so that there is sufficient engrafted cells to sustain blood production in vivo. This method produces functionally relevant HSCs and HSPCs in sufficient quantities for both meaningful experimental and therapeutic purposes. For example, in vitro experiments, these PSCs-derived HSCs and HSPCs can be differentiated to the desired hematopoietic lineage, e.g., erythroid cells, lymphoid cells, and myeloid cells, for further studies. For example, in in vivo studies, these PSCs-derived HSCs and HSPCs would engraft in the host, and differentiate into the variety of hematopoietic progeny cells, and reconstitute and populate the circulatory and immune system of the host.

Embodiments of the present disclosure are based, in part, to the discovery of that transcription factors, ERG, HOXA5, HOXA9, LCOR, RUNX1, HOXA10, and SPI1, would bring about the differentiation of HSCs and HSPCs from PSC-derived hemogenic endothelia cells (HE). First, the inventors showed that embryonic bodies (EB) are made from pluripotent stem cells, e.g., including induced pluripotent cells. Second, the HE are harvested from the EB. Then, the HE cells are induced to undergo EHT and subsequently transfected with exogenous copies of at least the following transcription factors: ERG, HOXA9, HOXA5, LCOR and RUNX1, to promote differentiation of the HE into HSCs and HSPCs that exhibit all the hematopoietic lineage potentials. These multi-lineage HSCs and HSPCs engraft in recipient host after implantation and made all kinds of blood cells in vivo after implantation.

Accordingly, in one aspect, provided herein is a method for making HSCs and HSPCs comprising in vitro transfecting hemogenic endothelia cells (HE) with an exogenous gene coding copy of each of the following transcription factors ERG, HOXA9, HOXA5, LCOR and RUNX1, wherein the transcription factors are expressed in the transfected cells to produce a population of multilineage HSCs and HSPCs that engrafts in recipient host after implantation.

In another aspect, this disclosure provides is a method of making HSCs and HSPCs comprising (a) generating EB from PSCs; (b) isolating hemogenic endothelia cells (HE) from the resultant population of EB; (c) inducing EHT in culture in the isolated HE in order to obtain hematopoietic stem cells, and (d) in vitro transfecting the induced HE with an exogenous gene coding copy of each of the following transcription factors ERG, HOXA9, HOXA5, LCOR and RUNX1, wherein the transcription factors are expressed in the transfected cells to produce a population of multilineage HSCs and HSPCs. In one embodiment, the method further comprises selecting EBs that are generated from the PSCs, prior to isolating the HE. In one embodiment, the HE is isolated from the selected EBs.

In some aspects, this disclosure provides methods for enhancing or improving the in vivo engraftment, or reconstitution, or both of hematopoietic related cells that have been implanted into a subject. In one embodiment, the method comprises providing populations of multilineage HSCs and HSPCs that have an exogenous gene coding copy of each of the following transcription factors ERG, HOXA9, HOXA5, LCOR and RUNX1, and optionally an exogenous gene coding copy of the transcription factors HOXA10, and SPI1, and implanting into a host subject. In one embodiment, the multilineage HSCs and HSPCs further comprise and an exogenous gene coding copy of each of the following reprogramming factors OCT4, SOX2, KLF4 and optionally c-MYC or nanog and LIN28. In another embodiment, the method comprises making HSCs and HSPCs by any one method in this disclosure and implanting into a host subject. In one embodiment, the subject donates some mature cells from which iPSCs are induced. From the iPSCs, EBs are induced from which HEs are isolated and induced to EHT, followed by the transfection of transcription factor genes to produce HSCs and HSPCs. These HSCs and HSPCs are then implanted back into the donor subject, wherein the donor and recipient is the subject. In one embodiment, a donor subject donates some mature cells from which iPSCs are induced. From the iPSCs, EBs are induced from which HEs are isolated and induced to EHT, followed by the transfection of transcription factor genes to produce HSCs and HSPCs. These HSCs and HSPCs are then implanted back into a recipient subject, wherein the donor and recipient are two different subjects.

In some aspects, this disclosure provides compositions of modified (also referred to as engineered) cells for use in in vivo cellular replacement therapy, for the manufacture of medicament for treatment of hematological diseases, blood disorders, hematopoietic disorders, and for in vitro studies of disease modeling, drug screening, and hematological diseases. In one embodiment, the engineered cells are multilineage HSCs and HSPCs that have an exogenous gene coding copy of each of the following transcription factors ERG, HOXA9, HOXA5, LCOR and RUNX1, and optionally also contain an exogenous gene coding copy of the transcription factors HOXA10, and SPI1. In one embodiment, the engineered cells are multilineage HSCs and HSPCs that further comprise an exogenous gene coding copy of each of the following reprogramming factors OCT4, SOX2, KLF4 and optionally c-MYC or NANOG and LIN28. In another embodiment, the engineered cells are HSCs and HSPCs made by any one method described in this disclosure. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is an engineered cell derived from a population of HE that is produced by a method comprising (a) generating EB from PSCs; (b) isolating HE from the resultant population of EB; (c) inducing EHT in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. In one embodiment, the method further comprises selecting EBs that are generated from the PSCs, prior to isolating the HE. In one embodiment, the HE is isolated from the selected EBs. In another embodiment, the population of HE is further transfected with an exogenous gene coding copy of the transcription factors HOXA10, and SPI1. In one embodiment, the engineered cells are the multilineage HSCs and HSPCs are produced from the resultant transfection of the described TFs. In one embodiment, the engineered cell further comprise an exogenous gene coding copy of each of the following reprogramming factors OCT4, SOX2, KLF4 and optionally c-MYC or NANOG and LIN28. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is an engineered cell derived from a population of HE that is produced by a method comprising in vitro transfecting the population of HE with an exogenous gene coding copy of each of the following transcription factors ERG, HOXA9, HOXA5, LCOR and RUNX1. In another embodiment, the population of HE is further transfected with an exogenous gene coding copy of the transcription factors HOXA10, and SPI1. In one embodiment, the engineered cells are the multilineage HSCs and HSPCs are produced from the resultant transfection of the described TFs. In one embodiment, the engineered cell further comprise an exogenous gene coding copy of each of the following reprogramming factors OCT4, SOX2, KLF4 and optionally c-MYC or NANOG and LIN28. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is an engineered cell comprises an exogenous copy of each of the following transcription factors ERG, HOXA9, HOXA5, LCOR and RUNX1. In another embodiment, the engineered cell further comprises an exogenous gene coding copy of the transcription factors HOXA10, and SPI1. In one embodiment, the engineered cell further comprise an exogenous gene coding copy of each of the following reprogramming factors OCT4, SOX2, KLF4 and optionally c-MYC or NANOG and LIN28. In another embodiment, the engineered cells are HSCs and HSPCs made by any one method described in this disclosure. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a composition comprising a population of engineered cells derived from a population of HE and produced by a method comprising (a) generating embryonic bodies (EB) from pluripotent stem cells; (b) isolating hemogenic endothelia cells (HE) from the resultant population of EB; (c) inducing EHT in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. In one embodiment, the population of HE is further transfected with an exogenous gene coding copy of the transcription factors HOXA10, and SPI1. In one embodiment, the engineered cells are the multilineage HSCs and HSPCs are produced from the resultant transfection of the described TFs. In one embodiment, the engineered cell further comprise an exogenous gene coding copy of each of the following reprogramming factors OCT4, SOX2, KLF4 and optionally c-MYC or NANOG and LIN28. In one embodiment, the engineered cells are CD34+. In another embodiment, the engineered cells are CD34+ and CD45+. In another embodiment, the engineered cells are CD34+, CD45+, and CD38 negative. In some embodiments, this composition is useful for cellular replacement therapy in a subject.

In another aspect, this disclosure provides is a composition comprising a population of engineered cells derived from a population of HE and produced by a method comprising in vitro transfecting the population of HE with an exogenous gene coding copy of each of the following transcription factors ERG, HOXA9, HOXA5, LCOR and RUNX1. In one embodiment, the population of HE is further transfected with an exogenous gene coding copy of the transcription factors HOXA10, and SPI1. In another embodiment, the engineered cells are HSCs and HSPCs made by any one method described in this disclosure. In one embodiment, the engineered cells are CD34+. In another embodiment, the engineered cells are CD34+ and CD45+. In another embodiment, the engineered cells are CD34+, CD45+, and CD38 negative. In some embodiments, this composition is useful for cellular replacement therapy in a subject, and for in vitro studies of disease modeling, drug screening, and hematological diseases.

In another aspect, this disclosure provides is a composition comprising a population of engineered cells wherein the cells comprise an exogenous gene coding copy of each of the following transcription factors ERG, HOXA9, HOXA5, LCOR and RUNX1. In one embodiment, the cells further comprise an exogenous gene coding copy of the transcription factors HOXA10, and SPI1. In another embodiment, the engineered cells are HSCs and HSPCs made by any one method described in this disclosure. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a pharmaceutical composition comprising a population of engineered cells derived from a population of HE and a pharmaceutically acceptable carrier, wherein the engineered cells are produced by a method comprising (a) generating EB from PSCs; (b) isolating HE from the resultant population of EB; (c) inducing EHT in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. In one embodiment, the population of HE is further transfected with an exogenous gene coding copy of the transcription factors HOXA10, and SPI1. In one embodiment, the engineered cells are CD34+. In another embodiment, the engineered cells are CD34+ and CD45+. In another embodiment, the engineered cells are CD34+, CD45+, and CD38 negative. In some embodiments, this pharmaceutical composition is useful for cellular replacement therapy in a subject.

In another aspect, this disclosure provides is a pharmaceutical composition comprising a population of engineered cells derived from a population of HE and a pharmaceutically acceptable carrier, wherein the engineered cells are produced by a method comprising in vitro transfecting the population of HE with an exogenous gene coding copy of each of the following transcription factors ERG, HOXA9, HOXA5, LCOR and RUNX1. In one embodiment, the population of HE is further transfected with an exogenous gene coding copy of the transcription factors HOXA10, and SPI1. In one embodiment, the engineered cells are CD34+. In another embodiment, the engineered cells are CD34+ and CD45+. In another embodiment, the engineered cells are CD34+, CD45+, and CD38 negative. In some embodiments, this pharmaceutical composition is useful for cellular replacement therapy in a subject.

In another aspect, this disclosure provides is a pharmaceutical composition comprising a population of engineered cells and a pharmaceutically acceptable carrier, wherein the engineered cells comprise an exogenous gene coding copy of each of the following transcription factors ERG, HOXA9, HOXA5, LCOR and RUNX1. In one embodiment, the engineered cells further comprise an exogenous gene coding copy of the transcription factors HOXA10, and SPI1. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a method of cellular replacement therapy in a subject in need thereof, the method comprising administering a therapeutically effective amount of a population of engineered cells to a recipient subject, the population of engineered cells are produced by a method comprising (a) generating EB from PSCs; (b) isolating HE from the resultant population of EB; (c) inducing ENT in culture in the isolated HE in order to obtain hematopoietic stem cells, and (d) in vitro transfecting the population of HE with an exogenous gene coding copy of each of the following transcription factors ERG, HOXA9, HOXA5, LCOR and RUNX1. In one embodiment, the population of HE is further transfected with an exogenous gene coding copy of the transcription factors HOXA10, and SPI1. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a method of cellular replacement therapy in a subject in need thereof, the method comprising administering a therapeutically effective amount of a population of engineered cells to a recipient subject, the population of engineered cells are produced by a method comprising in vitro transfecting the population of HE with an exogenous gene coding copy of each of the following transcription factors ERG, HOXA9, HOXA5, LCOR and RUNX1. In one embodiment, the population of HE is further transfected with an exogenous gene coding copy of the transcription factors HOXA10, and SPI1. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a method of cellular replacement therapy in a subject in need thereof, the method comprising administering a therapeutically effective amount of a population of engineered cells to a recipient subject, the population of engineered cells comprise an exogenous gene coding copy of each of the following transcription factors ERG, HOXA9, HOXA5, LCOR and RUNX1. In one embodiment, the engineered cells further comprise an exogenous gene coding copy of the transcription factors HOXA10, and SPI1. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides engineered cells derived from a population of HE and produced by a method described herein. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a composition comprising a population of engineered cells described herein. In one embodiment, the engineered cells are multi-lineage HSCs and HSPCs are produced from the resultant transfection of the described TFs. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a pharmaceutical composition comprising a population of engineered cells described herein and a pharmaceutically acceptable carrier. In one embodiment, the engineered cells are CD34+. In another embodiment, the engineered cells are CD34+ and CD45+. In another embodiment, the engineered cells are CD34+, CD45+, and CD38 negative.

In another aspect, this disclosure provides is a pharmaceutical composition described herein for use in cellular replacement therapy in a subject.

In another aspect, this disclosure provides is a method of cellular replacement therapy in a subject in need thereof, the method comprising administering a therapeutically effective amount of a population of engineered cells described, or a composition described, or a pharmaceutical composition described to a recipient subject.

In one embodiment of any one aspect described, the method of generating HSCs and HSPCs described is an in vitro or ex vivo method.

In one embodiment of any one method, engineered cell, or composition described, the multilineage hematopoietic progenitor cells are generated by introducing in vitro or ex vivo each of the following transcription factors ERG, HOXA9, HOXA5, LCOR and RUNX1, in the HE cells derived from PSC-induced EBs. For example, by transfecting with a vector or more, the vector(s) collectively carry an exogenous gene coding copy of each of the following transcription factors, ERG, HOXA9, HOXA5, LCOR and RUNX1, for in vivo expression of the transcription factor in the transfected cells.

In one embodiment of any one method, engineered cell, or composition described, the multilineage hematopoietic progenitor cells are generated by contacting a population of HEs with a vector or more, wherein the vector(s) collectively carrying an exogenous gene coding copy of each of the following transcription factors, ERG, HOXA9, HOXA5, LCOR and RUNX1, for the in vivo expression of the factors in the contacted cells, and wherein the transfected transcription factors are expressed in vivo in the contacted cells.

In one embodiment of any one method, engineered cell, or composition described, the method further comprising in vitro transfecting the HE with an exogenous gene coding copy of the transcription factor, HOXA10, wherein the transfected transcription factor is expressed in vivo in the transfected cells.

In one embodiment of any one method, engineered cell, or composition described, the method further comprising in vitro transfecting the HE with an exogenous gene coding copy of the transcription factor, SPI1, wherein the transfected transcription factor is expressed in vivo in the transfected cells.

In one embodiment of any one method, engineered cell, or composition described, the method further comprising in vitro transfecting the HE with an exogenous gene coding copy of the transcription factors, HOXA10 and SPI1, wherein the transfected transcription factors are expressed in vivo in the transfected cells.

In one embodiment of any one method, engineered cell, or composition described, the engineered cell of this disclosure is a mammalian cell.

In one embodiment of any one method, engineered cell, or composition described, the engineered mammalian cell is a primate cell.

In one embodiment of any one method, engineered cell, or composition described, the engineered primate cell is a human cell.

In one embodiment of any one method, engineered cell, or composition described, the engineered cell is CD34+.

In another embodiment of any one method, engineered cell, or composition described, the engineered cell is CD34+ and CD45+.

In another embodiment of any one method, engineered cell, or composition described, the engineered cell is CD34+, CD45+, and CD38 negative.

In another embodiment of any one method, engineered cell, or composition described, the engineered cell has an exogenous gene of at least one of the following transcription factors: ERG, HOXA9, HOXA5, HEXA10, SPI1, LCOR and RUNX1.

In another embodiment of any one method, engineered cell, or composition described, the engineered cell has an exogenous gene of at least one of the following reprogramming factors: OCT4, SOX2, KLF4, c-MYC, NANOG, and LIN28.

In one embodiment of any one method, engineered cell, or composition described, the engineered cells disclosed herein are multilineage HSCs and HSPCs that engraft in vivo in a host recipient subject and produce blood cells in vivo.

In one embodiment of any one method, engineered cell, or composition described, the engineered cells disclosed herein are multilineage HSCs and HSPCs that reconstitutes the hematopoietic system in vivo when transplanted into a host recipient subject.

In one embodiment of any one method, engineered cell, or composition described, the engineered cells disclosed herein are multilineage HSCs and HSPCs that differentiate to myeloid cells in vivo, and the myeloid cells produce MPO upon PMA or cytokine stimulation in vivo.

In one embodiment of any one method, engineered cell, or composition described, the engineered cells disclosed herein are multilineage HSCs and HSPCs that differentiate to functional T- and B-cells in vivo, the functional T- and B-cells produce IgM and IgG. The functional T- and B-cells also undergo immunoglobulin class switching in response to ovalbumin stimulation. The functional T- and B-cells also produces INF-γ.

In one embodiment of any one method, engineered cell, or composition described, the engineered cells produce blood cells in vivo when engrafted in vivo in a host recipient subject.

In one embodiment of any one method, engineered cell, or composition described, the engineered cells reconstitutes the hematopoietic system in vivo when transplanted into a host recipient subject.

In one embodiment of any one method, engineered cell, or composition described, the engineered cells differentiate to myeloid cells in vivo, and the myeloid cells produce MPO upon PMA or cytokine stimulation in vivo.

In one embodiment of any one method, engineered cell, or composition described, the engineered cells differentiate to functional immune cells in vivo, e.g., T- and B-cells, wherein the functional immune cells produce IgM and IgG. The functional immune cells also undergo immunoglobulin class switching in response to ovalbumin stimulation. The functional immune cells also produce INF-γ.

In one embodiment of any one method, engineered cell, or composition described, the HE cells are cells that are derived from embryoid bodies (EBs) obtained from a population of pluripotent stem cells (PSC). In one embodiment, the HE are definitive HE.

In one embodiment of any one method, engineered cell, or composition described, the population of PSC is induced pluripotent stem cells (iPSc) or embryonic stem cells (ESC).

In one embodiment of any one method, engineered cell, or composition described, the PSC are human PSC or mouse PSC.

In one embodiment of any one method, engineered cell, or composition described, the iPSCs are produced by in vitro or ex vivo introducing exogenous copies of only three reprogramming factors OCT4, SOX2, and KLF4 into mature cells.

In one embodiment of any one method, engineered cell, or composition described, the iPSC having exogenous copies of OCT4, SOX2, and KLF4 is further introduced in vitro or ex vivo with an exogenous copy of c-MYC into the cells.

In one embodiment of any one method, engineered cell, or composition described, the iPSC having exogenous copies of OCT4, SOX2, and KLF4 is further introduced in vitro or ex vivo with an exogenous copies of NANOG and LIN28 into the cells.

In one embodiment of any one method, engineered cell, or composition described, the iPSC are produced by introducing in vitro or ex vivo exogenous copies of reprogramming factors OCT4, SOX2, and KLF4, and optionally with c-MYC or NANOG and LIN28 into the mature cells.

In one embodiment of any one method, engineered cell, or composition described, the iPSC are produced by in vitro or ex vivo contacting the mature cells with a vector or more, wherein the vector(s) collectively carry exogenous copies of reprogramming factors OCT4, SOX2, and KLF4, and optionally with c-MYC or NANOG and LIN28 into mature cells, and wherein the reprogramming factors are expressed in vivo in the contacted mature cells.

In one embodiment of any one method, engineered cell, or composition described, the mature cells from which iPSC are made can be from any cell type in a donor subject. For examples, cells from a blood sample, or bone marrow sample, B lymphocytes (B-cells), T lymphocytes, (T-cells), fibroblasts, keratinocytes etc. In some embodiments, any mature cell type from the donor subject can be used except a cell with no nucleus, such as a human red blood cell.

In one embodiment of any one method, engineered cell, or composition described, the iPSC are produced by in vitro or ex vivo introducing the disclosed reprogramming factors two or more times into the mature cells.

In one embodiment of any one method, engineered cell, or composition described, the iPSC are produced by in vitro or ex vivo contacting the mature cells with the disclosed vector(s) factors two or more times into the mature cells.

In one embodiment of any one method, engineered cell, or composition described, the mature cells from which iPSC are made are mammalian cells.

In one embodiment of any one method, engineered cell, or composition described, the mature cells from which iPSC are made are primate cells.

In one embodiment of any one method, engineered cell, or composition described, the mature cells from which iPSC are made are human cells.

In one embodiment of any one method, engineered cell, or composition described, the mature cells from which iPSC are made are autologous to a recipient subject who would be receiving the engineered cells that are derived from the mature cells according to any one of the methods described in this disclosure.

In one embodiment of any one method, engineered cell, or composition described, the mature cells from which iPSC are made are HLA matched with a recipient subject who would be receiving the engineered cells that are derived from the mature cells according to any one of the methods described in this disclosure.

In one embodiment of any one engineered cell or composition described, the pharmacological acceptable carrier is not cell culture media.

In one embodiment of any one composition described, the pharmacological composition is a cryopreserved composition comprising at least one cryopreservative agent known in the art. For examples, dimethyl sulphoxide (DMSO), poly-vinylpyrrolidone (PVP), fetal calf serum (FCS), polyethylene glycol (PEG), glycerol, ethylene glycol (EG) and trehalose. Combinations of two or more cryopreservative agents can be used.

Pluripotent Stem Cells for Generating Embryonic Bodies, HE, and HSC and HSPC.

Pluripotent stem cells (PSCs) have the potential to give rise to all the somatic tissues. Directed differentiation of PSCs aims to recapitulate embryonic development to generate patient-matched tissues by specifying the three germ layers. A common theme in directed differentiation across all germ layers is the propensity of PSCs to give rise to embryonic- and fetal-like cell types, which poses a problem for integration and function in an adult recipient. This distinction is particularly striking in the hematopoietic system, which emerges in temporally and spatially separated waves at during ontogeny (Dzierzak and Speck, 2008). The earliest "primitive" progenitors emerge in the yolk sac at 8.5 dpc and give rise to a limited repertoire of macrophages, megakaryocytes and nucleat-ed erythrocytes (Baron et al 2005, Tavian and Peault 2005, Ferkowicz et al 2005). These early embryonic-like progenitors are generally myeloid-based and cannot functionally repopulate the bone marrow of adult recipients. By contrast, "definitive" cells with hematopoietic stem cell (HSC) potential emerge later in arterial endothelium within the aorta-gonad-mesonephros (AGM) and other anatomical sites (Dzierzak and Speck, 2008). Directed differentiation of PSCs gives rise to hematopoietic progenitors, which resemble those found in the yolk sac of the early embryo. These lack functional reconstitution potential, are biased to myeloid lineages, and express embryonic globins.

In one embodiment of any one aspect described, the population of PSC used for generating EBs is induced pluripotent stem cells (iPS cells) or embryonic stem cells (ESC).

In one embodiment of any one aspect described, the iPS cells are produced by introducing only reprogramming factors OCT4, SOX2, KLF4 and optionally c-MYC or NANOG and LIN28 into mature cells.

In one embodiment of any one aspect described, the mature cells for producing iPS cells are selected from the group consisting of B lymphocytes (B-cells), T lymphocytes, (T-cells), fibroblasts, and keratinocytes.

In one embodiment of any one aspect described, the iPSCs are produced by introducing the reprogramming factors two or more times into the mature cells.

Induced Pluripotent Stem Cells

In some embodiments, the pluripotent stem cells (PSCs) described herein are derived from isolated induced pluripotent stem cells (iPSCs). An advantage of using iPSCs is that the cells can be derived from the same subject to which the eventual immune cells would be reintroduced. That is, a somatic cell can be obtained from a subject, reprogrammed to an induced pluripotent stem cell, and then transfected and differentiated into a modified immune cell to be administered to the subject (e.g., autologous cells). Since the progenitors are essentially derived from an autologous source, the risk of engraftment rejection or allergic responses is reduced compared to the use of cells from another subject or group of subjects. In some embodiments, the cells for generating iPSCs are derived from non-autologous sources. In addition, the use of iPSCs negates the need for cells obtained from an embryonic source. Thus, in one embodiment, the PSCs used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, and epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a common myeloid stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed embodiments of the present disclosure. Thus, any method that re-programs a somatic cell to the pluripotent phenotype would be appropriate for use in the methods described herein.

Reprogramming methodologies for generating pluripotent cells using defined combinations of transcription factors have been described to induced pluripotent stem cells from somatic cells. Yamanaka and Takahashi converted mouse somatic cells to ES cell-like cells with expanded developmental potential by the direct transduction of Oct4, Sox2, Klf4, and optionally c-Myc. See U.S. Pat. Nos. 8,058,065 and 9,045,738 to Yamanaka and Takahashi. iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission, and tetraploid complementation.

Subsequent studies have shown that human iPS cells can be obtained using similar transduction methods, and the transcription factor trio, OCT4, SOX2, and NANOG, has been established as the core set of transcription factors that govern pluripotency. The production of iPS cells can be achieved by the introduction of nucleic acid sequences encoding stem cell-associated genes into an adult, somatic cell, using viral vectors. In general, retrovirus- or adenovirus-based vectors are used to deliver the desired gene/nucleic acid. Other viruses used as vectors include adeno-associated viruses, lentiviruses, pox viruses, alphaviruses, and herpes viruses.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30, this reference is incorporated herein by reference in its entirety.). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, l-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. This reference is incorporated herein by reference in its entirety. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Daxl, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Many US Patents and Patent Application Publications teach and describe methods of generating iPSCs and related subject matter. For examples, U.S. Pat. Nos. 9,347,044, 9,347,042, 9,347,045, 9,340,775, 9,341,625, 9,340,772, 9,250,230, 9,132,152, 9,045,738, 9,005,975, 9,005,976, 8,927,277, 8,993,329, 8,900,871, 8,852,941, 8,802,438, 8,691,574, 8,735,150, 8,765,470, 8,058,065, 8,048,675, and US Patent Publication Nos: 20090227032, 20100210014, 20110250692, 20110201110, 20110200568, 20110306516, 20100021437, 20110256626, 20110044961, 20120276070, 20120263689, 20120128655, 20120100568, 20130295064, 20130029866, 20130189786, 20130295579, 20130130387, 20130157365, 20140234973, 20140227736, 20140093486, 20140301988, 20140170746, 20140178989, 20140349401, 20140065227, and 20150140662. These references are incorporated herein by reference in their entirety.

Somatic Cells for Reprogramming

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, skin, immune cells, hepatic, splenic, lung, peripheral circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of thyroid progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Daxl; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fth117; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1;

GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Embryonic Bodies (EBs) from Pluripotent Stem Cells

In one embodiment of any one aspect described, the EB are generated or induced from PSCs, for example, iPSCs or embryonic stem cells (ESCs) derived from the blastocyst stage of embryos from mouse (mESC), primate, and human (hESC) sources.

EBs are three-dimensional aggregates of pluripotent stem cells produced and cultured in vitro in the presence of serum. EBs largely exhibit heterogeneous patterns of differentiated cell types, generating a mixture of primitive and definitive hematopoietic progenitor cell types. Primitive progenitors equate to those that arise in vivo naturally in the earliest stages of embryonic development, whereas at later stages of maturation the embryonic populations give rise to definitive progenitors cells, which behave similarly to the cells typical of adult hematopoiesis.

EB formation is often used as a method for initiating spontaneous differentiation toward the three germ lineages. EB differentiation begins with the specification of the exterior cells toward the primitive endoderm phenotype. The cells at the exterior then deposit extracellular matrix (ECM), containing collagen IV and laminin, similar to the composition and structure of basement membrane. In response to the ECM deposition, EBs often form a cystic cavity, whereby the cells in contact with the basement membrane remain viable and those at the interior undergo apoptosis, resulting in a fluid-filled cavity surrounded by cells. Subsequent differentiation proceeds to form derivatives of the three germ lineages. In the absence of supplements, the "default" differentiation of ESCs is largely toward ectoderm, and subsequent neural lineages. However, alternative media compositions, including the use of fetal bovine serum as well as defined growth factor additives, have been developed to promote the differentiation toward mesoderm and endoderm lineages.

As a result of the three-dimensional EB structure, complex morphogenesis occurs during EB differentiation, including the appearance of both epithelial- and mesenchymal-like cell populations, as well as the appearance of markers associated with the epithelial-mesenchymal transition (EMT). Additionally, the inductive effects resulting from signaling between cell populations in EBs results in spatially and temporally defined changes, which promote complex morphogenesis. Tissue-like structures are often exhibited within EBs, including the appearance of blood islands reminiscent of early blood vessel structures in the developing embryo, as well as the patterning of neurite extensions (indicative of neuron organization) and spontaneous contractile activity (indicative of cardiomyocyte differentiation) when EBs are plated onto adhesive substrates such as gelatin. More recently, complex structures, including optic cup-like structures were created in vitro resulting from EB differentiation.

A non-limited method for producing EBs from iPSC is as follows. Human iPSCs were differentiated as EBs in the presence of BMP4 and cytokines, as previously described (Chadwick et al., 2003, Blood, 102:906-915). Briefly, iPSC colonies were scraped into non-adherent rotating 10 cm plates. EB media was KO-DMEM+20% FBS (Stem Cell Technologies), 1 mM L-glutamine, 1 mM NEAA, penicillin/streptomycin, 0.1 mM β-mercaptoethanol, 200 µg/ml h-transferrin, and 50 µg/ml ascorbic acid. After 24 hrs, media was changed by allowing EBs to settle by gravity, and replaced with EB media supplemented with growth factors: 50 ng/ml BMP4 (R&D Systems), 300 ng/ml SCF, 300 ng/ml FLT3, 50 ng/ml G-CSF, 20 ng/ml IL-6, 10 ng/ml IL-3 (all Peprotech). Media was changed on day 3, 5, 8 and 10. EBs were observed by day 5. EBs can be selected and dissociated to individual cells anywhere from day 8-14 by digesting with collagenase B (Roche) for 2 hrs, followed by treatment with enzyme-free dissociation buffer (Gibco), and filtered through an 80 µm filter.

An alternative method of producing EBs from iPSC is as follows. Confluent human or mouse iPSC colonies were disrupted to small aggregates using collagenase IV (1 mg/ml, 15 minutes at 37° C.). Cell aggregates were resuspended in StemPro fully defined medium (StemPro-34 Serum-Free Media, Gibco proprietary formulation, guaranteed as animal protein-free by the manufacturer) supplemented with 0.5 ng/ml human recombinant BMP-4 (R&D Systems) at a ratio of 2 confluent ESC/iPSC wells for 1 well of differentiation. During all the differentiation process, cell attachment was prevented using low cluster tissue culture dishes (Corning Costar). On day 1 of differentiation, embryoid bodies (EB) were harvested and transferred to fresh StemPro media supplemented with 10 ng/ml BMP-4 and 5 ng/ml bFGF. After 72 hours, EB were harvested again and transferred to a medium consisting of StemPro media supplemented with 100 ng/ml human recombinant VEGF (R&D Systems), 5 ng/ml bFGF, 100 ng/ml SCF (kind gift from Amgen), 100 ng/ml FLT3-L (kind gift from Amgen) and 40 ng/ml TPO (Peprotech, UK) for 4 additional days. All differentiation steps were performed in hypoxic conditions (5% $O_2$) in a humidified incubator at 37° C. After 8 days of differentiation, EB were harvested and spun at 65 g for 4 min. Supernatants containing non-adherent cells were stored on ice and EB were disrupted using Trypsin-EDTA followed by manual disruption in FBS containing blocking medium using a 21G needle, After centrifugation, cells were resuspended in freshly prepared collagenase IV solution (0.2 mg/ml) for 30 min at 37° C. Cells were disrupted again using a 21G needle and filtered over a 70 µm cell strainer (Falcon). Supernatants from the initial centrifugation were pooled with these suspensions and magnetic bead associated cell sorting (MACS) for the CD34 epitope was performed following manufacturer's instructions (Miltenyi Biotech).

Other methods of generating EBs from ESC and iPSC are known in the art. For example, as described in U.S. Pat. Nos. 6,602,711; 7,220,584; 7,452,718; 7,648,833; 7,795,026; 7,803,619; 8,278,097, 8,501,474; and 8,986,996, the contents of each are incorporated herein by reference in its entirety.

In one embodiment of any one aspect described, the EB are generated or induced from PSCs by culturing or exposing the PSCs to morphogens for about 8 days.

In one embodiment of any one aspect described, the exposure to the morphogens is for about 5-14 days, 5-13 days, 5-12 days, 5-11 days, 5-10 days, 5-9 days, 5-8 days, 5-7 days, 5-6 days, 6-14 days, 6-13 days, 6-12 days, 6-11 days, 6-10 days, 6-9 days, 6-8 days, 6-7 days, 7-14 days, 7-13 days, 7-12 days, 7-11 days, 7-10 days, 7-9 days, 7-8 days, 8-14 days, 8-13 days, 8-12 days, 8-11 days, 8-10 days, 8-9 days, 9-14 days, 9-13 days, 9-12 days, 9-11 days, 9-10 days, 10-14 days, 10-13 days, 10-12 days, 10-11 days, 11-14 days, 11-13 days, 11-12 days, 12-14 days, 12-13 days, or 13-14 days.

In one embodiment of any one aspect described, the exposure to the morphogens of the PSCs is for about 5 days, 6 days, 7 days, 9 days, 10 days, 11 days 12 days, 13 days or 14 days.

In one embodiment of any one aspect described, the morphogens for inducing EBs formation from PSCs is/are selected from the group consisting of holo-transferrin, mono-thioglycerol (MTG), ascorbic acid, bone morphogenetic protein (BMP)-4, basic fibroblast growth factor (bFGF), SB431542, CHIR99021, vascular endothelial growth factor (VEGF), interleukin (IL)-6, insulin-like growth factor (IGF)-1, interleukin (IL)-11, stem cell factor (SCF), erythropoietin (EPO), thrombopoietin (TPO), interleukin (IL)-3, and Fms related tyrosine kinease 3 ligand (Flt-3L).

In some embodiments of any one aspect described, a combination of two or more of these morphogens are selected to generate EBs from PSCs.

In one embodiment of any one aspect described, a combination of all morphogens holo-transferrin, MTG, ascorbic acid, BMP-4, bFGF, SB431542, CHIR99021, VEGF, IL-6, IGF-1, IL-11, SCF, EPO, TPO, IL-3, and Flt-3L are used to generate EBs from PSCs.

In one embodiment of any one aspect described, the morphogens for inducing EBs formation from PSCs consist essentially of holo-transferrin, MTG, ascorbic acid, BMP-4, bFGF, SB431542, CHIR99021, VEGF, IL-6, IGF-1, IL-11, SCF, EPO, TPO, IL-3, and Flt-3L.

In one embodiment of any one aspect described, the morphogens for inducing EBs formation from PSCs consist of holo-transferrin, MTG, ascorbic acid, BMP-4, bFGF, SB431542, CHIR99021, VEGF, IL-6, IGF-1, IL-11, SCF, EPO, TPO, IL-3, and Flt-3L.

In one embodiment of any one aspect described, the method further comprises selecting EBs that are generated from the PSCs, prior to isolating HE from the selected EBs.

In one embodiment of any one aspect described, the desired EBs are less than 800 microns in size and are selected.

In other embodiments of any one aspect described, the EBs selected are less than 790 μm, less than 780 μm, less than 770 μm, less than 760 μm, less than 750 μm, less than 740 μm, less than 730 μm, less than 720 μm, less than 710 μm, less than 700 μm, less than 690 μm, less than 680 μm, less than 670 μm, less than 660 μm, less than 650 μm, less than 640 μm, less than 630 μm, less than 620 μm, less than 610 μm, less than 600 μm, less than 590 μm, less than 580 μm, less than 570 μm, less than 560 μm, less than 550 μm, less than 540 μm, less than 530 μm, less than 520 μm, less than 510 μm, less than 500 μm, less than 490 μm, less than 480 μm, less than 470 μm, less than 460 μm, less than 450 μm, less than 440 μm, less than 430 μm, less than 420 μm, less than 410 μm, less than 400 μm, less than 390 μm, less than 380 μm, less than 370 μm, less than 360 μm, less than 350 μm, less than 340 μm, less than 330 μm, less than 320 μm, less than 310 μm, less than 300 μm, less than 290 μm, less than 280 μm, less than 270 μm, less than 260 μm, less than 250 μm, less than 240 μm, less than 230 μm, less than 220 μm, less than 210 μm, less than 200 μm, less than 190 μm, less than 180 μm, less than 170 μm, less than 160 μm, less than 150 μm, less than 140 μm, less than 130 μm, less than 120 μm, less than 110 μm, or less than 100 μm in size.

In other embodiments of any one aspect described, the EBs selected are about 800 μm, about 790 μm, about 780 μm, about 770 μm, about 760 μm, about 750 μm, about 740 μm, about 730 μm, about 720 μm, about 710 μm, about 700 μm, about 690 μm, about 680 μm, about 670 μm, about 660 μm, about 650 μm, about 640 μm, about 630 μm, about 620 μm, about 610 μm, about 600 μm, about 590 μm, about 580 μm, about 570 μm, about 560 μm, about 550 μm, about 540 μm, about 530 μm, about 520 μm, about 510 μm, about 500 μm, about 490 μm, about 480 μm, about 470 μm, about 460 μm, about 450 μm, about 440 μm, about 430 μm, about 420 μm, about 410 μm, about 400 μm, about 390 μm, about 380 μm, about 370 μm, about 360 μm, about 350 μm, about 340 μm, about 330 μm, about 320 μm, about 310 μm, about 300 μm, about 290 μm, about 280 μm, about 270 μm, about 260 μm, about 250 μm, about 240 μm, about 230 μm, about 220 μm, about 210 μm, about 200 μm, about 190 μm, about 180 μm, about 170 μm, about 160 μm, about 150 μm, about 140 μm, about 130 μm, about 120 μm, about 110 μm, or about 100 μm in size.

The EB size selection can be achieved by any method known in the art. For example, by filtration through a filter with the desired pore size, e.g., a 200 μm filter. For example, selection is done visually.

In one embodiment of any one aspect described, the EB cells within the EBs selected are compactly adhered to each other and are dissociated to individual EB cells.

In one embodiment of any one aspect described, the EB cells within the EBs selected are dissociated to individual EB cells by digestion with trypsin or collagenase.

In one embodiment of any one aspect described, the EB cells of the selected EBs are dissociated to individual EB cells prior to the isolation of HE.

Hemogenic Endothelia Cells (HE) Isolated from the Dissociated Individual EB Cells Hemogenic endothelium (HE) is a special subset of endothelial cells scattered within blood vessels that can differentiate into hematopoietic cells. During embryonic development, multilineage HSCs/progenitor cells are derived from specialized endothelial cells, termed hemogenic endothelium, within the yolk sac, placenta, and aorta. The multilineage HSCs/progenitor cells responsible for the generation of all blood cell types during definitive hematopoiesis arise from hemogenic endothelium. All blood cells emerge from hemogenic endothelial-expressing cells through an endothelial-to-hematopoietic transition (EHT).

In vitro differentiation EB produces a hetergenous population of cells, including cells that are hemogenic endothelial-like. These are the HE cells that are isolated and induced to under go EHT in culture. In one embodiment of any one aspect described, the HE are isolated from the selected and dissociated EB cells.

In one embodiment of any one aspect described, the HE are isolated immediately from the selected and dissociated EB cells. In other embodiments of any one aspect described, the HEs are isolated less than three hours, less than two hours, less than one hour, less than 55 min, less than 50 min, less than 45 min, less than 40 min, less than 35 min, less than 30 min, less than 25 min, less than 20 min, less than 15 min, and less than 10 min after the dissociation of the select EBs to individual EB cells. In other embodiments of any one aspect described, the HEs are isolated within three hours, within two hours, within one hour, within 55 min, within 50 min, within 45 min, within 40 min, within 35 min, within 30 min, within 25 min, within 20 min, within 15 min, and within 10 min after the dissociation of the select EBs to individual EB cells.

In one embodiment of any one aspect described, the isolated HE are definitive HE. Definitive HE is a population that is defined by combination of surface antigen markers CD34+FLK1+CD235A−CD43−. Definitive hematopoietic stem cells (HSCs) are the cells responsible for the continuous production of all mature blood cells during the entire adult life span of an individual. Similarly, definitive HE are the cells that are responsible for the continuous production of all mature blood cells during the entire adult life span of an individual.

In one embodiment of any one aspect described, the isolated HE are FLK1+, CD34+, CD43− and CD235A−.

In one embodiment of any one aspect described, the isolated HE are Flk1+cKit+CD45−.

These are the cell surface biomarkers on the isolated HE before the endothelial-to-hematopoietic transition (EHT).

The HEs can be isolated by any method known in the art. For example, by immune-magnetic beads directed to the cell surface biomarkers that are characteristics of HEs. For example, by positive selection for FLK1+ and CD34+ cells from the dissociated individual EB cells followed by negative selection for CD43+ cells, and for CD235A+ cells from the resultant FLK1+ and CD34+ cells. FLK1+ and CD34+ cells that are CD43+ are discarded. FLK1+ and CD34+ cells that are CD235A+ are also discarded. The remaining FLK1+ and CD34+ cells are therefore CD43− and CD235A− cells, the desired HEs.

Other methods of generating HEs from ESC and iPSC are known in the art. For example, as described in U.S. Pat. No. 9,382,531, the contents of which is incorporated herein by reference in its entirety.

Endothelial-to-Hematopoietic Transition (EHT)

The endothelial to hematopoietic transition (EHT) is a key developmental event leading to the formation of blood stem and progenitor cells during embryogenesis. In embryogenesis, the development of hematopoietic cells in the embryo proceeds sequentially from mesoderm through the hemangioblast to the hemogenic endothelium (HE) and hematopoietic progenitors cells. The HE then undergoes the EHT by becoming pre-hematopoietic stem and progenitor cells (Pre-HSPC). Eventually after losing all their endothelial characteristics they become HSPC.

In vitro culture, it is possible to induce EHT in HE with certain factors and cytokines. Combination of all these factors is required for efficient achievement of EHT.

In one embodiment of any one aspect described, the EHT occurs by culturing or contacting the isolated HE in culture with thrombopoietin (TPO), interleukin (IL)-3, stem cell factor (SCF), IL-6, IL-11, insulin-like growth factor (IGF)-1, erythropoietin (EPO), vascular endothelial growth factor (VEGF), basic fibroblast growth factor (bFGF), bone morphogenetic protein (BMP)4, Fms related tyrosine kinase 3 ligand (Flt-3L), sonic hedgehog (SHH), angiotensin II, and chemical AGTR1 (angiotensin II receptor type I) blocker losartan potassium.

In one embodiment of any one aspect described, the isolated HEs are incubated in the EHT media for a period of time.

In one embodiment of any one aspect described, the incubation of the isolated HE in the EHT media is for about 3-10 days.

In one embodiment of any one aspect described, the incubation of the isolated HE in the EHT media is for about 3-9 days, 3-8 days, 3-7 days, 3-6 days, 3-5 days, 3-4 days, 4-10 days, 4-9 days, 4-8 days, 4-7 days, 4-6 days, 4-5 days, 5-10 days, 5-9 days, 5-8 days, 5-7 days, 5-8 days, 5-7 days, 5- 6 days, 6-10 days, 6-9 days, 6-8 days, 6-7 days, 7-10 days, 7-9 days, 7-8 days, 8-10 days, 8-9 days, or 9-10 days.

In one embodiment of any one aspect described, incubation of the isolated HE in the EHT media is for about 3 days, 4 days, 5 days, 6 days, 7 days, 8 days, 9 days, or 10 days.

To determine that EHT has occurred in the HE, morphological detection of round cells under microscopy was performed. In addition, FACS analysis of surface markers CD34+CD45+ is performed.

In one embodiment of any one aspect described, the isolated HE that have undergone EHT exhibit round cell morphology.

Transcription Factors that Induced Differentiation of HE to Multi-Lineage HSCs and HSPCs To specifying HSCs and HSPCs from the HE having undergone EHT, the inventors use a strategy that is defined as "respecification". Respecification combines directed differentiation with transcription-based reprogramming to re-establish HSC fate. The molecular differences between primary human HSCs and progenitors have been well characterized by gene expression profiling, providing a rational approach to introduce stem cell genes back into progenitors. The inventors were able to obtain transplantable HSC by restoring the HSC transcription factor network in the HE derived from hPSCs.

The inventors tailored transcription factor combinations for the HE. The minimally required five transcription factors: ERG, HOXA9, HOXA5, LCOR and RUNX1. Additionally, HOXA10 and SPI1 transcription factors can be used to induce differentiation of the HE to multilineage hematopoietic progenitors.

Generation of iPSCs by somatic cell reprogramming involves global epigenetic remodeling, and chromatin-modifying enzymes have been characterized as barriers or facilitators of reprogramming. Within the hematopoietic system, there are many epigenetic changes that mediate blood development during ontogeny and differentiation from HSCs to mature progeny. The progression from HSCs to differentiated progeny involves coordinated control of gene expression programs leading to the activation or repression of lineage-specific genes. The events that lead to the formation of all mature hematopoietic cells involve regulation of both gene expression and DNA recombination, mainly through the control of chromatin accessibility. HSC state is controlled by a large number of transcription factors and epigenetic modifiers. The inventors used screening strategies find additional factors that regulate of the HSC fate.

Accordingly, in one embodiment of any method, cells, or composition described herein, the multilineage hematopoietic progenitor cells are generated by introducing in vitro an exogenous gene coding copy each of the following transcription factors: ERG, HOXA9, HOXA5, LCOR and RUNX1, into the HE, the HE having undergone EHT and exhibit round cell morphology. In one embodiment, a vector is used as the transport vehicle to introduce any of the herein described exogenous gene coding copies into the HE. For example, by transfecting the HE with a vector or more, wherein the vector(s) collectively carry an exogenous gene coding copy of each of the following transcription factors, ERG, HOXA9, HOXA5, LCOR and RUNX1, for the in vivo expression of the transcription factor in the transfected cells. For example, by contacting the HE with a vector or more, wherein the vector(s) collectively carry an exogenous gene coding copy of each of the following transcription factors, ERG, HOXA9, HOXA5, LCOR and RUNX1, for the in vivo expression of the transcription factor in the contacted cells. For example, by contacting the isolated HE with a nucleic acid or more, wherein the nucleic acid (s) collectively carry an exogenous gene coding copy of each of the following transcription factors, ERG, HOXA9, HOXA5, LCOR and RUNX1, for the in vivo expression of the transcription factor in the contacted cells.

In one embodiment of any method, cells, or composition described herein, the multilineage hematopoietic progenitor cells are generated by contacting a population of HE with a vector or more, wherein the vector(s) collectively carrying an exogenous gene coding copy of each of the following transcription factors, ERG, HOXA9, HOXA5, LCOR and RUNX1, for the in vivo expression of the factors in the contacted cells, and wherein the transfected transcription factors are expressed in vivo in the contacted cells. The contacting is in vitro or ex vivo.

In one embodiment of any method, cells, or composition described herein, the multilineage hematopoietic progenitor cells are generated by contacting the HE with a nucleic acid or more, wherein the nucleic acid (s) collectively comprises an exogenous gene coding copy of each of the following transcription factors, ERG, HOXA9, HOXA5, LCOR and RUNX1, for the in vivo expression of the transcription factor in the contacted cells. The contacting is in vitro or ex vivo.

In one embodiment of any method, cells, or composition described herein, the contacting of the HE with any vector(s), nucleic acid(s) or compositions comprising the vector(s) or nucleic acid(s) described herein occurs in vitro or ex vivo.

In one embodiment of any methods, cells, or composition described herein, the contacting or introduction is repeated at least once. In one embodiment of any methods, cells, or composition described herein, the contacting or introduction is repeated twice or more times.

In one embodiment of any method, cells, or composition described herein, the method further comprising transfecting the HE with an exogenous gene coding copy of the transcription factor, HOXA10 or SPI1 or both HOXA10 and SPI1, wherein the transfected transcription factor(s) is/are expressed in vivo in the transfected cells. The transfecting is in vitro or ex vivo.

In one embodiment of any method, cells, or composition described herein, the method further comprising transfecting the HE with an exogenous gene coding copy of the transcription factors, HOXA10, wherein the transfected transcription factor is expressed in vivo in the transfected cells.

In one embodiment of any method, cells, or composition described herein, the method further comprising transfecting the HE with an exogenous gene coding copy of the transcription factors, SPI1, wherein the transfected transcription factor is expressed in vivo in the transfected cells.

In one embodiment of any one aspect described, the disclosed transcription factors are expressed in the transfected cells.

In another embodiment of any one aspect described, the disclosed transcription factors are expressed in the engineered cells.

In one embodiment of any one aspect described, the expression of the disclosed transcription factors in the transfected or engineered cells produces a population of multi-lineage HSCs and HSPCs.

Transcription Factors

Runt Related Transcription Factor 1 (RUNX1) is the alpha subunit 2 of a heterodimeric transcription factor that binds to the core element of many enhancers and promoters. The protein encoded by this gene RUNX1 represents the alpha subunit of the heterodimeric transcription factor and is thought to be involved in the development of normal hematopoiesis. Chromosomal translocations involving this gene are well-documented and have been associated with several types of leukemia. Three transcript variants encoding different isoforms have been found for this gene. RUNX1 is essential for hematopoietic commitment of HE and can convert endothelial cells to hematopoietic progenitor cells. The REFSEQ mRNAs for RUNX1 are NM_001001890.2; NM_001122607.1; NM_001754.4; XM_005261068.3; ani XM_005261069.4.

Ligand Dependent Nuclear Receptor Corepressor (LCOR) is a transcriptional corepressor widely expressed in fetal and adult tissues that is recruited to agonist-bound nuclear receptors through a single LxxLL motif, also referred to as a nuclear receptor (NR) box. LCOR is a component of histone deacetylation complex, is mutated in B-cell lymphoma, suggesting a role in B-lymphopoiesis, but this factor has not previously been implicated in HSC functions and its role remains to be defined. LCOR may act as transcription activator that binds DNA elements with the sequence 5-CCCTATCGATCGATCTCTACCT-3 (By similarity). It is a repressor of ligand-dependent transcription activation by target nuclear receptors, repressing of liganddependent transcription activation by ESR1, ESR2, NR3C1, PGR, RARA, RARB, RARG, RXRA and VDR. The REFSEQ mRNAs for LCOR are NM_015652.3; NM_001170765.1; NM_001170766.1; NM_001346516.1; and NM_032440.3.

ERG (ETS-related gene) is an oncogene meaning that it encodes a protein that typically is mutated in cancer. ERG is a member of the ETS (erythroblast transformation—specific) family of transcription factors. The ERG gene encodes for a protein, also called ERG that functions as a transcriptional regulator. Genes in the ETS family regulate embryonic development, cell proliferation, differentiation, angiogenesis, inflammation, and apoptosis. The external idenifications for ERG gene are as follows: HGNC: 3446; Entrez Gene: 2078; Ensembl: ENSG00000157554; OMIM: 165080; UniProtKB: P11308; EMBL: AY204741 mRNA and the corresponding mRNA translation: AAP41719.1; and GENBANK: AY204742 mRNA and the corresponding mRNA translation: AAP41720.1.

Spi-1 Proto-Oncogene (SPI1, also known as PU.1) is required for hematopoietic progenitor cell emergence and regulates myeloid specification. The oncogene is an ETS-domain transcription factor that activates gene expression during myeloid and B-lymphoid cell development. The nuclear protein binds to a purine-rich sequence known as the PU-box found near the promoters of target genes, and regulates their expression in coordination with other transcription factors and cofactors. The protein can also regulate alternative splicing of target genes. Multiple transcript variants encoding different isoforms have been found for this gene. The external idenifications for SPI1 gene is as follows: HGNC: 11241; Entrez Gene: 6688; Ensembl: ENSG00000066336; OMIM: 165170; and UniProtKB: P17947. The REFSEQ mRNAs for SPI1 are NM_001080547.1; NM_003120.2; XM_011520307.1 and XM_017018173.1.

Homeobox protein Hox-A9 is a protein that in humans is encoded by the HOXA9 gene. In vertebrates, the genes encoding the homeobox genes class of transcription factors are found in clusters named A, B, C, and D on four separate chromosomes. Expression of these proteins is spatially and temporally regulated during embryonic development. Hox-A9 is part of the A cluster on chromosome 7 and encodes a DNA-binding transcription factor which may regulate gene expression, morphogenesis, and differentiation. The external idenifications for HOXA9 gene are as follows: HGNC: 5109; Entrez Gene: 3205; Ensembl: ENSG00000078399;

OMIM: 142956; UniProtKB: P31269; EMBL: BT006990 mRNA and the corresponding mRNA translation: AAP35636.1; and GENBANK:AC004080 Genomic DNA. The REFSEQ mRNAs for HOXA9 is NM 152739.3

HOX family members have been reproducibly implicated in hematopoiesis across species. HOXA9 is the key homeotic gene that defines HSC identity, interacting with ERG to support HSC renewal during embryogenesis and stress hematopoiesis, suggesting a basis for the functional cooperation of HOXA9 and ERG in our system. HOXA5 is a transcriptional target of Notch signaling in T-cell progenitors along with HOXA9 and HOXA10, consistent with a role in T-lymphopoiesis. These factors share binding sites in the genome and cooperate to recruit chromatin modulators (e.g. RUNX1 and HOXA families) to induce and maintain HSPCs. The external idenifications for HOXA5 gene are as follows: HGNC: 5106; Entrez Gene: 3202; Ensembl: ENSG00000106004; OMIM: 142952; and UniProtKB: P20719. The REFSEQ mRNAs for HOXA5 is NM_019102.3. The external idenifications for HOXA5 gene are as follows: HGNC: 5100; Entrez Gene: 3206; Ensembl: ENSG00000253293; OMIM: 142957, and UniProtKB: P31260. The REFSEQ mRNAs for HOXA10 are NM_018951.3 and NM_153715.3.

HOX- and ETS-family transcription factors HOXA9 and ERG are inducers of self-renewal and multilineage potential in hematopoietic progenitors differentiated from hPSCs. RORA is a nuclear receptor that plays a role in maintaining quiescence of hematopoietic progenitors. The addition of SOX4 and MYB modulates this network to enable myeloid and erythroid engraftment in vivo.

OCT4, SOX2, KLF4 and c-MYC are the original four transcription factors identified to reprogram mouse fibroblasts into iPSCs. These same four factors were also sufficient to generate human iPSCs. OCT3/4 and SOX2 function as core transcription factors of the pluripotency network by regulating the expression of pluripotency-associated genes. Krüppel-like factor 4 (KLF4) is a downstream target of LIF-STAT3 signaling in mouse ES cells and regulates self-renewal. Human iPSCs can also be generated using four alternative factors; OCT4 and SOX2 are required but KLF4 and c-MYC could be replaced with NANOG, a homeobox protein important for the maintenance of pluripotency in both ES cells and early embryos, and LIN28, an RNA binding protein.

Transcription factor SOX-4 (SOX4). This intronless gene encodes a member of the SOX (SRY-related HMG-box) family of transcription factors involved in the regulation of embryonic development and in the determination of the cell fate. The encoded protein act as a transcriptional regulator after forming a protein complex with other proteins, such as syndecan binding protein (syntenin). The protein may function in the apoptosis pathway leading to cell death as well as to tumorigenesis and may mediate downstream effects of parathyroid hormone (PTH) and PTH-related protein (PTHrP) in bone development. The external idenifications for Homo sapiens (Human) SOX4 gene are as follows: HGNC: 11200; Entrez Gene: 6659; Ensembl: ENSG00000124766; OMIM: 184430; UniProtKB: Q06945; EMBL: BC072668 mRNA mRNA and the corresponding mRNA translation: AAH72668.1; GENBANK: X65661 mRNA and the corresponding mRNA translation: CAA46612.1.

The cDNA encoding the described and desired transcription factors can be cloned by methods known in the art into expression vectors for in vivo expression in the cells. The expression vectors can be constitutive or inducible vectors. The protein and DNA information for transcription factors can be found in the publically available databases such as the GenBank™ database on the National Institute of Health, the UniProt at the Protein knowledgebase, and GeneCard database at the Weizmann Institute for Science. The cDNA clones or plasmids carrying the cDNA can be purchased at BioCat GmbH, and the lentivirus carrying the cDNAs for expression can also be purchased at Applied Biological Materials (ABM) Inc.

In one embodiment of any method, cells, or composition described herein, a vector is used as a transport vehicle to introduce any of the herein described exogenous gene coding copies of transcription factors or reprogramming factors or nucleic acid inhibitor into the target cells selected from the disclosed HE.

In one embodiment of any method, cells, or composition described herein, a vector is used as a transport vehicle to introduce any of the herein described nucleic acid comprising the described exogenous gene coding copies of transcription factors or reprogramming factors or nucleic acid inhibitor into the target cells selected from the disclosed HE.

In one aspect, the present specification provides a vector or more, wherein the vector(s) collectively comprises an exogenous gene coding copies of each of the transcription factors or reprogramming factors or nucleic acid inhibitor described. The exogenous gene coding copy is for the expression of transcription factors or reprogramming factors inside the cells. In one embodiment, each vector consists essentially of a transcription factors or reprogramming factor described herein. In one embodiment, each vector consists essentially of two or more of the described transcription factors or reprogramming factors.

In one aspect, the present specification provides a vector or more, wherein the vector(s) collectively comprises nucleic acids comprising the described exogenous gene coding copies of transcription factors or reprogramming factors or nucleic acid inhibitor. The nucleic acid is for the expression of the transcription factors or reprogramming factors inside the cells.

In one aspect, the present specification provides a vector or more, wherein the vector(s) collectively comprises an exogenous gene coding copy of each of the following transcription factors, ERG, HOXA9, HOXA5, LCOR and RUNX1 described herein. In another aspect, the vector(s) collectively further comprise an exogenous gene coding copy of HOXA10 and SPI1.

In another aspect, the disclosed herein also provides a host cell comprising a vector or more described herein or nucleic acid(s) of the transcription factors or reprogramming factors or both described herein.

In another aspect, the disclose also provides a host cell comprising a vector or more described herein or nucleic acid(s) of the transcription factors, ERG, HOXA9, HOXA5, LCOR and RUNX1 described herein.

In another aspect, the host cell further comprises a vector or more described herein or nucleic acid(s) of the transcription factors HOXA10 and SPI1.

In another aspect, the host cell further comprises a vector or more described herein or nucleic acid(s) of reprogramming factors or both described herein, OCT4, SOX2, and KLF4, and optionally with c-MYC or nanog and LIN28. For example, the one or more vectors collectively carry the nucleic acids of the reprogramming factors OCT4, SOX2, NANOG, and LIN 28, or collectively carry the nucleic acids of the reprogramming factors OCT4, SOX2, and KLF4, or OCT4, SOX2, KLF4, and c-MYC.

In one embodiment of any method, cells, or composition described herein, the vector further comprises a spleen focus-forming virus promoter, a tetracycline-inducible promoter, a Doxycycline (Dox)-inducible, or a β-globin locus control region and a β-globin promoter. In one embodiment, the promoter provide for targeted expression of the nucleic acid molecule therein. Other examples of promoters include but are not limited to the CMV promoter and EF1α promoters for the various transgenes.

In one embodiment of any method, cells, or composition described herein, the vector is a virus.

In one embodiment of any method, cells, or composition described herein, the virus is a lentivirus, an adenovirus, an adeno-associated virus, a pox virus, an alphavirus, or a herpes virus. In one embodiment of any method, cells, or composition described herein, the virus is an avian viral vector.

In one embodiment of any method, cells, or composition described herein, the in vivo expression of the described transcription factors are regulatable. That is, the promoters used in the vectors for gene expression are inducible.

In one aspect of any method, cells, or composition described herein, the lentivirus is selected from the group consisting of: human immunodeficiency virus type 1 (HIV-1), human immunodeficiency virus type 2 (HIV-2), caprine arthritis-encephalitis virus (CAEV), equine infectious anemia virus (EIAV), feline immunodeficiency virus (FIV), bovine immune deficiency virus (BIV), and simian immunodeficiency virus (SIV).

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the methods and compositions described herein can include such other forms of expression vectors, such as viral vectors (e.g., replication defective retroviruses, lentiviruses, adenoviruses and adeno-associated viruses), which serve equivalent functions.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the DNA-targeting endonuclease can be delivered by way of a vector comprising a regulatory sequence to direct synthesis of the DNA-targeting endonuclease at specific intervals, or over a specific time period. It will be appreciated by those skilled in the art that the design of the expression vector can depend on such factors as the choice of the target cell, the level of expression desired, and the like.

Suitable viral vectors include, but are not limited to, vectors based on RNA viruses, such as retrovirus-derived vectors (for example, Moloney murine leukemia virus (MLV)-derived vectors), and more complex retrovirus-derived vectors (such as Lentivirus-derived vectors); and vectors based on DNA viruses, such as adenovirus-based vectors and adeno-associated virus (AAV)-based vectors. In some embodiments, the polynucleotide delivery system comprises a retroviral vector, more preferably a lentiviral vector. Non-limiting examples of viral vector include lentivirus vectors derived from human immunodeficiency virus 1 (HIV-1), HIV-2, feline immunodeficiency virus (FIV), equine infectious anemia virus, simian immunodeficiency virus (SIV) and maedi/visna virus.

In one embodiment of any one aspect described, the population of multi-lineage HSCs and HSPCs, produced by the expression of the disclosed transcription factors in the transfected or engineered cells, engrafts in vivo in the recipient subject and produces blood cells in vivo.

In one embodiment of any one aspect described, the population of multi-lineage HSCs and HSPCs, produced by the expression of the disclosed transcription factors in the transfected or engineered cells, reconstitutes the hematopoietic system in vivo in the recipient subject.

In one embodiment of any one aspect described, the engineered cell comprises an exogenous copy of each of the following transcription factors ERG, HOXA9, HOXA5, LCOR and RUNX1.

In one embodiment of any one aspect described, the engineered cell further comprises an exogenous copy of each of the following reprogramming factors OCT4, SOX2, KLF4 and optionally c-MYC.

In one embodiment of any one aspect described, the engineered cell further comprises an exogenous copy of each of the following reprogramming factors OCT 4, SOX2, NANOG, and LIN28.

In one embodiment of any one aspect described, the composition of engineered cells further comprises a pharmaceutically acceptable carrier.

In one embodiment of any one aspect described, the subject is patients who has undergone chemotherapy or irradiation or both, and manifest deficiencies in immune or blood function or lymphocyte reconstitution or both deficiencies in immune function and lymphocyte reconstitution.

In one embodiment of any one aspect described, the subject prior to implantation, the immune cells are treated ex vivo with prostaglandin E2 and/or antioxidant N-acetyl-L-cysteine (NAC) to promote subsequent engraftment in a recipient subject.

In one embodiment of any one aspect described, the disclosed engineered cells are autologous to the recipient subject or at least HLA type matched with the recipient subject.

It is also envisioned that the methods described herein can be used as prophylaxis Uses of Engineered Immune Cells Derived from Pluripotent Stem Cells The engineered cells described herein are useful in the laboratory for biological studies. For examples, these cells can be derived from an individual having a genetic disease or defect, and used in the laboratory to study the biological aspects of the diseases or defect, and to screen and test for potential remedy for that diseases or defect. Contemplated but not limited to are congenital hematologic disorders such as Diamond-Blackfan-Anemia, Shwatchman-Diamond-Anemia, and immune deficiency such as Omenn syndrome.

Alternatively, the engineered cells described herein are useful in cellular replacement therapy in subjects having the need. For example, patients who have undergone chemotherapy. For example, patients who have undergone chemotherapy or irradiation or both, and manifest deficiencies in immune function and/or lymphocyte reconstitution. For example, cellular replacement therapy can be performed in subjects with congenital hematologic disorders described herein.

In various embodiments, the engineered cells described herein are administered (ie. implanted or transplanted) to a subject in need of cellular replacement therapy. The implanted engineered cell engrafts and reconstitutes the hematopoietic system in the recipient subject.

As used herein, the terms "administering," "introducing" and "transplanting" are used interchangeably in the context of the placement of described cells, e.g. HSC, HSPC, hematopoietic progenitor cells, into a subject, by a method or route which results in at least partial localization of the introduced cells at a desired site, such as a site of injury or repair, such that a desired effect(s) is produced. The cells e.g. HSC, HSPC, hematopoietic progenitor cells, or their differentiated progeny can be administered by any appropriate route which results in delivery to a desired location in the subject where at least a portion of the implanted cells or components of the cells remain viable.

In various embodiments, the engineered cells described herein are optionally expanded ex vivo prior to administration to a subject. In other embodiments, the engineered cells are optionally cryopreserved for a period, then thawed prior to administration to a subject.

The engineered cells used for cellular replacement therapy can be autologous/autogeneic ("self") or non-autologous ("non-self," e.g., allogeneic, syngeneic or xenogeneic) in relation to the recipient of the cells. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In other embodiments, the engineered cells of the embodiments of the present disclosure are allogeneic.

In various embodiments, the engineered cell described herein that is to be implanted into a subject in need thereof is autologous or allogeneic to the subject.

In various embodiments, the engineered cell described herein can be derived from one or more donors, or can be obtained from an autologous source. In some embodiments of the aspects described herein, the engineered cells are expanded in culture prior to administration to a subject in need thereof.

In various embodiments, the engineered cell described herein can be derived from one or more donors, or can be obtained from an autologous source.

In various embodiments, prior to implantation, the recipient subject is treated, or was previously been treated with chemotherapy and/or radiation.

In one embodiment, the chemotherapy and/or radiation are to reduce endogenous stem cells in the recipient subject to facilitate engraftment of the implanted cells.

In one embodiment, the chemotherapy and/or radiation have reduced the ability of the recipient subject to synthesize sufficient hematopoietic cells to sustain life, e.g., inability to make blood cells, platelet cells, etc.

In various embodiments, prior to implantation, the engineered immune cells or the inhibited, reverse-lineage multilineage hematopoietic progenitor cells are treated ex vivo with prostaglandin E2 and/or antioxidant N-acetyl-L-cysteine (NAC) to promote subsequent engraftment in a recipient subject.

In various embodiments, the recipient subject is a human.

In various embodiments, the subject is diagnosed with HIV, a hematological disease, undergoing a cancer treatment, or an autoimmune disease. For example, the subject has aplastic anemia, X-linked lymphopenic immune deficiency, Wiskott-Aldrich syndrome, Fanconi anemia, cancer, or acute lymphoblastic leukemia (ALL).

In one aspect of any method, cells and composition described herein, a subject is selected to donate a somatic cell which would be used to produce iPSCs and an engineered immune cell described herein. In one embodiment, the selected subject has a genetic disease or defect.

In various embodiments, the donor subject is a human.

In various embodiments, the donor or the recipient subject is an animal, human or non-human, and rodent or non-rodent. For example, the subject can be any mammal, e.g., a human, other primate, pig, rodent such as mouse or rat, rabbit, guinea pig, hamster, cow, horse, cat, dog, sheep or goat, or a non-mammal such as a bird.

In various embodiments, the donor or the recipient subject is diagnosed with HIV, a hematological disease or cancer.

In one aspect of any method, cells and composition described herein, a biological sample or a population of embryonic stem cells, somatic stem cells, progenitor cells, bone marrow cells, hematopoietic stem cells, or hematopoietic progenitor cells is obtained from the donor subject.

In various embodiments, biological sample or a population of embryonic stem cells, somatic stem cells, progenitor cells, bone marrow cells, hematopoietic stem cells, or hematopoietic progenitor cells described herein can be derived from one or more donors, or can be obtained from an autologous source.

In one embodiment, the embryonic stem cells, somatic stem cells, progenitor cells, bone marrow cells, hematopoietic stem cells, hematopoietic progenitor cells are isolated from the donor subject, transfected, cultured (optional), and transplanted back into the same subject, i. e. an autologous cell transplant. Here, the donor and the recipient subject is the same individual. In another embodiment, the embryonic stem cells, somatic stem cells, progenitor cells, bone marrow cells, hematopoietic stem cells, or hematopoietic progenitor cells are isolated from a donor who is an HLA-type match with a subject (recipient). Donor-recipient antigen type-matching is well known in the art. The HLA-types include HLA-A, HLA-B, HLA-C, and HLA-D. These represent the minimum number of cell surface antigen matching required for transplantation. That is the transfected cells are transplanted into a different subject, i.e., allogeneic to the recipient host subject. The donor's or subject's embryonic stem cells, somatic stem cells, progenitor cells, bone marrow cells, hematopoietic stem cells, or hematopoietic progenitor cells can be transfected with a vector or nucleic acid comprising the nucleic acid molecule(s) described herein, the transfected cells are cultured, inhibited, and differentiated as disclosed, optionally expanded, and then transplanted into the recipient subject. In one embodiment, the transplanted engineered immune cells engrafts in the recipient subject. In one embodiment, the transplanted engineered immune cells reconstitute the immune system in the recipient subject. The transfected cells can also be cryopreserved after transfected and stored, or cryopreserved after cell expansion and stored.

The engineered cells having multilineage hematopoietic progenitor cells described herein may be administered as part of a bone marrow or cord blood transplant in an individual that has or has not undergone bone marrow ablative therapy. In one embodiment, genetically modified cells contemplated herein are administered in a bone marrow transplant to an individual that has undergone chemoablative or radioablative bone marrow therapy.

In one embodiment, a dose of cells is delivered to a subject intravenously. In one embodiment, the cells are intravenously administered to a subject.

In particular embodiments, patients receive a dose of the cells, e.g., engineered cells of this disclosure, of about $1\times10^5$ cells/kg, about $5\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $5\times10^7$ cells/kg, about $1\times10^8$ cells/kg, or more in one single intravenous dose.

In certain embodiments, patients receive a dose of the cells, e.g., engineered cells, of at least $1\times10^5$ cells/kg, at least $5\times10^5$ cells/kg, at least $1\times10^6$ cells/kg, at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, at least $1\times10^7$ cells/kg, at least $5\times10^7$ cells/kg, at least $1\times10^8$ cells/kg, or more in one single intravenous dose.

In an additional embodiment, patients receive a dose of the cells, e.g., engineered cells of this disclosure, of about $1\times10^5$ cells/kg to about $1\times10^8$ cells/kg, about $1\times10^6$ cells/kg to about $1\times10^8$ cells/kg, about $1\times10^6$ cells/kg to about $9\times10^6$ cells/kg, about $2\times10^6$ cells/kg to about $8\times10^6$ cells/kg, about $2\times10^6$ cells/kg to about $8\times10^6$ cells/kg, about $2\times10^6$ cells/kg to about $5\times10^6$ cells/kg, about $3\times10^6$ cells/kg to about $5\times10^6$ cells/kg, about $3\times10^6$ cells/kg to about $4\times10^8$ cells/kg, or any intervening dose of cells/kg.

In general, the engineered cells described herein are administered as a suspension with a pharmaceutically acceptable carrier. For example, as therapeutic compositions. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the cells as described herein using routine experimentation.

In some embodiments, the compositions of engineered cells described further comprise a pharmaceutically acceptable carrier. In one embodiment, the pharmaceutically acceptable carrier does not include tissue or cell culture media.

In various embodiments, a second or subsequent dose of cells is administered to the recipient subject. For example, second and subsequent administrations can be given between about one day to about 30 weeks after the previous administration. Two, three, four or more total administrations can be delivered to the individual, as needed.

A cell composition can be administered by any appropriate route which results in effective cellular replacement treatment in the subject, i.e. administration results in delivery to a desired location in the subject where at least a portion of the composition delivered, i.e. at least $1\times10^4$ cells are delivered to the desired site for a period of time. Modes of administration include injection, infusion, or instillation. "Injection" includes, without limitation, intravenous, intraarterial, intraventricular, intracardiac injection and infusion. For the delivery of cells, administration by injection or infusion is generally preferred.

Efficacy testing can be performed during the course of treatment using the methods described herein. Measurements of the degree of severity of a number of symptoms associated with a particular ailment are noted prior to the start of a treatment and then at later specific time period after the start of the treatment.

The embodiments of the present disclosure can be defined in any of the following numbered paragraphs:

[1]. A method for making hematopoietic stem cells (HSCs) and hematopoietic stem and progenitor cells (HSPCs) comprising in vitro transfecting hemogenic endothelia cells (HE) with an exogenous gene coding copy of each of the following transcription factors ERG, HOXA9, HOXA5, LCOR and RUNX1, wherein the transcription factors are expressed in the transfected cells to produce a population of multilineage HSCs and HSPCs that engrafts in recipient host after implantation.

[2]. A method of making hematopoietic stem cells (HSCs) and hematopoietic stem and progenitor cells (HSPCs) comprising: (a) generating embryonic bodies (EB) from pluripotent stem cells; (b) isolating hemogenic endothelia cells (HE) from the resultant population of EB; (c) inducing endothelial-to-hematopoietic transition (EHT) in culture in the isolated HE to obtain hematopoietic stem cells, and (d) in vitro transfecting the induced HE with an exogenous gene coding copy of each of the following transcription factors ERG, HOXA9, HOXA5, LCOR and RUNX1.

[3]. The method of paragraph 1 or 2, wherein the method is an in vitro method.

[4]. The method of any one of the preceding paragraphs, wherein the EB are generated or induced from pluripotent stem cells (PSC) by culturing or exposing the PSC to mophogens for about 8 days.

[5]. The method of paragraph 4, wherein the mophogens selected from the group consisting of Holo-Transferrin, mono-thioglycerol (MTG), ascorbic acid, bone morphogenetic protein (BMP)-4, basic fibroblast growth factor (bFGF), SB431542, CHIR99021, vascular endothelial growth factor (VEGF), interleukin (IL)-6, insulin-like growth factor (IGF)-1, interleukin (IL)-11, stem cell factor (SCF), erythropoietin (EPO), thrombopoietin (TPO), interleukin (IL)-3, and Fms related tyrosine kinase 3 ligand (Flt-3L).

[6]. The method of any one of the preceding paragraphs, wherein the EBs are less than 800 microns in size and are selected.

[7]. The method of any one of the preceding paragraphs, wherein the EB cells within the EBs are compactly adhered to each other and requires trypsin digestion in order to dissociate the cells to individual cells.

[8]. The method of paragraph 5 or 7, wherein the EB cells of the selected EBs are dissociated prior to the isolation of HE.

[9]. The method of any one of the preceding paragraphs, wherein the population of PSC is induced pluripotent stem cells (iPS cells) or embryonic stem cells (ESC).

[10]. The method of paragraph 9, wherein the induced pluripotent stem cells are produced by introducing only reprogramming factors OCT4, SOX2, KLF4 and optionally c-MYC or nanog and LIN28 into mature cells.

[11]. The method of paragraph 10, wherein the mature cells are selected from the group consisting of B lymphocytes (B-cells), T lymphocytes, (T-cells), fibroblasts, and keratinocytes.

[12]. The method of paragraph 8, 9 or 10, wherein the induced pluripotent stem cells are produced by introducing the reprogramming factors two or more times into the mature cells.

[13]. The method of any one of the preceding paragraphs, wherein the HE are definitive HE.

[14]. The method of any one of the preceding paragraphs, wherein the HE are isolated immediately from selected and dissociated EB.

[15]. The method of any one of the preceding paragraphs, wherein the HE are FLK1+, CD34+, CD43−, and CD235A−.

[16]. The method of any one of the preceding paragraphs, wherein the hematopoietic cells are CD34+ and CD45+.

[17]. The method of any one of the preceding paragraphs, wherein the endothelial-to-hematopoietic transition occurs by culturing the isolated HE in thrombopoietin (TPO), interleukin (IL)-3, stem cell factor (SCF), IL-6, IL-11, insulin-like growth factor (IGF)-1, erythropoietin (EPO), vascular endothelial growth factor (VEGF), basic fibroblast growth factor (bFGF), bone morphogenetic protein (BMP)4, Fms related tyrosine kinase 3 ligand (Flt-3L), sonic hedgehog (SHH), angiotensin II, chemical AGTR1 (angiotensin II receptor type I) blocker losartan potassium.

[18]. The method of any one of the preceding paragraphs, wherein the multilineage HSCs are CD34+CD38−CD45+.

[19]. The method of any one of the preceding paragraphs, wherein the multilineage HSPCs are CD34+CD45+.

[20]. An engineered cell derived from a population of HE and produced by a method of any one of paragraphs 1-18.

[21]. The engineered cell of paragraph 19, wherein the engineered cell comprises an exogenous copy of each of the following transcription factors ERG, HOXA9, HOXA5, LCOR and RUNX1.

[22]. The engineered cell of paragraph 19 or 20, wherein the engineered cell further comprises an exogenous copy of each of the following reprogramming factors OCT4, SOX2, KLF4 and optionally c-MYC.

[23]. A composition comprising a population of engineered cells of any one of paragraphs 19-21.

[24]. The composition of paragraph 22, further comprising a pharmaceutically acceptable carrier.

[25]. A pharmaceutical composition comprising a population of engineered cells of any one of paragraphs 19-21 and a pharmaceutically acceptable carrier.

[26]. A pharmaceutical composition of paragraph 24 for use in cellular replacement therapy in a subject.

[27]. A method of cellular replacement therapy in a subject in need thereof, the method comprising administering a population of engineered cells of any one of the preceding paragraphs 19-21, or a composition of claim 22-23, or a pharmaceutical composition of any one of the preceding paragraphs 24-25 to a recipient subject.

[28]. The method of cellular replacement therapy of paragraph 27, wherein the subject is a patient who has undergone chemotherapy or irradiation or both, and manifest deficiencies in immune function or lymphocyte reconstitution or both deficiencies in immune function and lymphocyte reconstitution.

[29]. The method of cellular replacement therapy of paragraph 27 or 28, wherein the subject prior to implantation, the immune cells are treated ex vivo with prostaglandin E2 and/or antioxidant N-acetyl-L-cysteine (NAC) to promote subsequent engraftment in a recipient subject.

[30]. The method of cellular replacement therapy of paragraph 27 or 28 or 29, wherein the immune cells are autologous to the recipient subject or at least HLA type matched with the recipient subject.

The embodiments of the present disclosure are further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the present disclosure described herein. Such equivalents are intended to be encompassed by the following claims.

EXAMPLE

Materials and Methods hPSC Culture

All experiments were performed with H9 hESC (NIHhESC-10-0062), PB34 iPS[59], MSC-IPS1[60], PB34 iPS[65], MSC-iPS1[66], 1045-iPSC, and 1157-iPSC established by hES (human embryonic stem cell) core facility at Boston Children's Hospital. See the Children's Hospital webpage at stemcell period childrenshospital period org. Human embryonic stem cells (ESCs) and induced pluripotent stem cells (iPSCs) were maintained on mouse embryonic fibroblasts (GLOBALSTEM) feeders in DMEM/F12+20% KNOCK-OUTSERUM Replacement (INVITROGEN), 1 mM L-glutamine, 1 mM NEAA, 0.1 mM beta-mercaptoethanol, and 10 ng/ml bFGF on 10 cm gelatinized culture dish. Media was changed daily, and cells were passaged 1:4 onto fresh feeders every 7 days using standard clump passaging with collagenase IV. Morphology of pluripotent stem cells (PSCs) was checked under microscopy daily. As a quality control, only dishes with more than 70% of typical PSC colonies were processed for embryoid bodies (EBs) formation. EBs are three-dimensional aggregates of pluripotent stem cells. Cell lines were tested for mycoplasma routinely.

EB Differentiation

EB differentiation was performed as previously described[19]. Briefly, human pluripotent stem cells (hPSCs) colonies were dissociated with 0.05% Trypsin for 5 min in at 37° C., pipetted thoroughly with p1000 until single cells or small aggregates, washed twice with PBS with 2% fetal bovine serum (FBS), and re-suspended in StemPro-34-based media prior to seeding. StemPro-34 (INVITROGEN, 10639-011) is supplemented with L-glutamine (2 mM), penicillin/streptomycin (10 ng/mL), ascorbic acid (1 mM), human holo-Transferrin (150 µg/mL, SIGMA T0665), and monothioglycerol (MTG, 0.4 mM) (referred to as "Supplemented StemPro-34), BMP-4 (10 ng/mL) and Y-27632 (10 uM). The suspended cells were seeded into non-adherent spheroid formation 10 cm plates (EZSPHERE™, ASAHI GLASS CO; Well Size (µm) Diameter: 400-500, Depth: 100-200; No. of well 14,000/dish) at a cell density of 2-5 million cells/dish. About 24 h after seeding, bFGF (5 ng/mL) and BMP4 (10 ng/mL) were added to the media. At day 2 in culture, the developing EBs were collected and re-suspended in supplemented StemPro-34 with SB431542 (6 µM), CHIR99021 (3 µM), bFGF (5 ng/mL) and BMP4 (10 ng/mL). The formation of EBs were checked under microscopy at day 4 and the decision was made to continue EB formation based on the size and morphology of aggregations (quality control; >100 uM, compaction-like tight contact of cells). At day 4, the media is replaced by supplemented StemPro-34 with VEGF (15 ng/mL) and bFGF (10 ng/mL). At day 6, the media is replaced by supplemented StemPro-34 with bFGF (10 ng/mL), VEGF (15 ng/mL), IL-6 (10 ng/mL), IGF-1 (25 ng/mL), IL-11 (5 ng/mL) and SCF (50 ng/mL). Cultures were maintained in a 5% $CO_2$/5% $O_2$/90% $N_2$ environment. After 8 days in culture, the EBs are harvested and sorted for definitive HE via surface markers.

HE Sorting

To avoid potential damage with hydrodynamic pressure and contamination through FACS (Elliot et al., 2009), for functional assay, the isolation of HE was carried out by MACS. Freshly dissociated EB cells (at day 8 time point) were filtered through a 70 µm filter and stained with CD34 microbeads (MILTENYI) for 30 min at 4° C. CD34+ cells were isolated with LS columns (MILTENYI). Around 0.1-0.5×10⁶ cells were obtained per 10 cm dish of EB formation. A sample from each batch was analyzed by FACS to validate its purity of HE. The following antibodies or dyes are used in the FACS: CD34 PE-Cy7 (8G12; BD), FLK1 AF647 (89106; BD), CD235a/Glycophorin (GLY)-A FITC (11E4B-7-6; Coulter), CD43 PE (1G10; BD) and DAPI. For accurate isolation of HE for expression profile by microarray and qRT-PCR, isolation of HE was carried out by FACS. Dissociated EBs (at day 8 time point) were re-suspended at 1-3×10⁶ per 100 ml staining buffer (PBS+2% FBS). Cells were stained with a 1:50 dilution of CD34 PE-Cy7 (8G12; BD), FLK1 AF647 (89106; BD), CD235a/Glycophorin (GLY)-A FITC (11E4B-7-6; Coulter), CD43 PE (1G10; BD) and DAPI for 30 min at 4° C. dark. All FACS sorting was performed on a BD FACS Aria II cell sorter using a 100 micrometer nozzle to avoid potential damage to HE.

Microarray and CellNet Analysis of HE

All the samples used for microarray analysis were FACS sorted. The following antibodies are used for identifying HE: CD34 PE-Cy7 (8G12; BD), FLK1 AF647 (89106; BD), CD235a/Glycophorin (GLY)-A FITC (11E4B-7-6; Coulter), CD43 PE (1G10; BD). Fetal liver hematopoietic stem cells (HSCs) were purchased from STEMCELL Technologies and stained with the following antibodies for identifying HSC: CD38 PE-Cy5 (LS198-4-3; Clontech), CD34 PE-Cy7, and CD45 PE (HI30; BD). Between 10,000-50,000 cells were sorted for each cell type for each replicate (n=2 or 3). The RNAeasy Microkit (QIAGEN) was used to collect and prepare total RNA for microarray analysis. The Ovation Picokit (NUGEN) was used for pre-amplification, where required. Gene expression profiling was performed on AFFYMETRIX 430 2.0 gene chips per standard protocol. Microarray data were analyzed per standard protocol using R/Bioconductor. The classification and GRN of HE were analyzed by CellNet (Callan et al., 2014). Briefly, we reasoned that the extent to which a GRN is established in a sample is reflected in the expression of the genes in the GRN such that the GRN genes should fall within a range of expression observed in the corresponding C/T in the training data. We formalized this notion as a GRN status metric, defined in comparison to the complete training data set. The status of C/T GRN in a query sample is defined as the weighted mean of the Z scores of the genes in the GRN, where the Z score is defined in reference to the expression distribution of each gene in a C/T. The GRN status score can be weighted by the absolute expression level of each gene in a C/T so that genes more highly expressed have more influence on the GRN status (default) and/or by the importance to the Random Forest classifier.

Endothelial-to-Hematopoietic Transition (EHT) Culture

EBs were dissociated on day 8 by digestion with 0.05% Trypsin for 5 min at 37° C., pipetted thoroughly with p1000 pipette to generate a single cell suspension and washed with PBS+2% FBS. Dissociated EBs were immediately processed for the isolation of HE. Unlike HSPCs in previous report that used frozen batches[17], HE delayed (approximately 2-3 days) recovery of morphology and growth once frozen, thus all the experiments were done with freshly isolated HE. Thus, cells were re-suspended in 1 mL of PBS+2% FBS and incubated with human CD34 MicroBead kit for 1 h (MILTENYL BIOTEC, 130-046-702). After incubation, cells were washed with PBS+2% FBS and isolated by magnetic cell isolation (MACS) using LS columns (MILTENYL BIOTEC, 130-042-401). Sorted CD34+ cells were re-suspended in supplemented StemPro-34 media, containing Y-27632 (10 uM), TPO (30 ng/mL), IL-3 (10 ng/mL), SCF (50 ng/mL), IL-6 (10 ng/mL), IL-11 (5 ng/mL), IGF-1 (25 ng/mL), VEGF (5 ng/mL), bFGF (5 ng/mL), BMP4 (10 ng/mL), and Flt-3L (10 ng/mL) as reported[20] and seeded at a density of 25-50×10⁴ cells per well onto thin-layer MATRIGEL-coated 24-well plates. All recombinant factors are human and most were purchased from Peprotech.

Sorted HE cells were seeded onto thin-layer MATRIGEL-coated 96-well plates (flat-bottom) at a density of 5×10⁴/well in supplemented StemPro-34 media, containing TPO (30 ng/ml), IL-3 (30 ng/ml), SCF (100 ng/ml), IL-6 (10 ng/ml), IL-11 (5 ng/ml), IGF-1 (25 ng/ml), EPO (2 U/ml), VEGF (5 ng/ml), bFGF (5 ng/ml), BMP4 (10 ng/ml), Flt-3L (10 ng/ml), SHH (20 ng/ml), angiotensin II (10 µg/l) and the chemical AGTR1 (angiotensin II receptor type I) blocker losartan potassium (100 µM, Tocris) as reported[20]. All recombinant factors are human and most were purchased from Peprotech. The exception is angiotensin II, which was purchased from Sigma.

Lentivirus Production

Plasmids for the TF library were obtained as Gateway plasmids (Harvard Plasmid Serive; GeneCopoeia). Open reading frames were cloned into lentiviral vectors using LR Clonase (INVITROGEN). Two vectors were used, pSMAL-GFP (constitutive) and pINDUCER-21[61]. Lentiviral particles were produced by transfecting 293T-17 cells (ATCC) with the second-generation packaging plasmids (pMD2.G and psPAX2 from Addgene). Virus was harvested 36 and 60 hr after transfection and concentrated by ultracentrifugation at 23,000 rpm for 2 hr 15 min at 4° C. Virus was reconstituted with 50 uL of EHT culture media. Constructs were titered by serial dilution on 293T cells using GFP as an indicator. Polycistronic vectors were made as follows. LCOR-P2A-HOXA9-T2A-HOXA5 and RUNX1-P2A-ERG DNA fragments were synthesized and cloned into TOPO-D cloning vector respectively by GENSCRIPT, then Gateway-recombined with pINDUCER-21.

Lentiviral Gene Transfer

At day 3 of EHT culture, HE cells were beginning to produce potentially hematopoietic 'round' cells, the occurrence of this phenomenon used as quality control of HE induction and transition to hematopoietic cells for each batch of experiment. The infection media was EHT culture media supplemented with Polybrene (8 ug/mL, SIGMA). Lentiviral infections were carried out in a total volume of 150 ul or 250 ul (for a 24-well plate). The multiplicity of infection for the factors was as follows: Library 3.0 for each, ERG 5.0, HOXA5 5.0, HOXA9 5.0, HOXA10 5.0, LCOR 5.0, RUNX1 5.0, and SPI1 5.0. HE was vulnerable to damage during spinoculation, thus infections were carried out static for 12 hours, then 50 uL or 250 uL of fresh EHT media was supplemented to dilute Polybrene. Parallel wells were kept cultured for additional 3 days to measure infection efficiency by percentage of GFP+ DAPI-cells by FACS, 30-70% infection efficiency.

In Vitro Screening Via CFU

Followed by lentiviral gene transfer, cells were maintained for 5 days in EHT culture media supplemented with doxycycline (2 ug/mL, SIGMA) to induce transgene expression in vitro. $5 \times 10^4$ cells were plated into 3 ml of complete methylcellulose (H4434; STEMCELL Technologies). Additional cytokines added were: 10 ng/ml FLT3, 10 ng/ml IL6, and 50 ng/ml TPO (R&D Systems). The mixture was distributed into two 60 mm dishes and maintained in a humidified chamber at 37° C. for 14 days. Colonies were scored manually or using the BD Pathway 855 fluorescent imager. At 14 days, granulocyte/erythrocyte macrophage/mega-karyocyte (GEMM) colonies were picked up by P20 pipette. Between 10-20 GEMM colonies were picked for each replicates (n=3). The QIAamp DNA Micro kit (QIAGEN) was used to collect and prepare total genomic DNA for PCR detection of transgenes. Nested PCR reactions were: 1st round with LNCX Fwd primer (5'-AGC TCG TTT AGT GAA CCG TCA GAT C-3') and EGFP N Rev primer (5'-CGT CGC CGT CCA GCT CGA CCA G-3'). This PCR program consists of 1 cycle of 95° C. for 5 min, 36 cycles of 95° C. for 30 sec followed by 60° C. for 30 sec then followed by 72° C. for 5 min, 1 cycle of 72° C. for 10 min, and a terminating cycle of 4° C. for indefinite period; 2nd round with forward primer for each gene (listed in Table) and HA Rev primer (5'-TCT GGG ACG TCG TAT GGG TA-3'). This PCR program consists of 1 cycle of 95° C. for 5 min, 36 cycles of 95° C. for 30 sec followed by 60° C. for 30 sec then followed by 72° C. for 30 sec, 1 cycle of 72° C. for 10 min, and a terminating cycle of 4° C. for indefinite period.

In Vivo Screening Via Transplantation 12 hours after lentiviral gene transfer, cells were recovered by dispase for 5 min at 37° C., and washed by PBS three times to ensure no carry-over of virus. Cells were re-suspended at $0.5-1.0 \times 10^6$ cells per 25 uL buffer (PBS+2% FBS from STEMCELL Technologies) and kept on ice until injection. $0.5-1.0 \times 10^6$ cells were intrafemorally injected to NOD/LtSz-scidIL2Rgnull (NSG) mice and treated with doxycycline as described in the section on Mouse transplantation. Up to 100 uL peripheral blood (PB) were collected every 2-4 weeks, through 14 weeks. Mice were sacrificed and harvested for bone marrow (BM) and thymus at 8-14 weeks. For transgene detection in engrafted cells, each lineage cells were FACS sorted from BM. The following antibodies are used for identifying cell types, myeloid cells: CD33 APC (P67.6; BD), CD45 PE-Cy5 (J33; Coulter). B-cells: CD19 PE (HIB19; BD), CD45 PE-Cy5 (J33; Coulter); T-cells: CD3 PE-Cy7 (SK7; BD), CD45 PE-Cy5 (J33; Coulter). Between 10,000-50,000 cells were isolated with 2 or 3 biological replicates for multiple cell lines (iPSCs and ESCs). The QIAamp DNA Micro kit (QIAGEN) was used to collect and prepare total genomic DNA for PCR detection of transgenes. Nested PCR reaction was done as similar to in vitro screening of above section.

Mouse Transplantation

NOD/LtSz-scidIL2Rgnull (NSG) (Jackson Labs) mice were bred and housed at the Boston Children's Hospital (BCH) animal care facility. Animal experiments were performed in accordance to institutional guidelines approved by BCH animal care committee. Intra-femoral transplants have been previously described. Briefly, 6-10 week old mice were irradiated (250 rads) 12 hrs before transplant. Prior to transplantation, mice were temporarily sedated with isoflurane. A 27 g needle was used to drill the left femur (injected femur), and $0.5-1.0 \times 10^6$ cells were transplanted in a 25 μL volume using a 28.5 g insulin needle. Sulfatrim was administered in drinking water to prevent infections after irradiation. 625 ppm Doxycycline Rodent Diet (Envigo-Teklad Diets) and Doxycycline (1.0 mg/ml) was added to the drinking water to maintain transgene expression in vivo for 2 weeks[12]. Secondary transplantation was carried with 1,000-2,000 human CD34+ cells (isolated from BM by MACS with CD34 microbeads) at 8 weeks. Isolated cells were resuspended at 1,000-2,000 cells per 25 uL buffer (PBS+2% FBS from STEMCELL Technologies) and kept on ice until injection. Cells were intrafemorally injected to NOD/LtSz-scidIL2Rgnull (NSG) and treated with Doxycycline via food and drinking water for 2 weeks.

Flow Cytometry

Cells grown in EHT culture or harvested animal tissues were stained with the following antibody panels. HE panel: CD34 PE-Cy7 (8G12; BD), FLK1 AF647 (89106; BD), CD235a/Glycophorin (GLY)-A FITC (11E4B-7-6; Coulter), CD43 PE (1G10; BD). HSPC panel: CD38 PE-Cy5 (LS198-4-3; Clontech), CD34 PE-Cy7, and CD45 PE (HI30; BD). Lineage panel: CD235a/Glycophorin (GLY)-A PE-Cy7 or FITC (11E4B-7-6; Coulter), CD33 APC (P67.6; BD), CD19 PE (HIB19; BD), IgM BV510 (G20-127; BD), CD4 PE-Cy5 (13B8.2; Coulter), CD3 PE-Cy7 (SK7; BD), CD8 V450 (RPA-T8; BD), TCRαβ BV510 (T10B9; BD), TCRγδ APC (B1; BD), CD45 PE-Cy5 (J33; Coulter), CD15 APC (HI98; BD) and CD31/PECAM PE (WM59; BD). All stains were performed with $<1 \times 10^6$ cells per 100 μl staining buffer (PBS+2% FBS) with 1:100 dilution of each antibody, 30 min at 4C in dark. Compensation was performed by automated compensation with anti-mouse Igk negative beads (BD) and CB MNC stained with individual ab. All acquisition was performed on BD Fortessa cytometer. For detection of engraftment, human cord blood-engrafted mouse marrow was used as a control to set gating; Sorting was performed on a BD FACS Aria II cell sorter.

Cytospin of Erythroid and Neutrophils 5,000-10,000 of FACS sorted erythroid (CD235a/Glycophorin (GLY)-A PE-Cy7 or FITC (11E4B-7-6; Coulter)), plasmacytoid lymphocytes (CD19 PE (HIB19; BD), IgM BV510 (G20-127; BD), CD38 PE-Cy5 (LS198-4-3; Clontech)) and neutrophils (CD15 APC (HI98; BD), CD31/PECAM PE (WM59; BD) and CD45 PE-Cy5 (J33; Coulter)) were cytospun onto slides (500 rpm for 10 minutes), air dried, and stained with May-Grunwald and Giemsa stains (both from Sigma), washed with water, air dried, and mounted, followed by examination by light microscopy.

Quantitative PCR

RNA extraction was performed using the RNAeasy Microkit (QIAGEN). Reverse transcription was performed using Superscript III (>5,000 cells) or VILO reagent (<5,000 cells) (Invitrogen). Quantitative PCR was carried out in triplicate with SYBR Green (Applied Biosystems). Transcript abundance was calculated using the standard curve method. Primers used for globin genes62: huHbB F (5'-CTG AGG AGA AGT CTG CCG TTA-3'), huHbB R (5'-AGC ATC AGG AGT GGA CAG AT-3'), huHbG F (5'-TGG ATG ATC TCA AGG GCA C-3'), huHbG R (5'-TCA GTG GTA TCT GGA GGA CA-3'), huHbE F (5'-GCA AGA AGG TGC TGA CTT CC-3'), huHbE R (5'-ACC ATC ACG TTA CCC AGG AG-3').

ELISA of Terminally Differentiated Cells

FACS isolated neutrophils (CD15+ PECAM+CD45+), T-cells (CD3+CD45+) were cultured in IMDM+10% FBS overnight in 96-well pate (flat-bottom). Then supernatant was taken and analyzed by MPO- or IFNγ-ELISA-Ready-SET-Go! Kit (eBioscience) according to the manufacturer's protocol. The amount of IFNγ was normalized per 1,000 cells. Human Ig production was measured from 50 uL of serum from NSG mice at 8 weeks (IgM) and 14 weeks post engraftment (IgG). Immunization of mice was done with OVA (F5503, Sigma) with Freund's complete adjuvant (F5881, Sigma), followed by booster doses of Freund's incomplete adjuvant (F5506, Sigma) according to manufacture's instruction.

T-Cell Receptor CDR3 Sequencing

Human CD3+ T cells were FACS-isolated from thymus of engrafted NSG mice. Purified DNA was subjected to next generation sequencing of the complementarity determining region 3 (CDR3) using immunoSEQ (Adaptive Biotechnology, Seattle, Wash.) and analyzed with the immunoSEQ Analyzer software (Adaptive Biotechnology).

Affymetrix SNP 6.0 Genotyping of Engrafted Cells 250 ng aliquots of genomic DNA from human CD45+ BM cells (CD45 PE-Cy5 (J33; Coulter)) from engrafted NSG mice and original PSCs (2 biological replicates) were digested with either Nsp1 or Sty1. A universal adaptor oligonucleotide was then ligated to the digested DNAs. The ligated DNAs were diluted with water and three 10 uL aliquots from each well of the Sty 1 plate and four 10 uL aliquots from each well of the Nsp 1 plate were transferred to fresh 96-well plates. PCR master mix was added to each well and the reactions cycled as follows: 94° C. for 3 min; 30 cycles of 94° C. for 30 s, 60° C. for 45 s, 68° C. for 15 s; 68° C. for 7 min; 4° C. hold. Following PCR, the 7 reactions for each sample were combined and purified by precipitation from 2-propanol/7.5M ammonium acetate. The UV absorbance of the purified PCR products was measured to insure a yield ≥4 ug/uL. 45 uL (≥180 ug) of each PCR product was fragmented with DNAse 1 so the largest fragments were <185 bp. The fragmented PCR products were then end-labeled with a biotinylated nucleotide using terminal deoxynucleotidyl transferase. For hybridization, the end-labeled PCR products were combined with hybridization cocktail, denatured at 95° C. for 10 min and incubated at 49° C. 200 mL of each mixture was loaded on a GeneChip and hybridized overnight at 50° C. and 60 rpm. Following 16-18 hrs of hybridization, the chips were washed and stained using the GenomeWideSNP6_450 fluidics protocol with the appropriate buffers and stains. Following washing and staining, the GeneChips were scanned on a GeneChip Scanner 3000 using AGCC software. Genotype calls (chp files) were generated in Affymetrix Genotyping Console using the default parameters. The resulting chp files were analyzed for familial relationships using the identity by state algorithm implemented in Partek Genomics Suite.

Pooled RNA-Sequencing

Engrafted human CD34+CD38−CD45+ HSCs were isolated from BM from either iPS-derived HE- or CB-injected NSG mice, then RNA was purified with RNeasy Micro kit (QIAGEN). QC of RNA was done by Bioanalyzer and Qubit analysis. Passed samples were converted into library and sequenced by Nextseq PE75 kit.

Single-Cell RNA-Sequencing with in-Droplet-Seq Technology

Engrafted human CD34+CD38−CD45+ HSCs were isolated from BM from either iPS-derived HE- or CB-injected NSG mice, then processed for in-droplet-barcoding according to a previous report[63]. Library was QCed with Bioanalyzer and sequenced by Nextseq PE 75 kit.

Lentiviral integration detection by ligation-mediated PCR and next-generation sequencing Either CD33+ myeloid, CD19+ B− and CD3+ T-cells were isolated from BM from HE-injected NSG mice. Genomic DNA was purified with QIAamp DNA Micro kit (QIAGEN). Ligation-mediated PCR-based detection of lentiviral integration sites was done with Lenti-X Integration Site Analysis Kit (Clontech) according to manufacture's instruction. Sequencing-based detection (Integ-seq) was done following a previous report[64].

Single-Cell RNA-Sequencing with in-Droplet-Seq Technology

Engrafted human CD34+CD38−CD45+ HSCs were isolated from BM from either iPS-derived HE- or CB-injected NSG mice, then processed for in-droplet-barcoding according to a previous report 72. Library was QCed with Bioanalyzer and sequenced by Nextseq PE 75 kit. The t-Distributed Stochastic Neighbor Embedding (t-SNE) algorithm was used to visualize transcriptome similarities and population heterogeneity of cord blood HSCs and iPSC-derived HSCs. t-SNE performs a dimensionality reduction of multidimensional single-cell RNA-seq data into a low dimensional space, preserving pairwise distances between datapoints as good as possible, allowing a global visualization of subpopulation structure and cell-cell similarities. We used the R package tsne in our analyses. The t-SNE map was initialized with point-to-point distances computed by classical multidimensional scaling and the R plot function was used to visualize t-SNE maps annotated by cord blood or iPSC-derived HSCs. Plots showing t-SNE maps colored by expression of selected genes were created using the ggplot2 package. For subpopulation identification, we used the top 500 genes with highest variance to elucidate global differences among single cells. To assess transcriptome similarities in terms of induction of hematopoietic genes in iPSC-derived HSCs, we used 62 hematopoietic genes for t-SNE analysis. GSEA GSEA was performed with the desktop client version (javaGSEA, software is available at the Broad Institute website) with default parameters. RPKM values from the 7F-HSPC were obtained from the RNA seq (described previously). These values were normalized to a terminally differentiated cell (e.g., T-cells or B-cells) and the normalized values were used to rank the most differentially expressed genes. These differentially expressed genes were used to run GSEA with gene sets obtained from mSigDB (KEGG, Hallmark, immunological, transcription factors and chemical and genetic perturbations gene sets were used). In addition, gene sets specific to progenitors, cord blood or fetal-liver HSC were obtained from previous reports[73][23]. FDR <0.25 with a p-value of <0.05 was considered significant.

Lentiviral Integration Detection by Ligation-Mediated PCR and Next-Generation Sequencing Either CD33+ myeloid, CD19+ B- and CD3+ T-cells were isolated from BM from HE-injected NSG mice. Genomic DNA was purified with QIAamp DNA Micro kit (QIAGEN). Ligation-mediated PCR-based detection of lentiviral integration sites was done with Lenti-X Integration Site Analysis Kit (Clontech) according to manufacture's instruction. Sequencing-based detection (Integ-seq) was done following a previous report[74].

Results

Cell identity is defined by gene regulatory networks that are governed by transcription factors (TFs)[10,11]. By supplying TFs that drive hematopoietic gene regulatory networks, several groups have generated hematopoietic stem and progenitor cells from sources as diverse as fibroblasts, endothelial cells, and differentiated blood cells[12-18]. In a prior study, we screened a set of 9 HSC-specific TFs for their potential to induce in vitro hematopoietic colony forming activity and in vivo engraftment from hPSC-derived myeloid cells, and isolated a set of five TFs (HoxA9, ERG, RORA, SOX4, and MYB) that promoted short-term engraftment of erythroid and myeloid cells, but did not achieve long-term multilineage hematopoiesis[17]. Recent approaches have recapitulated HE differentiation from hPSCs to generate cells with myeloid and T cell hematopoietic potential in vitro[19-21]; however, few, if any, cells capable of engrafting irradiated murine hosts were generated.

We adapted a protocol to derive HE from hPSCs and verified its hematopoietic potential[20]. We isolated HE (characterized by these markers: FLK1+CD34+CD43-CD235A-) at day 8 of embryoid body (EB) formation (data not shown), and upon further culture supplemented with hematopoietic cytokines observed the endothelial to hematopoietic transition. Consistent with previous reports[19,20], we documented a decrease in expression of endothelial genes (YAP, FOXC1, COUPTFII), an increase in levels of hematopoietic lineage genes (RUNX1, MYB, GATA2, SCL), and concomitant emergence of CD34+CD45+ hematopoietic cells (data not shown). However, multiple attempts to engraft irradiated immune deficient recipients with these cultured cells failed.

Figure 1C:
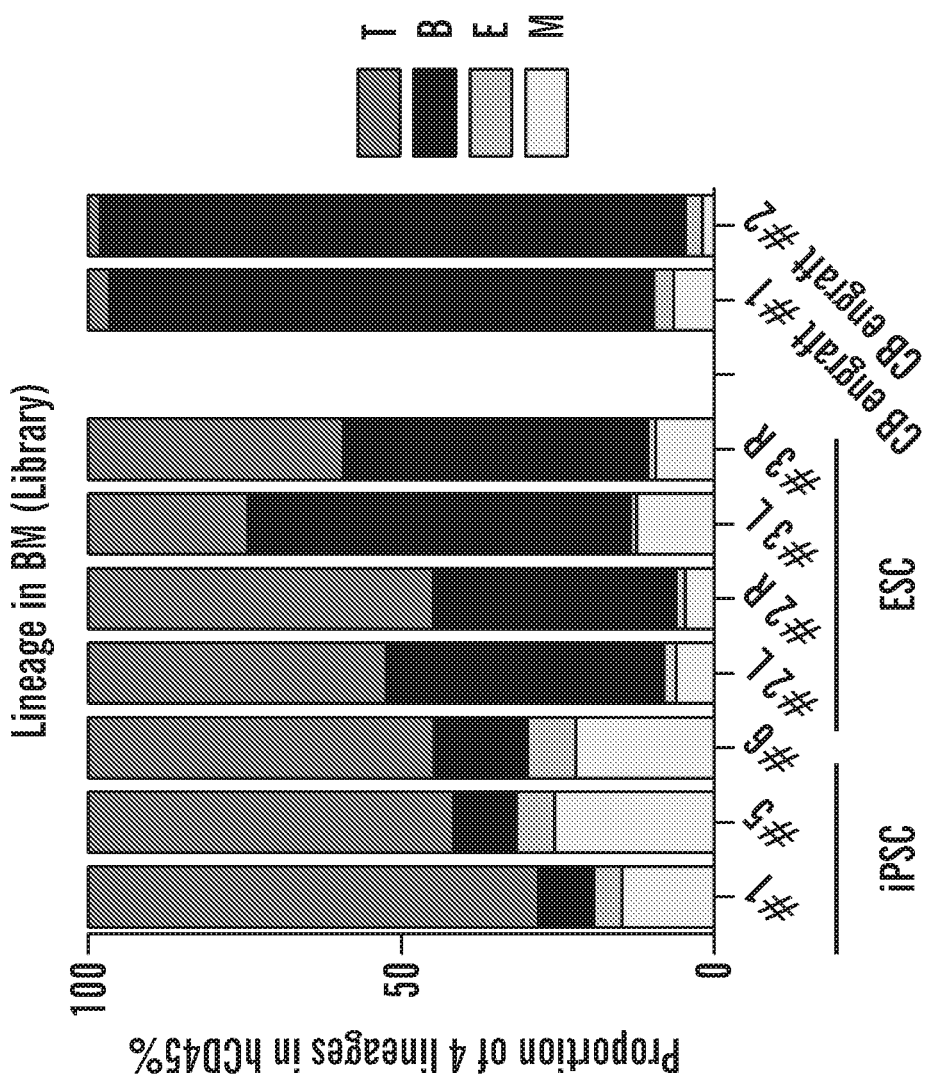
Figure 1B:
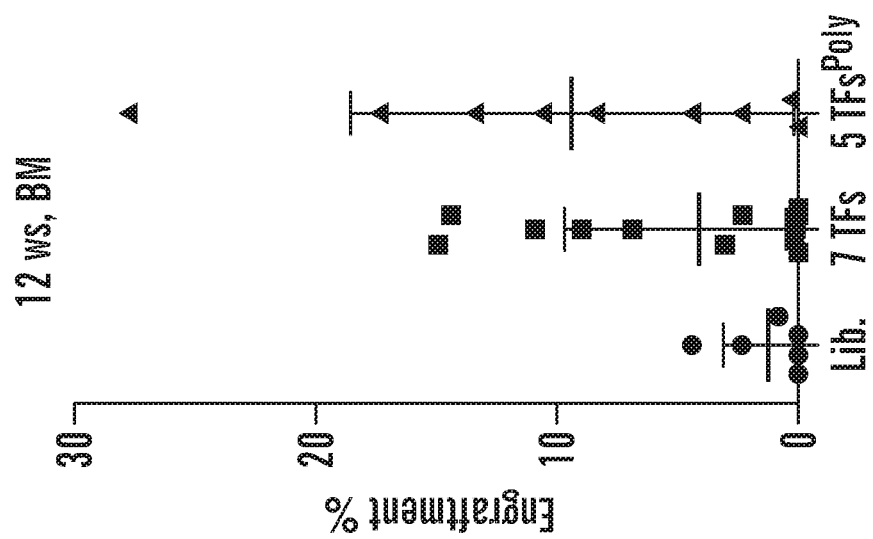
Figure 4:
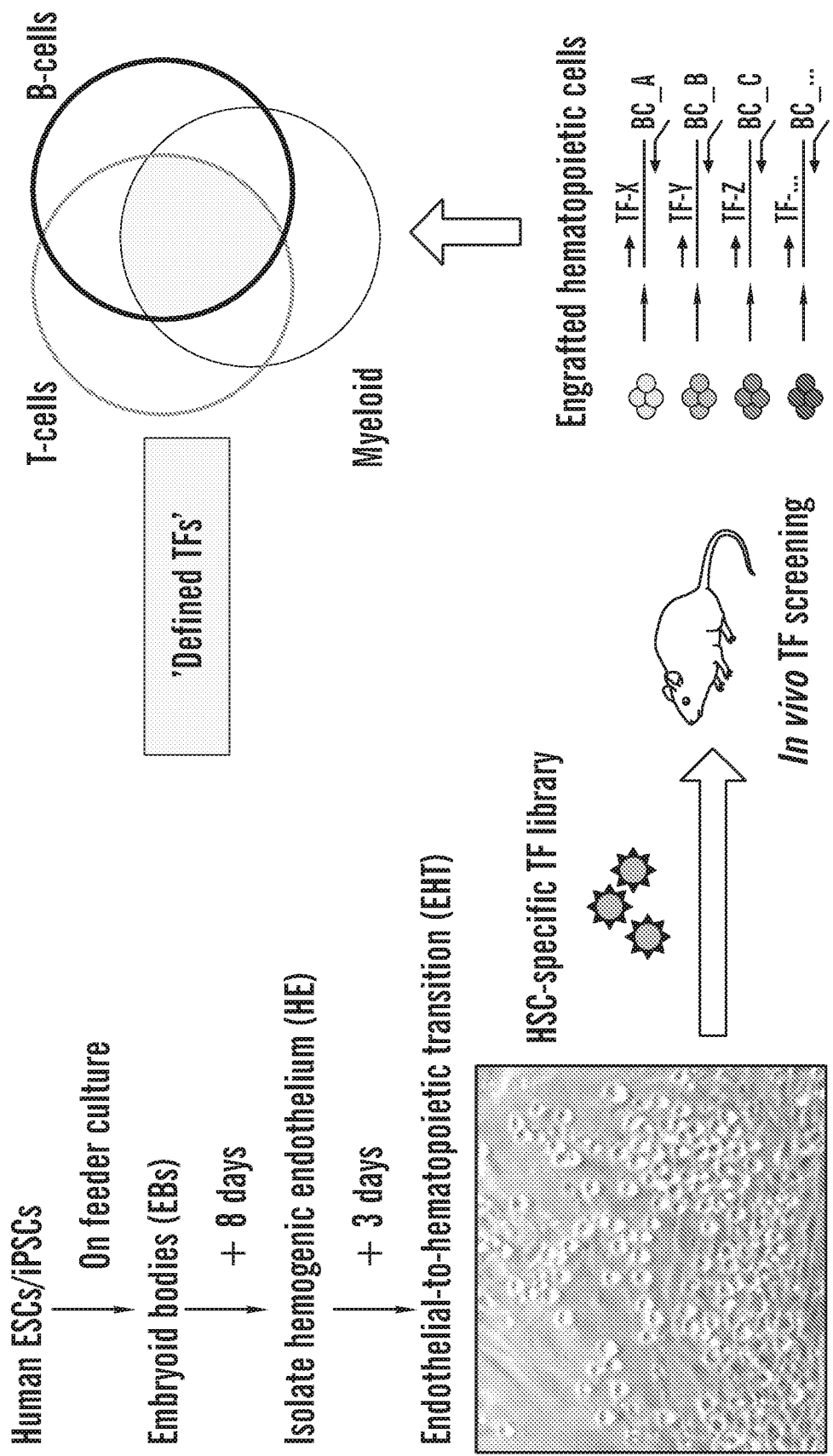
FIG. 4. Scheme of in vivo screening of transcription factors (TFs) to confer functional hematopoiesis in hPSC-derived hemogenicendothelium (HE). Human ESCs/iPSCswere differentiated to embryoidbodies (EBs) by cytokines for specification of hemogenicendothelium (HE). At day 8 time point, CD34+FLK1+CD43-CD235A-HE was isolated, and cultured in endothelial-to-hematopoietic transition (EHT) media for additional 3 days. Library of HSC-specific TFs was induced in HE via lentivirus and injected to sub-lethally irradiated immunodeficientNSG mice intrafemoraly. Engrafted hematopoietic cells were isolated and analyzed by genomic PCR to detect integrated TFs (positive hits).

We hypothesized that introduction of HSC-specific TFs would endow hPSC-derived HE with the potential to engraft multi-lineage hematopoiesis in vivo. We queried the HE by CellNet, a cell-type classification algorithm that compares in vitro derived cells against a panel of comparator cell types[22]. HE was classified as predominantly endothelium with partial identity to hematopoietic stem and progenitor cells (HSPCs; data not shown). To identify TFs likely to specify HSPC fate, we reasoned that functionally relevant TFs would be evolutionarily conserved. Thus, we used two independent mouse[23,24] and two human[25,26] datasets to select 12 TFs enriched in fetal liver-HSCs (FL-HSCs) relative to HE (data not shown), and selected other candidates from prior reports that used TFs to covert endothelial cells", hPSC-derived myeloid cells[17], or committed lymphoid cells[12] to hematopoietic progenitor cells. For the data set, comparison of the expression profile of HSC-specific TFs between HE (CD34+ FLK1+CD43-CD235A-) vs FL-HSCs (CD34+CD38-CD90+CD45+) were made. 12 HSC-specific TFs were enriched in FL-HSCs and downregulated in HE. Those TFs were cloned to Dox-inducible lentiviral vector. The expression level of SOX17, a marker of HE, was 2.4-fold higher in HE (N=7) than FL-HSCs (N=10). * P<0.001. All together, we assembled a library of 26 TFs, which we cloned into a doxycycline-inducible lentiviral vector (FIG. 1A). We infected the library into HE at day 3 of endothelial-to-hematopoietic transition (EHT) culture (efficiency was >50%; FIGS. 1A and 4). We injected the transduced cells intrafemorally into sublethally irradiated immune-deficient NOD/SCID/Gamma (NSG) mice. Mice received doxycycline in their drinking water and diet for two weeks to induce transgene expression[12], after which doxycycline was withdrawn. We observed human CD45+ cells in peripheral blood of injected mice up to 14 weeks, indicating long-term hematopoietic engraftment (FIG. 1B). Examination of BM and thymus demonstrated the presence of human erythroid (GLY-A+), myeloid (CD33+), B (CD19+) and T-cells (CD3+) (FIG. 1C). When human cord blood (CB)-HSCs engraft in NSG mice, a predominance of B-cells over T cells is typical[27]. Analysis of BM from 3 of 6 recipients engrafted with hiPSC-derived HE and 2 of 5 recipients engrafted with hESC-derived HE at 10-14 weeks showed notable reconstitution of T-cells and/or B-cells, comprising 46±20% and 37±9.7% proportion of human grafts, compared with CB-HSC derived grafts, in which B-cells comprised 86±11% of engrafted human cells (FIG. 1C). Intrafemoral injection of HSCs into one femur repopulates the contralateral femur through expansion and homing of HSCs[28]. Notably, following unilateral intrafemoral injection of transduced HE, we observed engraftment in both femurs. Engraftment of human CD45+ cells in BM averaged 2.5±3.4% from transduced HE, compared with 46±18% from CB-HSCs. To confirm the hPSC origin of our engrafted cells, we demonstrated by SNP array genotyping that human CD45+ cells collected from peripheral blood were identical to the input hPSCs (data not shown). Together, these results demonstrate that infection with a 26-TF library enables multi-lineage hematopoietic engraftment from hPSC-derived HE.

Figure 5:
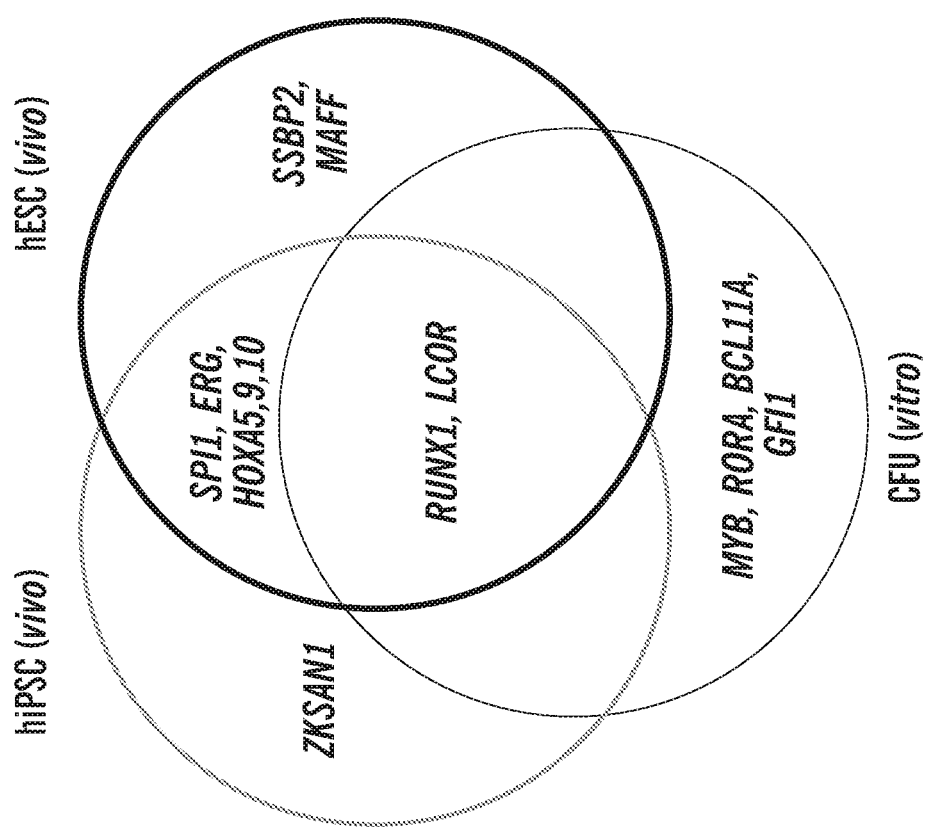
FIG. 5. Venn diagram of TFs that conferred in vivo engraftment and in vitro CFU on PSC-HE.

We then determined which of the 26 TFs could be detected in the engrafted human cells by PCR amplification in sorted populations of CD33+ myeloid, CD19+ B cell, and CD3+ T cells. 7 TFs (ERG, HOXA5, HOXA9, HOXA10, LCOR, RUNX1, SPI1) were consistently detected in myeloid, B- and T-cells of five engrafted recipients, indicating that these factors conferred multipotency. FIG. 5 shows the Venn diagram of expression profile of TFs during hematopoietic ontogeny. ZKSCAN1, SSBP2, MAFF, DACH1, and SOX4 were detected in certain infected cultures but not consistently across all animals, perhaps reflecting their potential to enhance engraftment under some experimental conditions, or perhaps indicating that these genes are passengers.

We next determined whether the 7 common TFs were sufficient to support multilineage engraftment of HE in vivo. We transduced HE with these 7 TFs, injected cells intrafemorally into sublethally irradiated NSG mice, and treated with doxycycline for 2 weeks. Chimerism of human CD45+ in murine BM at 8 weeks was 1.9±1.8% for library transduced cells, 12±5.1% for cells transduced with the defined 7 TFs, and 43±4.2% for CB-HSCs (FIGS. 1B and 1D), reflecting considerably enhanced engraftment potential for the 7 TFs. We sought to determine the minimal combination of TFs required for multilineage engraftment by a factor-minus-one (FMO) approach. Exclusion of individual factors did not ablate engraftment, though RUNX1, ERG, LCOR, HOXA5 or HOXA9 omission reduced chimerism in BM most significantly at 8 weeks (FIG. 2B). These data indicate that at a minimum, RUNX1, ERG, LCOR, HOXA5 and HOXA9 facilitate optimal engraftment.

Figure 1D:
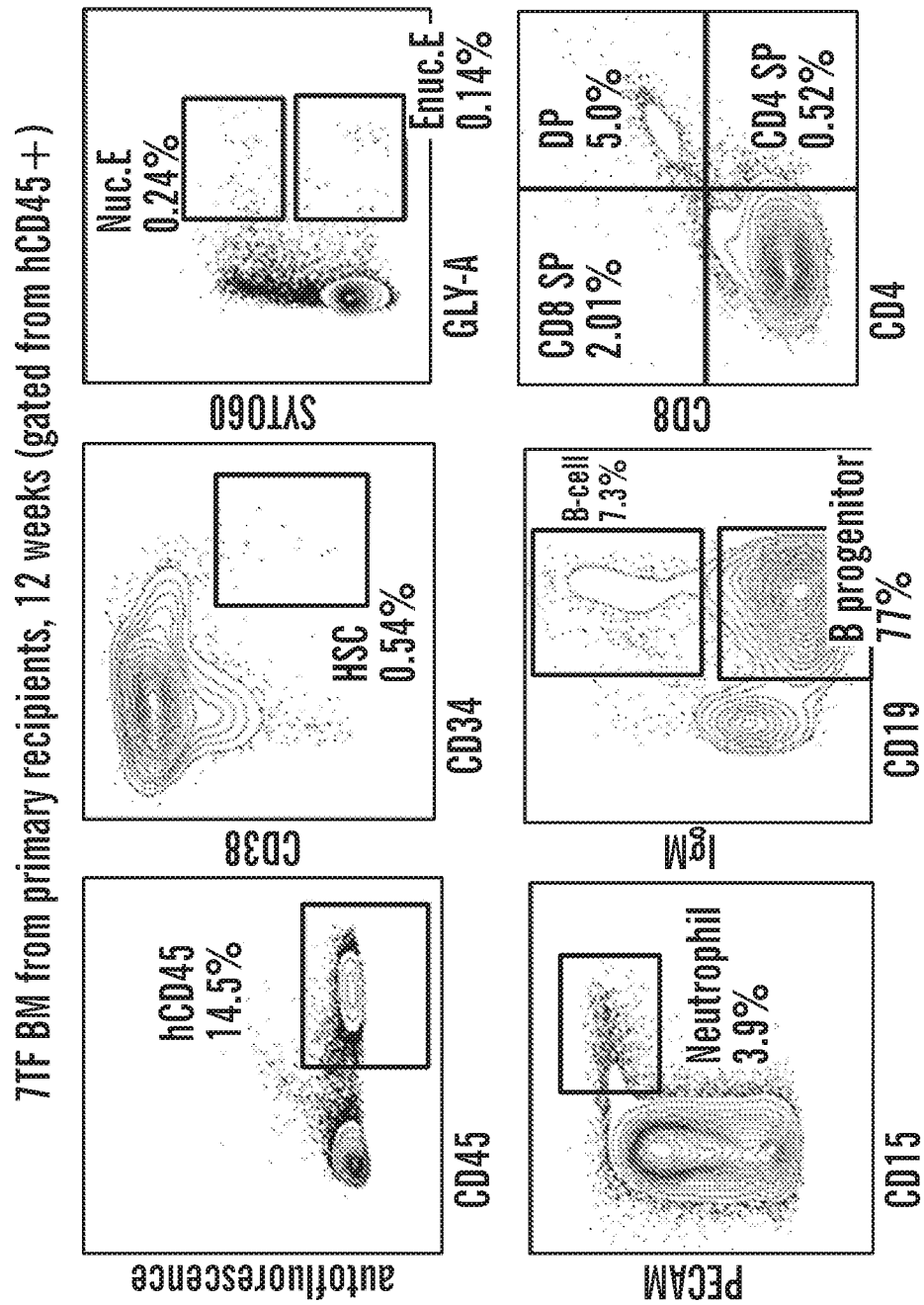
Figure 1E:
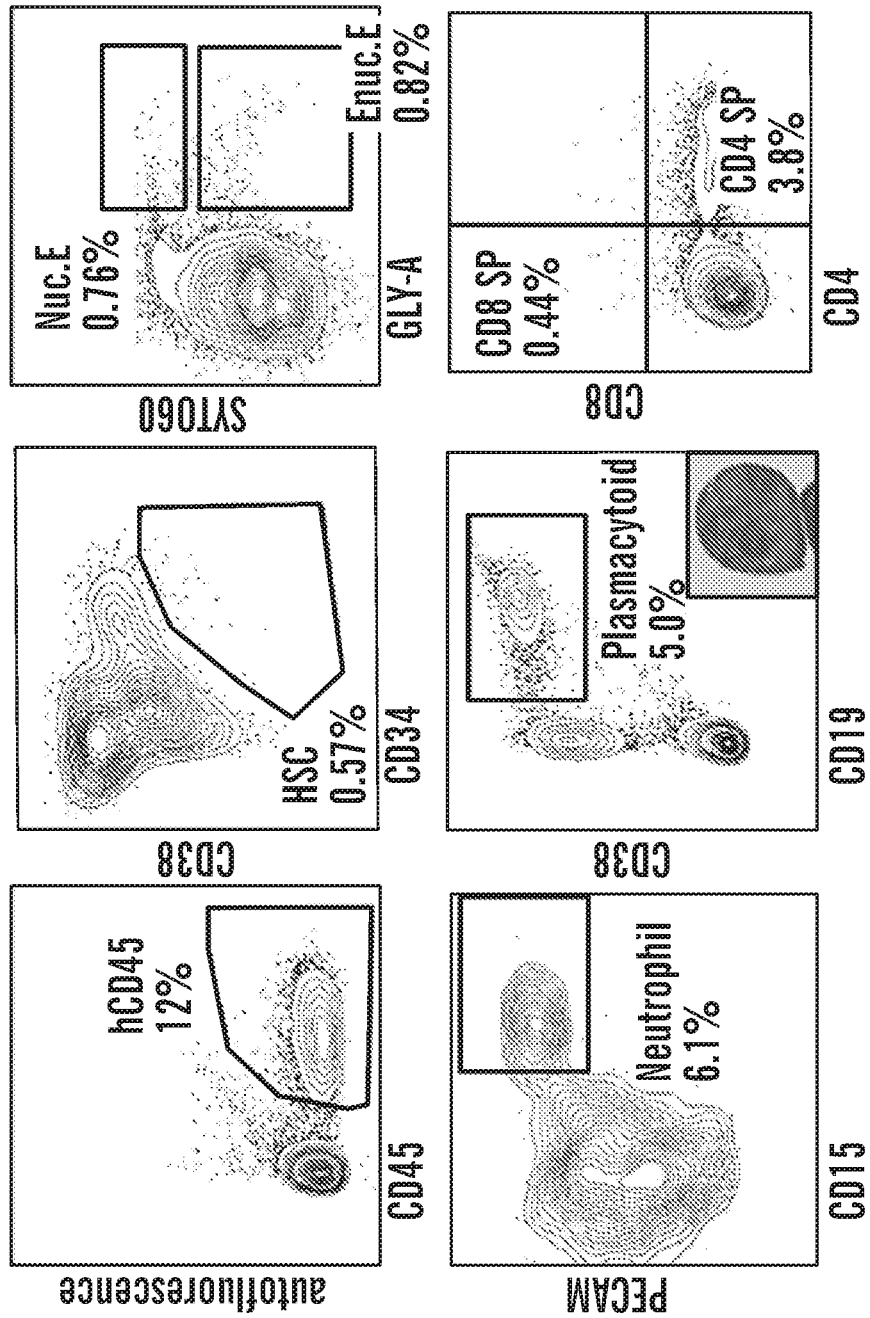
Figures 1F, 2A:
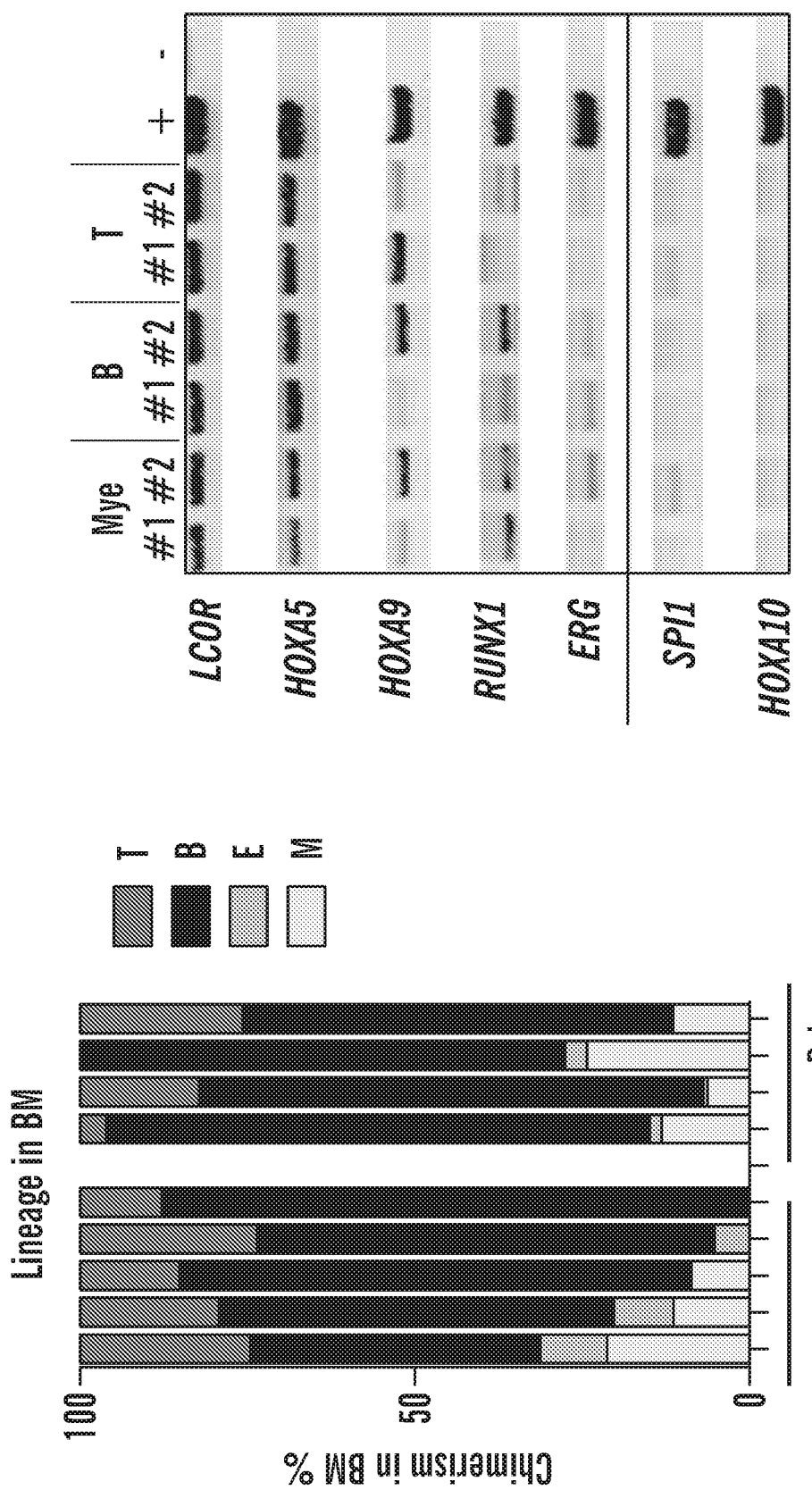
FIGS. 2A-2G collectively demonstrate the detection of TFs that confer multi-lineage engraftment.
Figure 2B:
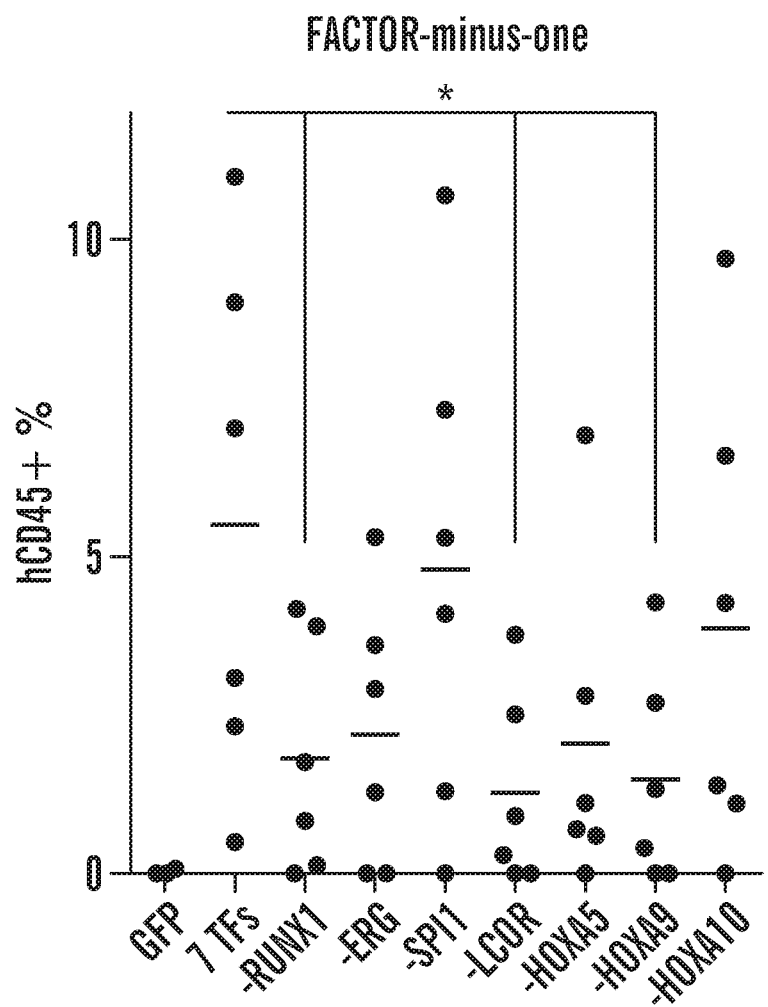
Figure 2C:
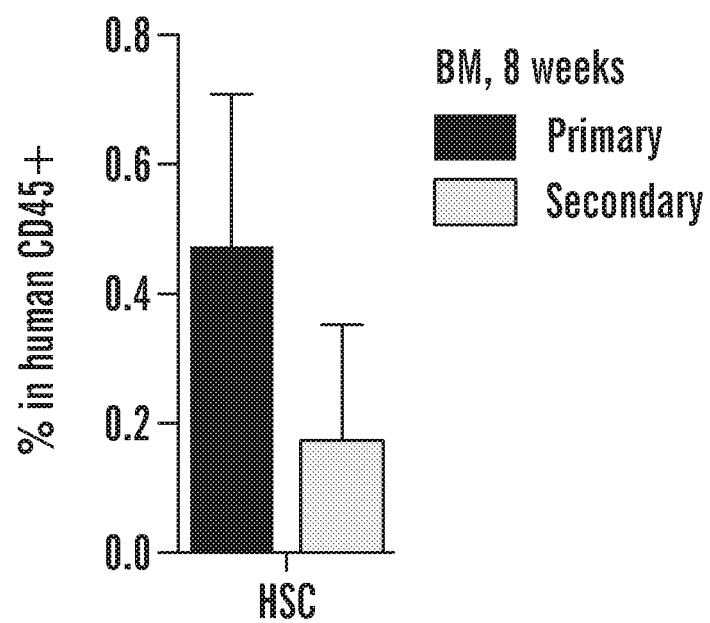
Figure 2D:
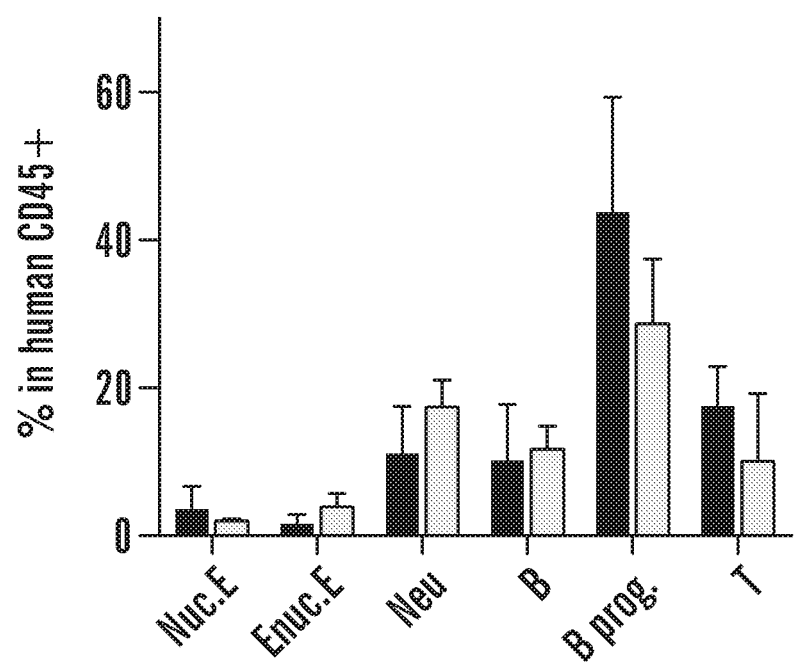
Figure 2E:
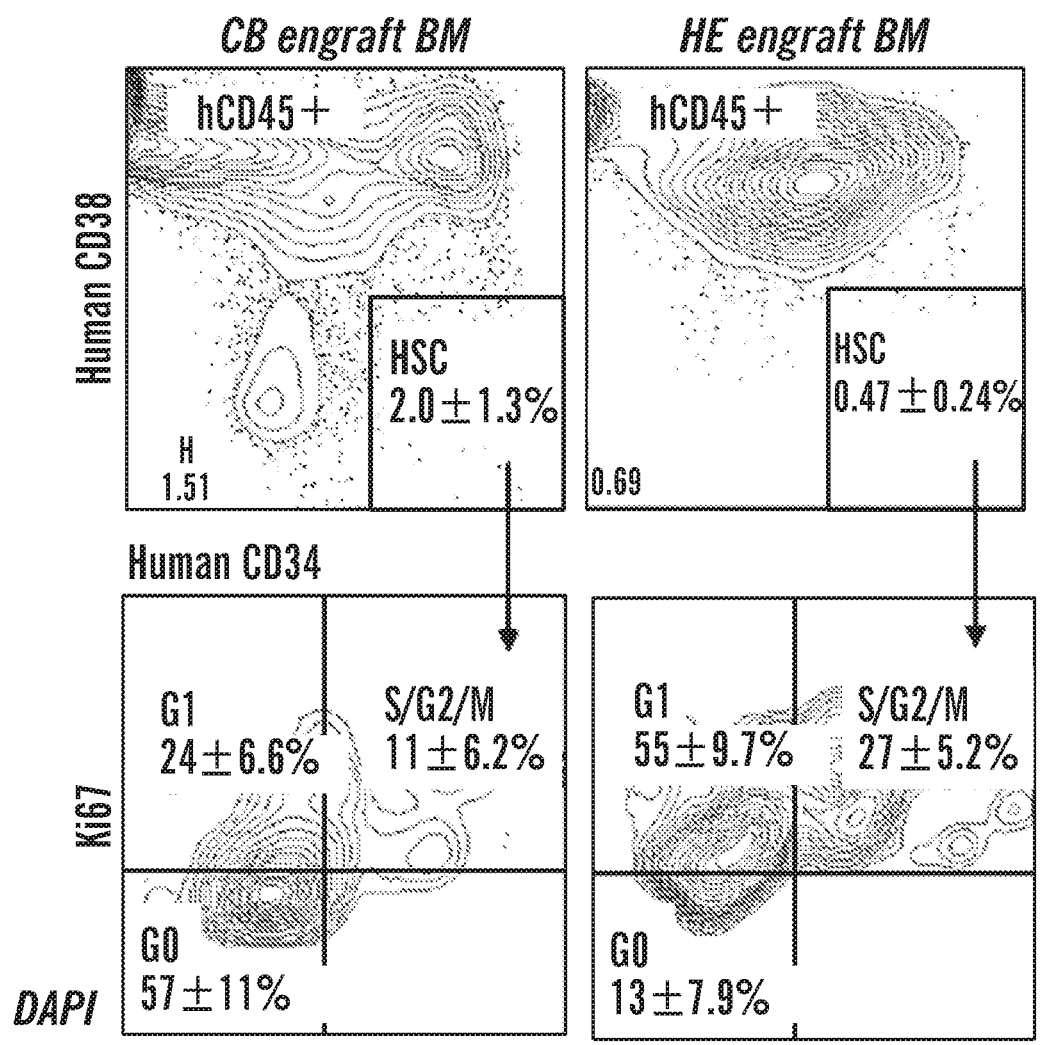

We monitored mice engrafted with HE transduced with the defined 7 TFs until 12 weeks. 2 out of 5 recipients had multi-lineage engraftment with erythroid (GLY-A+), myeloid (CD33+), B-cells (CD19+) and T-cells (CD3+) (FIGS. 1D and 1F). The 3 other recipients had both B-cells and T-cells and either erythroid or myeloid cells (FIG. 1F). We next validated the self-renewal capacity of HE-derived cells by secondary transplantation. 2 out of 5 recipients engrafted with multilineage erythroid, neutrophils, B-cells and T-cells at 8 weeks (FIG. 2C). The percentage of phenotypic HSCs (CD34+CD38−) was lower in secondary than primary mice, indicating depletion of the HSC-like population over time, however, multilineage engrafts were still observed over 14 weeks (FIG. 2D).

To determine which of 7 TFs were consistently isolated in multiple lineages of secondary engrafted mice, we performed PCR amplification of myeloid, B and T cells from 2 mice and detected LCOR, HOXA5, HOXA9 and RUNX1 in every lineage, while ERG was noted in only myeloid and B-cells. SPI1 and HOXA10 appeared dispensable (FIG. 2A). We then investigated if ERG, LCOR, HOXA5, HOXA9 and RUNX1 are essential to confer functional hematopoiesis on iPS-HE. 5 factors (LCOR-HOXA5-HOXA9/RUNX1-ERG) were induced by polycistronic lentiviral vectors and conferred multilineage erythroid, neutrophils, B-cells (including plasmacytoid lymphocytes) and T-cells at 12 weeks (FIGS. 1E and 1F).

The RUNX1 TF is well known to facilitate EHT[29]. We determined if defined TFs enhance EHT using the RUNX1+ 24 enhancer-tdTomato reporter that activates during hematopoietic cell emergence from HE[30]. Upon expression of 7 TFs in HE, the reporter was induced 2.4-fold compared to control, correlating with an increase in hematopoietic genes (MYB, HDAC1, GATA2) (data not shown). These data suggest that the 7 TFs we have identified drive hematopoiesis in part through facilitating Runx1-mediated EHT.

A previous report demonstrated the induction of engraftable progenitor cells from hESCs, however, it is uncertain if myeloid and lymphoid progeny came from monoclonal origin that is feature of stem cells, or distinctly committed progenitor cells[18]. We then determined whether the myeloid and lymphoid progeny of the iPS-derived HE transduced with the 7 TFs were of monoclonal origin by comparing lentiviral integration patterns. We isolated genomic DNA from myeloid (CD33+), B-(CD19+) and T-cells (CD3+) from BM and thymus at 10 weeks post transplantation, followed by adaptor-ligation PCR to detect lentiviral integration sequences. Common integration sequences were detected in myeloid, B-cells, and T-cells in each individual recipient (data not shown), consistent with a monoclonal origin of at least some of the cells. Remarkably, T-cells had several unique minor integrations indicating the presence of a diverse human T-cell pool in engrafted NSG, as reported previously[31]. These data demonstrate that in vivo screening identified a core set of between 5-7 TFs that induce HSC-like cells capable of repopulating irradiated primary and secondary mice with multi-lineage hematopoiesis.

Figure 2F:
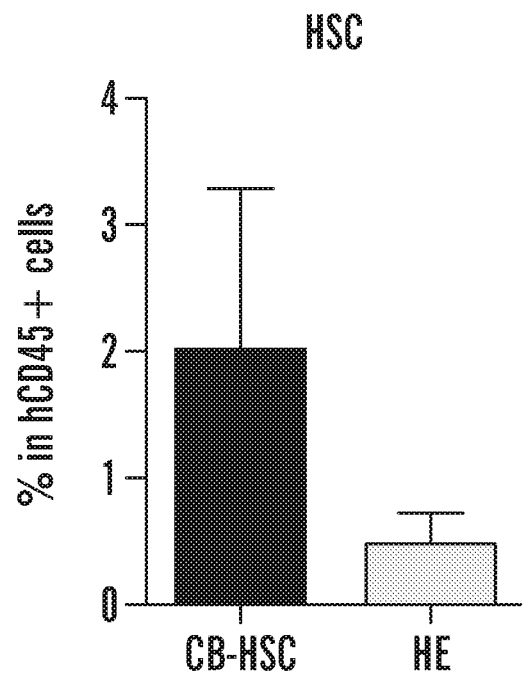
Figure 2G:
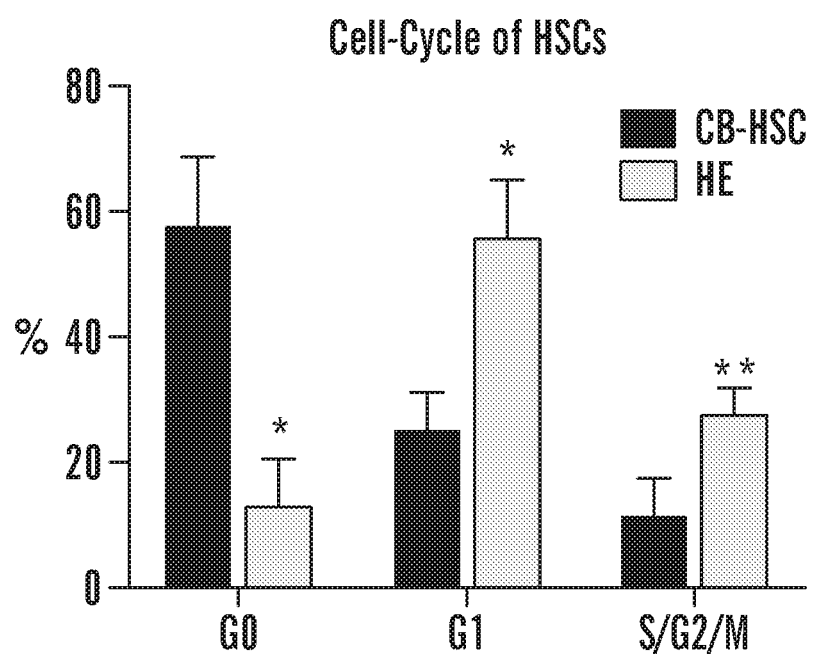

Although some recipient mice manifest clonal multi-lineage hematopoiesis indicative of reconstitution from HSC-like cells, secondary mice showed a reduced frequency of CD34+38− phenotypic HSCs. The frequency of phenotypic HSCs in BM was 2.0% (CB-HSC engrafted group) versus 0.47% (HE engrafted group) (FIG. 2F). The cycling state of 7 TF HSPCs (based on Ki67 expression) was significantly higher than that of CB-HSCs in secondary recipients (FIG. 2G). Human CD45+ cells recovered from engrafted BM revealed residual transgene expression despite cessation of doxyxcyline (data not shown). Interestingly, LCoR has been reported to be a negative regulator of p21 expression[32], and p21-deficient HSCs are known to undergo exhaustion due to persistent cycling[33]. Thus, we speculate that trace levels of residual transgene expression could compromise the long term cycling of the HSPC-like cells.

Figure 3A:
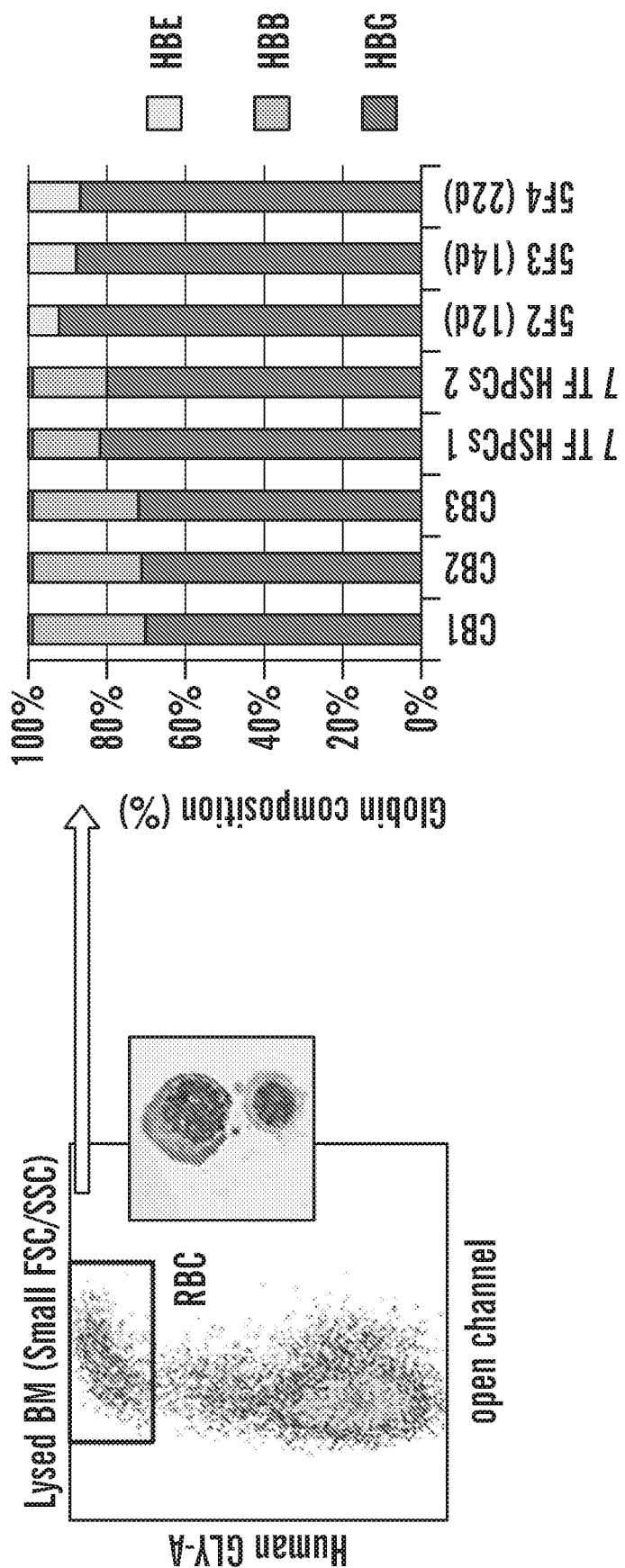
FIGS. 3A-3H collectively demonstrate the functional characterization of terminally differentiated cells.
Figure 3B:
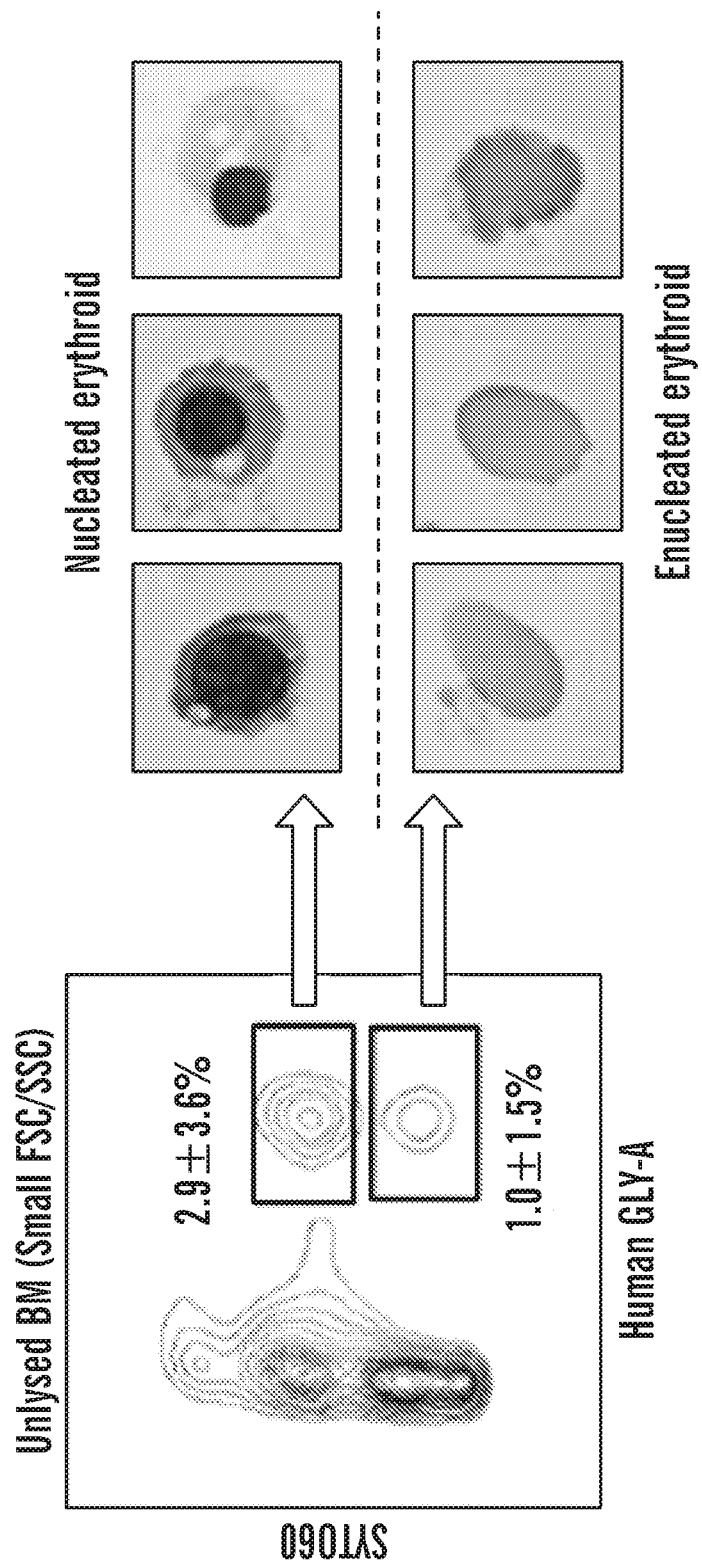
Figures 3C, 3D:
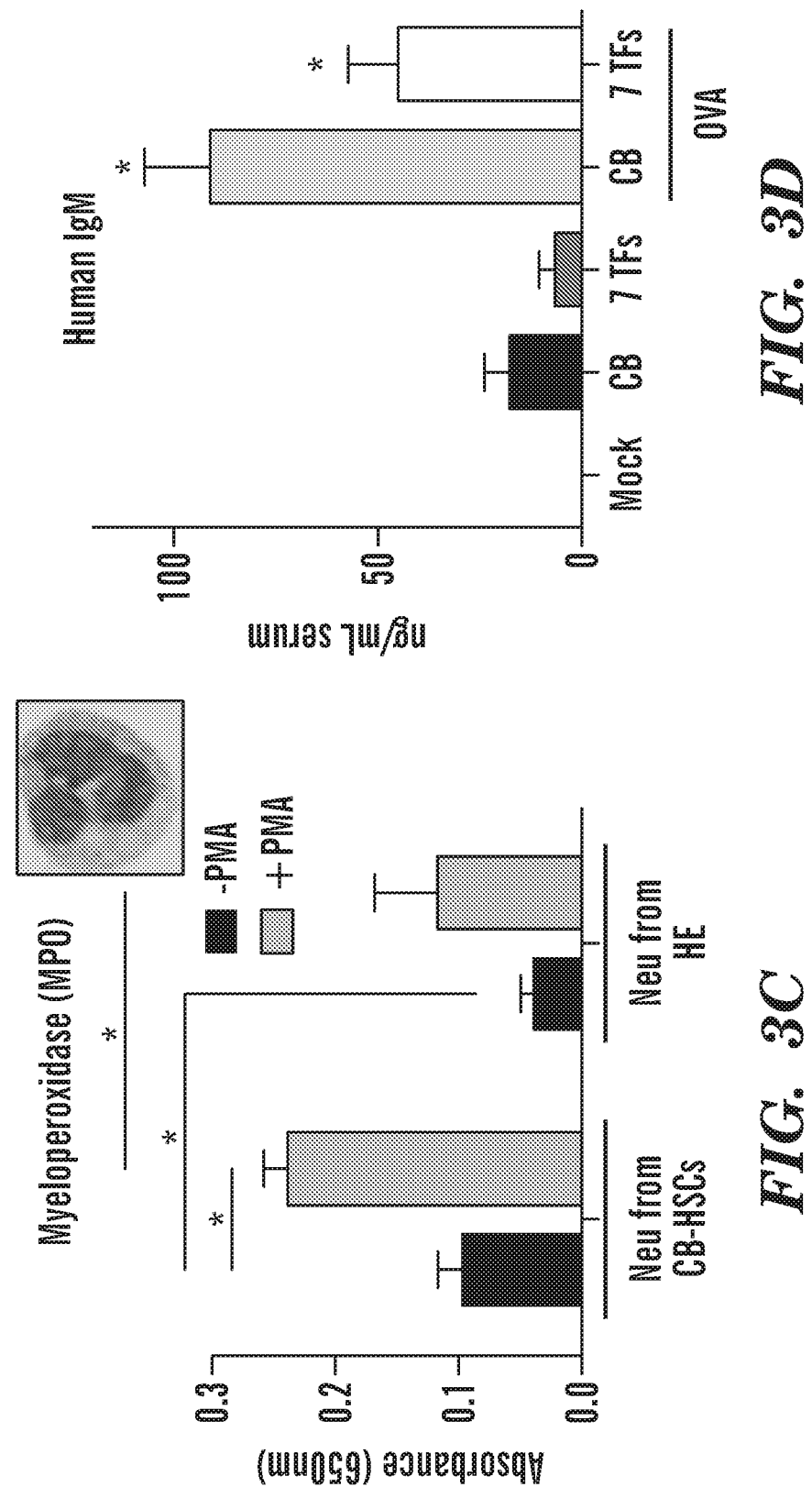
Figure 3F:
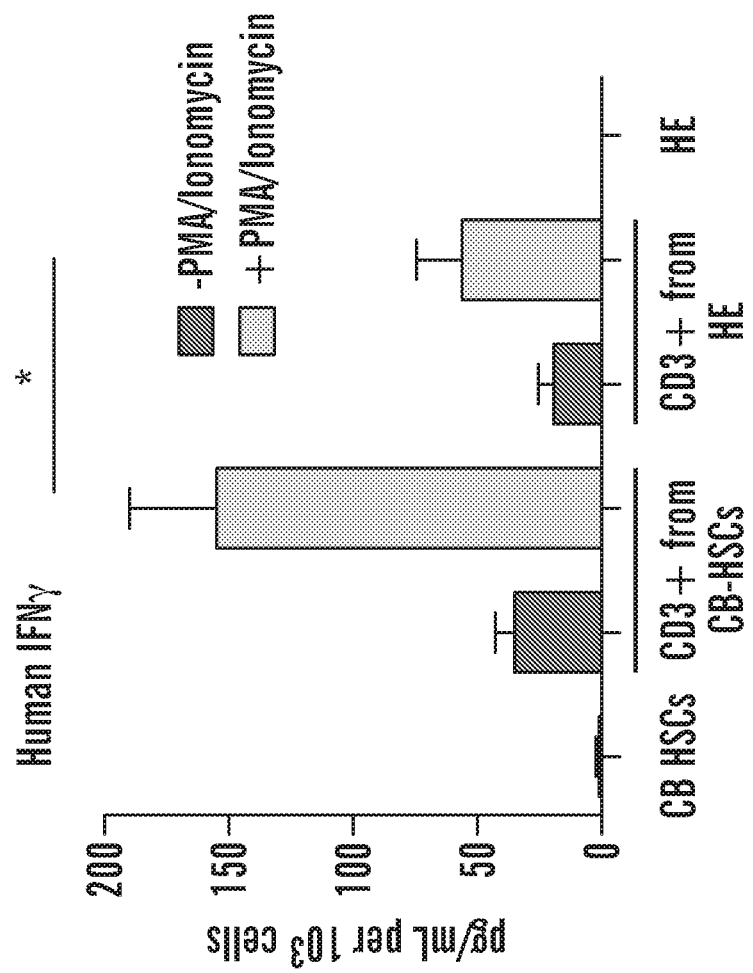
Figure 3E:
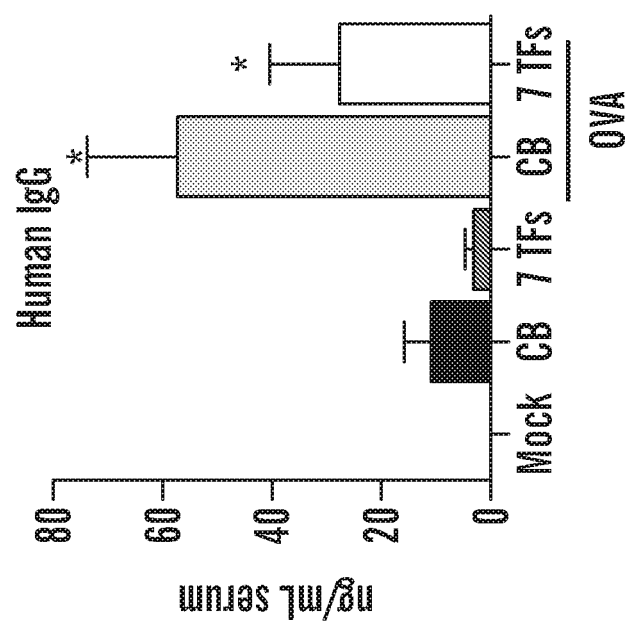
Figure 3G:
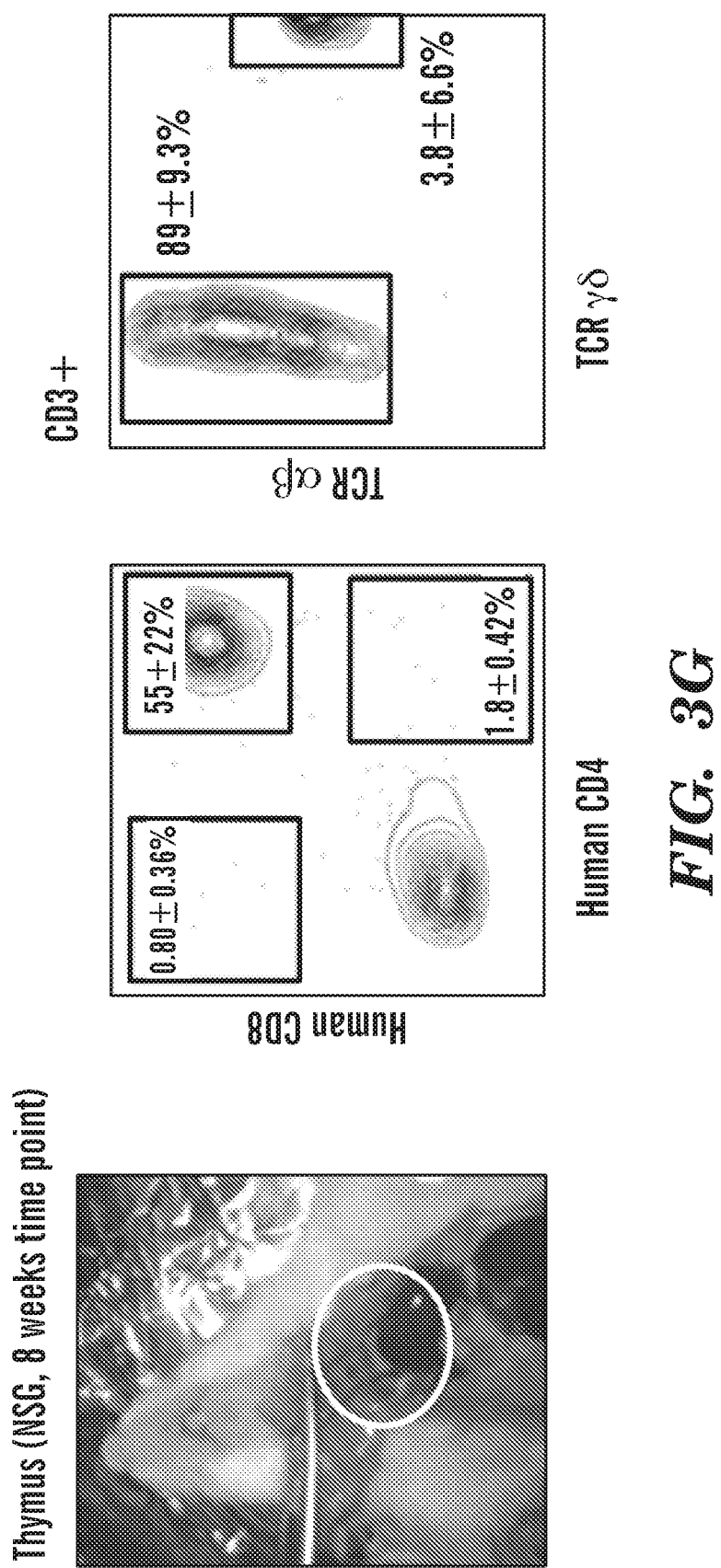
Figure 3H:
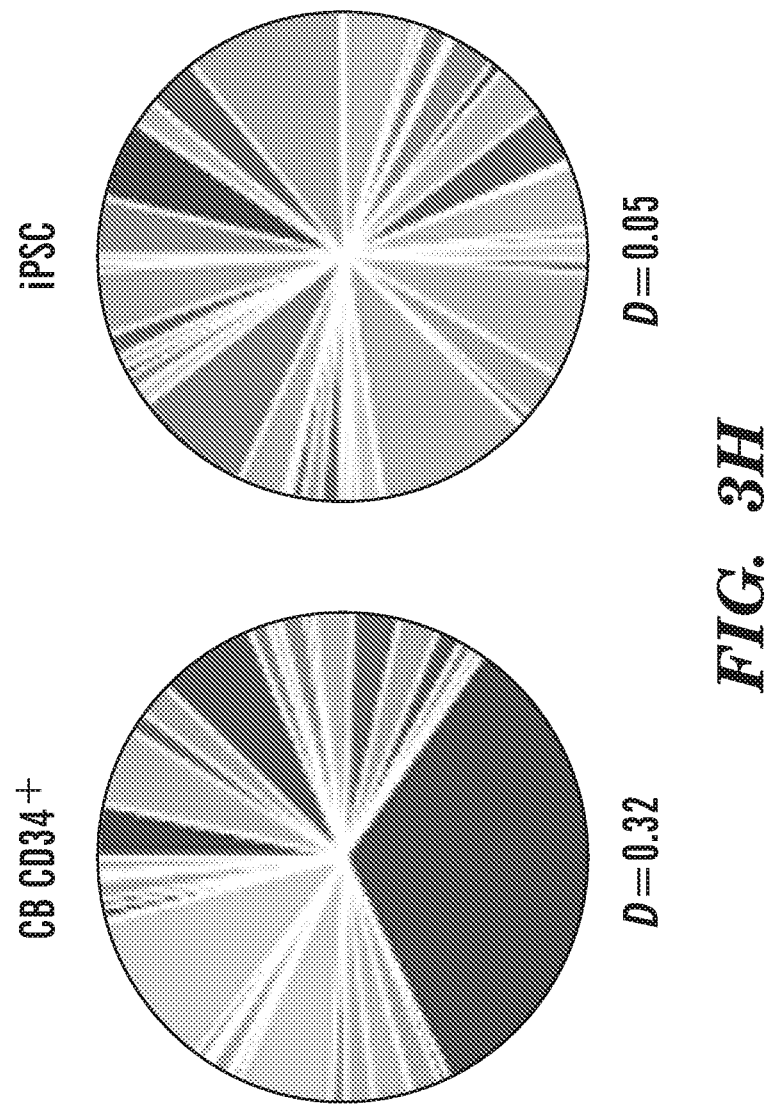

We examined erythroid, myeloid, and lymphoid cells recovered from engrafted mice, and compared their functional properties to CB-HSC-derived cells. Definitive erythropoiesis is characterized by globin switching and enucleation[34][35]. Most erythroid cells generated from hPSCs express embryonic and fetal globins and retain nuclei[17]. The human erythroid cells recovered from engrafted mice lacked expression of embryonic HBE, and expressed fetal HBG and adult HBB at levels comparable to CFU-E from human CB (FIG. 3A). Remarkably, ¼ of human GLY-A+ cells derived from the 7TF HSPCs were enucleated (FIG. 3B). Human myeloid cells in NSG recipients respond to cytokine stimuli by activation of myeloperoxidase (MPO)[36]. We isolated CD45+CD15+ PECAM+ neutrophils from engrafted BM at 8 weeks, and compared MPO production to engrafted CB-derived cells. PMA stimulation enhanced the production of MPO 3.0-fold relative to unstimulated neutrophils (FIG. 3C). Bona fide human HSCs generate functional T- and B-cells in NSG mice[27]. IgM and IgG antibody could be detected in the serum of NSG mice engrafted with 7 TF HSPCs, indicating the cooperative activity of T and B cells in mediating immunoglobulin class switching, secretion and boosted by Ovalbumin (OVA) (FIGS. 3D and 3E). We isolated mature CD3+ T-cells from BM and measured interferon γ (IFNγ) production. Notably, this CD3+ population expressed CD4, and not CD8. PMA/Ionomycin (PMAI)-stimulation enhanced IFNγ production 3.0-fold in 7 TF CD3+ cells vs 4.4-fold in CB-derived CD3+(FIG. 3F). T-cells develop from CD4−CD8− double-negative cells followed by CD4+CD8+ double-positive cells that express surface TCR/CD3 complex, which differentiate to either CD4 or CD8 single-positive T cells in thymus, which migrate to blood and BM37. At 8 weeks, 7 TF HSPC-derived thymocytes were predominantly CD4+CD8+ (55±22%), with few CD4+CD8− (1.8±0.42%) and CD4-CD8+(0.80±0.36%). Human CD3+ T-cells differentiated from HSCs in NSG possess either TCRαβ (>60%) or TCRγδ (<30%)[27], consistent with our observation that 7 TF HSPC-derived grafts produced both TCRαβ (89±9.3%) and TCRγδ (3.8±6.6%) cells (FIG. 3G). Development of a diverse population of antigen-specific T cells requires rearrangement of germline-encoded TCR genes", largely mediated by the complementarity determining region 3 (CDR3) within variable (V) gene segments of the TCRA and TCRB genes[39]. To determine clonotype diversity, we profiled the CDR3 region of TCRB on CD3+ T-cells in reconstituted mice using next generation sequencing. We observed a high degree of combinatorial diversity in the V gene segment in CD3+ T-cells isolated from either CB-engrafted NSG or 7 TF HSPC-engrafted NSG mice with the CDR3 length following a standard Gaussian distribution (FIG. 3H).

The generation of functional HSC-like cells from PSCs has been a long sought goal in hematology research. By directed differentiation of hPSCs to HE followed by in vivo screening of TFs for hematopoietic progenitor specification, we identified 7 TFs that together confer HSC-like engraftment, self-renewal and multilineage capacity. Considerable work remains to establish engraftment with transgene-free cells, and to achieve stable, long-term multi-lineage hematopoietic chimerism in humanized mice. Such a system will facilitate modeling a multitude of genetic blood disorders that are not faithfully recapitulated in genetically engineered murine models, and for which adequate marrow samples are not readily obtained, as for patients with bone marrow failure syndromes.

Combinations of TFs have been introduced into differentiated blood cells[12][17] to endow HSC-like properties in a murine system[12], but transplantable human HSCs with multilineage capacity have to date not been derived from hPSCs. Recent advances in the directed differentiation of PSCs to definitive HE have provided a supportive context for screening of HSC-specifying TFs. Each of the identified TFs in our study plays a role in HSC development, maintenance of long-term HSCs, or lineage commitment. RUNX1 is essential for hematopoietic commitment of HE and can convert endothelial cells to hematopoietic progenitor cells[13,40,41]. LCOR, a component of histone deacetylation complex, is mutated in B-cell lymphoma, suggesting a role in B-lymphopoiesis[42,43], but this factor has not previously been implicated in HSC functions and its role remains to be defined. SPI1 (also known as PU.1) is required for hematopoietic progenitor cell emergence and regulates myeloid specification[44,45,46]. HOX family members have been reproducibly implicated in hematopoiesis across species[17,47,48]. HOXA9 is the key homeotic gene that defines HSC identity[49,50], interacting with ERG to support HSC renewal during embryogenesis and stress hematopoiesis[51-53], suggesting a basis for the functional cooperation of HOXA9 and ERG in our system. HOXA10 augments induction of erythroid cells from ESCs[54], but appears to be at least partially dispensable in our system. Ectopic expression of HOXA5 induces commitment of HSCs to myeloid lineages[55]. HOXA5 is a transcriptional target of Notch signaling in T-cell progenitors along with HOXA9 and HOXA10, consistent with a role in T-lymphopoiesis[56]. These factors share binding sites in the genome and cooperate to recruit chromatin modulators (e.g. RUNX1 and HOXA families)[53,57] to induce and maintain HSPCs.

Our FMO approach to the defined 7 TFs indicated that they are part of a common gene regulatory network with some redundancy, as exclusion of individual factors did not fully abrogate engraftment of HE. The possibility remains that 7 TF HSPCs are predominantly fetal as shown in hESC-derived hematopoietic cells in a previous study[58], supported by their rapid cycling state, and predominance of CD4+CD8+ T cells in the thymus.

Our study suggests that we are ever closer to realizing the potential of derivation of HSC-like cells from renewable sources like pluripotent stem cells. Such cells, when derived from patients with genetic blood disorders, offer considerable promise for modeling human blood disease, for humanizing mice for research applications, and for testing the capacity of gene therapy vectors or pharmacologic agents to restore hematopoietic function. The long term goal remains the derivation of bona fide transgene-free HSCs for applications in research and therapy.

The references cited herein and throughout the specification are incorporated herein by reference.

REFERENCES

1 Wiles, M. V. & Keller, G. Multiple hematopoietic lineages develop from embryonic stem (ES) cells in culture. Development 111, 259-267 (1991).
2 Graf, T. & Enver, T. Forcing cells to change lineages. Nature 462, 587-594, (2009).
3 Dieterlen-Lievre, F. On the origin of haemopoietic stem cells in the avian embryo: an experimental approach. J Embryol Exp Morphol 33, 607-619 (1975).
4 Ivanovs, A. et al. Highly potent human hematopoietic stem cells first emerge in the intraembryonic aorta-gonad-mesonephros region. J Exp Med 208, 2417-2427, (2011).
5 Bertrand, J. Y. et al. Haematopoietic stem cells derive directly from aortic endothelium during development. Nature 464, 108-111, (2010).
6 Boisset, J. C. et al. In vivo imaging of haematopoietic cells emerging from the mouse aortic endothelium. Nature 464, 116-120, (2010).
7 Kissa, K. & Herbomel, P. Blood stem cells emerge from aortic endothelium by a novel type of cell transition. Nature 464, 112-115, (2010).
8 Peeters, M. et al. Ventral embryonic tissues and Hedgehog proteins induce early AGM hematopoietic stem cell development. Development 136, 2613-2621, (2009).
9 Van Handel, B. et al. Scl represses cardiomyogenesis in prospective hemogenic endothelium and endocardium. Cell 150, 590-605, (2012).
10 Gottgens, B. et al. Transcription of the SCL gene in erythroid and CD34 positive primitive myeloid cells is controlled by a complex network of lineage-restricted chromatin-dependent and chromatin-independent regulatory elements. Oncogene 15, 2419-2428, (1997).
11 Phillips, R. L. et al. The genetic program of hematopoietic stem cells. Science 288, 1635-1640 (2000).
12 Riddell, J. et al. Reprogramming committed murine blood cells to induced hematopoietic stem cells with defined factors. Cell 157, 549-564, (2014).
13 Sandler, V. M. et al. Reprogramming human endothelial cells to haematopoietic cells requires vascular induction. Nature 511, 312-318, (2014).
14 Pereira, C. F. et al. Induction of a hemogenic program in mouse fibroblasts. Cell Stem Cell 13, 205-218, (2013).
15 Szabo, E. et al. Direct conversion of human fibroblasts to multilineage blood progenitors. Nature 468, 521-526, (2010).
16 Batta, K., Florkowska, M., Kouskoff, V. & Lacaud, G. Direct reprogramming of murine fibroblasts to hematopoietic progenitor cells. Cell Rep 9, 1871-1884, (2014).
17 Doulatov, S. et al. Induction of multipotential hematopoietic progenitors from human pluripotent stem cells via respecification of lineage-restricted precursors. Cell Stem Cell 13, 459-470, (2013).
18 Gori, J. L. et al. Vascular niche promotes hematopoietic multipotent progenitor formation from pluripotent stem cells. J Clin Invest 125, 1243-1254, (2015).
19 Kennedy, M. et al. T lymphocyte potential marks the emergence of definitive hematopoietic progenitors in human pluripotent stem cell differentiation cultures. Cell Rep 2, 1722-1735, (2012).

20. Ditadi, A. et al. Human definitive haemogenic endothelium and arterial vascular endothelium represent distinct lineages. Nat Cell Biol 17, 580-591, (2015).
21. Elcheva, I. et al. Direct induction of haematoendothelial programs in human pluripotent stem cells by transcriptional regulators. Nat Commun 5, 4372, (2014).
22. Cahan, P. et al. CellNet: network biology applied to stem cell engineering. Cell 158, 903-915, (2014).
23. Chambers, S. M. et al. Hematopoietic fingerprints: an expression database of stem cells and their progeny. Cell Stem Cell 1, 578-591, (2007).
24. Ivanova, N. B. et al. A stem cell molecular signature. Science 298, 601-604, (2002).
25. Doulatov, S. et al. Revised map of the human progenitor hierarchy shows the origin of macrophages and dendritic cells in early lymphoid development. Nat Immunol 11, 585-593, (2010).
26. Novershtern, N. et al. Densely interconnected transcriptional circuits control cell states in human hematopoiesis. Cell 144, 296-309, (2011).
27. Shultz, L. D. et al. Human lymphoid and myeloid cell development in NOD/LtSz-scid IL2R gamma null mice engrafted with mobilized human hemopoietic stem cells. J Immunol 174, 6477-6489 (2005).
28. Zhan, Y. & Zhao, Y. Hematopoietic stem cell transplant in mice by intra-femoral injection. Methods Mol Biol 430, 161-169, (2008).
29. Taoudi, S. et al. ERG dependence distinguishes developmental control of hematopoietic stem cell maintenance from hematopoietic specification. Genes Dev 25, 251-262, (2011).
30. Ferrell, P. I., Xi, J., Ma, C., Adlakha, M. & Kaufman, D. S. The RUNX1+24 enhancer and P1 promoter identify a unique subpopulation of hematopoietic progenitor cells derived from human pluripotent stem cells. Stem Cells 33, 1130-1141, (2015).
31. Brugman, M. H. et al. Development of a diverse human T-cell repertoire despite stringent restriction of hematopoietic clonality in the thymus. Proc Natl Acad Sci USA 112, E6020-6027, (2015).
32. Calderon, M. R. et al. Ligand-dependent corepressor (LCoR) recruitment by Kruppel-like factor 6 (KLF6) regulates expression of the cyclin-dependent kinase inhibitor CDKN1A gene. J Biol Chem 287, 8662-8674, (2012).
33. Cheng, T. et al. Hematopoietic stem cell quiescence maintained by p21cip1/waf1. Science 287, 1804-1808 (2000).
34. Orkin, S. H. Controlling the fetal globin switch in man. Nature 301, 108-109 (1983).
35. Patient, R. K., Elkington, J. A., Kay, R. M. & Williams, J. G. Internal organization of the major adult alpha- and beta-globin genes of X. laevis. Cell 21, 565-573 (1980).
36. Tanaka, S. et al. Development of mature and functional human myeloid subsets in hematopoietic stem cell-engrafted NOD/SCID/IL2rgammaKO mice. J Immunol 188, 6145-6155, (2012).
37. Spits, H. Development of alphabeta T cells in the human thymus. Nat Rev Immunol 2, 760-772, (2002).
38. Alt, F. W. et al. VDJ recombination. Immunol Today 13, 306-314, (1992).
39. Jung, D. & Alt, F. W. Unraveling V(D)J recombination: insights into gene regulation. Cell 116, 299-311 (2004).
40. North, T. E. et al. Runx1 expression marks long-term repopulating hematopoietic stem cells in the midgestation mouse embryo. Immunity 16, 661-672 (2002).
41. Lacaud, G. et al. Runx1 is essential for hematopoietic commitment at the hemangioblast stage of development in vitro. Blood 100, 458-466, (2002).
42. Fernandes, I. et al. Ligand-dependent nuclear receptor corepressor LCoR functions by histone deacetylase-dependent and -independent mechanisms. Mol Cell 11, 139-150 (2003).
43. Chan, F. C. et al. An RCOR1 loss-associated gene expression signature identifies a prognostically significant DLBCL subgroup. Blood 125, 959-966, (2015).
44. Olson, M. C. et al. PU.1 is not essential for early myeloid gene expression but is required for terminal myeloid differentiation. Immunity 3, 703-714 (1995).
45. Ford, A. M. et al. Regulation of the myeloperoxidase enhancer binding proteins Pu1, C-EBP alpha, -beta, and -delta during granulocyte-lineage specification. Proc Natl Acad Sci USA 93, 10838-10843, (1996).
46. Nerlov, C. & Graf, T. PU.1 induces myeloid lineage commitment in multipotent hematopoietic progenitors. Genes Dev 12, 2403-2412, (1998).
47. Sauvageau, G. et al. Overexpression of HOXB4 in hematopoietic cells causes the selective expansion of more primitive populations in vitro and in vivo. Genes Dev 9, 1753-1765, (1995).
48. Antonchuk, J., Sauvageau, G. & Humphries, R. K. HOXB4-induced expansion of adult hematopoietic stem cells ex vivo. Cell 109, 39-45, (2002).
49. Di-Poi, N., Koch, U., Radtke, F. & Duboule, D. Additive and global functions of HoxA cluster genes in mesoderm derivatives. Dev Biol 341, 488-498, (2010).
50. Lawrence, H. J. et al. Loss of expression of the Hoxa-9 homeobox gene impairs the proliferation and repopulating ability of hematopoietic stem cells. Blood 106, 3988-3994, (2005).
51. Ng, A. P. et al. Trisomy of Erg is required for myeloproliferation in a mouse model of Down syndrome. Blood 115, 3966-3969, (2010).
52. Loughran, S. J. et al. The transcription factor Erg is essential for definitive hematopoiesis and the function of adult hematopoietic stem cells. Nat Immunol 9, 810-819, (2008).
53. Huang, Y. et al. Identification and characterization of Hoxa9 binding sites in hematopoietic cells. Blood 119, 388-398, (2012).
54. Ji, J. et al. Brief report: ectopic expression of NUP98-HOXA10 augments erythroid differentiation of human embryonic stem cells. Stem Cells 29, 736-741, (2011).
55. Crooks, G. M. et al. Constitutive HOXA5 expression inhibits erythropoiesis and increases myelopoiesis from human hematopoietic progenitors. Blood 94, 519-528 (1999).
56. Weerkamp, F. et al. Identification of Notch target genes in uncommitted T-cell progenitors: No direct induction of a T-cell specific gene program. Leukemia 20, 1967-1977, (2006).
57. Hu, Z. et al. RUNX1 regulates corepressor interactions of PU.1. Blood 117, 6498-6508, (2011).
58. Salvagiotto, G. et al. Molecular profiling reveals similarities and differences between primitive subsets of hematopoietic cells generated in vitro from human embryonic stem cells and in vivo during embryogenesis. Exp Hematol 36, 1377-1389, (2008).

59 Loh, Y. H. et al. Reprogramming of T cells from human peripheral blood. Cell Stem Cell 7, 15-19, (2010).

60 Park, I. H. et al. Reprogramming of human somatic cells to pluripotency with defined factors. Nature 451, 141-146, (2008).

61 Meerbrey, K. L. et al. The pINDUCER lentiviral toolkit for inducible RNA interference in vitro and in vivo. Proc Natl Acad Sci USA 108, 3665-3670, (2011).

62 Sankaran, V. G. et al. Developmental and species-divergent globin switching are driven by BCL11A. Nature 460, 1093-1097, (2009).

63 Klein, A. M. et al. Droplet barcoding for single-cell transcriptomics applied to embryonic stem cells. Cell 161, 1187-1201, (2015).

64 Serrao, E., Cherepanov, P. & Engelman, A. N. Amplification, Next-generation Sequencing, and Genomic DNA Mapping of Retroviral Integration Sites. J Vis Exp, (2016).

What is claimed is:

1. A method for making human hematopoietic stem cells (HSCs) and hematopoietic stem and progenitor cells (HSPCs) for cellular replacement therapy, the method comprising in vitro transfection of human hemogenic endothelial cells (HE) with an exogenous gene coding copy of each of the following transcription factors ETS-related gene (ERG), Homeobox protein A9 (HOXA9), Homeobox protein A5 (HOXA5), Ligand Dependent Nuclear Receptor Corepressor (LCOR) and Runt Related Transcription Factor 1 (RUNX1),
   wherein the human HE cells are derived from embryoid bodies (EB) produced from human iPSCs or human ESCs,
   wherein the transcription factors are expressed in the transfected human HE cells, thereby producing a population of multilineage human HSCs and HSPCs for cellular replacement therapy.

2. The method of claim 1, further comprising, prior to in vitro transfection, the steps of:
   a. generating embryonic bodies (EB) from human pluripotent stem cells; and
   b. isolating human hemogenic endothelial cells (HE) from the resultant population of EB.

3. The method of claim 2, wherein the EB are generated or induced from human pluripotent stem cells (PSC) by culturing or exposing the PSC to morphogens for about 8 days.

4. The method of claim 3, wherein the population of human PSC is a population of human induced pluripotent stem cells (iPS cells) or human embryonic stem cells (ESC).

5. The method of claim 4, wherein the induced pluripotent stem cells are produced by introducing reprogramming factors OCT4, SOX2, KLF4 and optionally (i) c-MYC or (ii) nanog and LIN28 into human somatic cells.

6. The method of claim 5, wherein the human somatic cells are selected from the group consisting of peripheral blood circulating cells, B lymphocytes (B-cells), T lymphocytes, (T-cells), fibroblasts, and keratinocytes.

7. The method of claim 2, wherein the EBs are:
   a. less than 800 microns in size and are selected;
   b. are compactly adhered to each other and requires trypsin digestion in order to dissociate the cells to individual cells; and/or
   c. are dissociated prior to the isolation of HE.

8. The method of claim 1, wherein the HE are:
   a. isolated immediately from selected and dissociated EB; and/or
   b. FLK1+, CD34+, CD43−, and CD235A−.

9. The method of claim 1, wherein the multilineage human HSCs are CD34+CD38−CD45+.

10. The method of claim 1, wherein the multilineage human HSPCs and/or hematopoietic cells are CD34+CD45+.

11. An engineered cell or population of engineered cells derived from a population of human HE and produced by the method of claim 1.

12. A composition comprising the population of engineered cells of claim 11.

13. A pharmaceutical composition comprising the population of engineered cells of claim 11 and a pharmaceutically acceptable carrier.

14. The method of claim 1, further comprising the step of inducing endothelial-to-hematopoietic transition (EHT) in culture in the transfected HE to obtain human hematopoietic stem cells,
   wherein the endothelial-to-hematopoietic transition occurs by culturing the isolated HE in the presence of thrombopoietin (TPO), interleukin (IL)-3, stem cell factor (SCF), IL-6, IL-11, insulin-like growth factor (IGF)-1, erythropoietin (EPO), vascular endothelial growth factor (VEGF), basic fibroblast growth factor (bFGF), bone morphogenetic protein (BMP)4, Fms related tyrosine kinase 3 ligand (Flt-3L), sonic hedgehog (SHH), angiotensin II, and chemical AGTR1 (angiotensin II receptor type I) blocker losartan potassium.

* * * * *